United States Patent [19]

Anderson et al.

[11] Patent Number: 5,439,829
[45] Date of Patent: Aug. 8, 1995

[54] IMMOBILIZATION OF BIOLOGICALLY ACTIVE MOLECULES BY CHANGING THE OXIDATION STATE OF A CHELATED TRANSITION METAL ION

[75] Inventors: Leslie D. Anderson, Encinitas, Calif.; James A. Cook, Indianapolis, Ind.; Gary S. David, La Jolla, Calif.; Susan M. Hochschwender, Del Mar, Calif.; Mary S. Kasher, Indianapolis; Michele C. Smith, Indianapolis, both of Ind.; Willem P. C. Stemmer, Carlsbad, Calif.

[73] Assignees: Eli Lilly and Company, Indianapolis, Ind.; Hybritech Incorporated, San Diego, Calif.

[21] Appl. No.: 826,928

[22] Filed: Jan. 24, 1992

Related U.S. Application Data

[63] Continuation-in-part of Ser. No. 647,901, Jan. 30, 1991, abandoned.

[51] Int. Cl.⁶ ............... G01N 33/543; G01N 33/549; C12N 11/00; C07K 17/00
[52] U.S. Cl. ................... 436/518; 435/71.1; 435/172.3; 435/174; 435/177; 435/178; 435/181; 436/528; 436/529; 436/532; 436/824; 530/413; 530/810; 530/812; 530/813; 530/816
[58] Field of Search ............ 435/174, 177, 178, 180, 435/181, 1.1, 172.3; 530/810, 812, 813, 815, 816, 413; 436/518, 528, 529, 532, 824

[56] References Cited

U.S. PATENT DOCUMENTS

| | | | |
|---|---|---|---|
| 4,217,417 | 8/1980 | Smith | 435/180 |
| 4,569,794 | 2/1986 | Smith et al. | 260/113 |
| 4,789,630 | 12/1988 | Bloch et al. | 435/7 |

FOREIGN PATENT DOCUMENTS

0282042A2 9/1988 European Pat. Off. .
0316695A1 5/1989 European Pat. Off. .
0505151A2 9/1992 European Pat. Off. .

OTHER PUBLICATIONS

Smith, et al., *ACS Symposium Series,* 427, pp. 168–180 (1990).
Jones, et al., *Journal of Biological Chemistry,* 265:22, pp. 12782–12785 (Aug. 5, 1990).
Smith, et al., The Journal of Biological Chemistry. vol. 263, No. 15, May 25, 1988, pp. 7211–7215.
Hochuli, et al., J. Chromatography, vol. 411, pp. 177–184.
Ljungquist, et al., European Journal of Biochemistry. vol. 186, pp. 563–569.
Chen, et al., Inorg. Chem. vol. 27, 1988, pp. 2682–2687.

*Primary Examiner*—David M. Naff
*Attorney, Agent, or Firm*—Richard B. Murphy

[57] ABSTRACT

A chelating agent is covalently bonded to a biologically active molecule such as an enzyme or antibody, the biologically active molecule is contacted with a support containing a bound transition metal ion whereby the metal ion is chelated by the chelating agent and the oxidation state of the metal ion is changed by treatment with an oxidizing or a reducing agent to provide a kinetically inert oxidation state to immobilize the biologically active molecule on the support. The transition metal ion is preferably Co(II), Cr(II) or Ru(III) and the oxidation state of the metal ion is changed to Co(III), Cr(III) or Ru(II), respectively. The chelating agent can be iminodiacetic acid, nitrilotriacetic acid, terpyridine, bipyridine, triethylenetetraamine, biethylenetriamine, 1,4,7-triazacyclonane or a chelating peptide. Certain chelating agents can immobilize more than one biologically active molecule at a metal ion site on the support. The immobilized biologically active molecules can be used in affinity chromatography or in assay systems.

15 Claims, 29 Drawing Sheets resin-IDA -Co(II)-(CP-E7)   "UNLOCKED"

↓ remove non-specifically bound molecules

↓ oxidation resin-IDA -Co(III)-CP-E7   "LOCKED"

↓ add test compound "T"

[ resin-IDA-Co(III)-CP-E7
  OR
  resin-IDA-Co(III)-CP-E7-T ]   TEST COMPOUND MAY OR MAY NOT BIND TO E7

↓ add fluorescently labelled RB*

[ resin-IDA-Co(III)-CP-E7-RB*
  OR
  resin-IDA-Co(III)-CP-E7-T ]

FIG. I

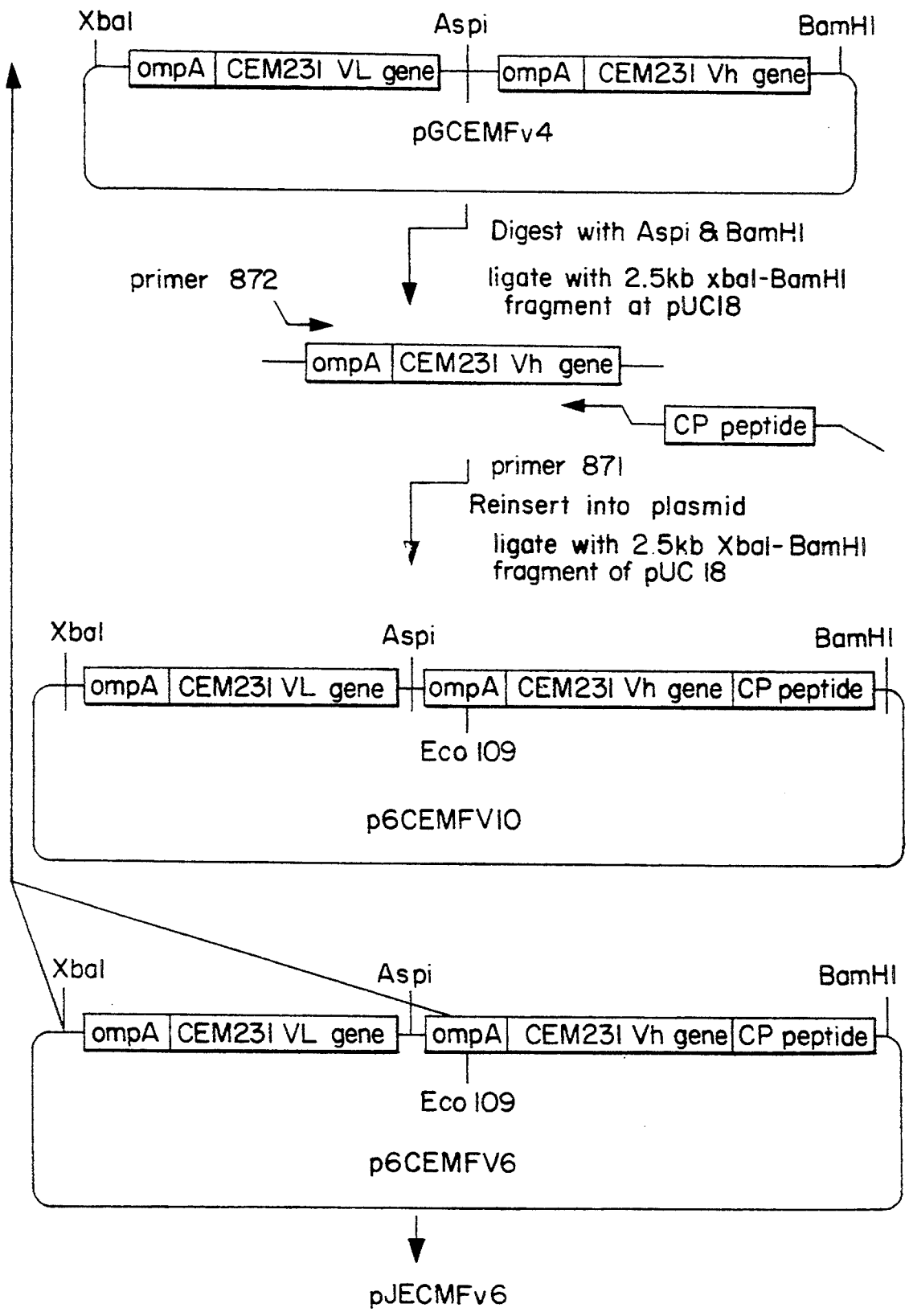
FIG. 12 CONT.'

IMMOBILIZATION OF BIOLOGICALLY ACTIVE MOLECULES BY CHANGING THE OXIDATION STATE OF A CHELATED TRANSITION METAL ION

This application is a continuation in part of U.S. patent application Ser. No. 07/647,901, filed Jan. 30, 1991, now abandoned.

BACKGROUND OF THE INVENTION

Immobilized metal ion affinity chromatography (IMAC) is a technique used for the purification of proteins. The technique is based on the natural ability of some proteins to bind to transition metals. Porath, J., Carlsson, J., Olsson, I., and Belfrage, G. (1975) Nature 258 598–599. The affinity of proteins for transition metals derives from the properties of amino acids within the protein's primary structure which interact with and bind to metal ions. However, the occurrence of such metal/protein binding is random, due to the fact that not all proteins possess such metal binding amino acid sequences. Moreover, the strength of the bond to the metal ion varies unpredictably with the particular protein. Furthermore, if two or more protein molecules in a given mixture possess such metal binding sequences, the usefulness of the technique as a purification method is diminished since both will bind to the immobilized metal ion.

These shortcomings of the IMAC technique were solved by the advent of the CP-IMAC technique which provided a predictable and specific method for the purification of proteins by exploiting this natural protein-metal binding phenomenon. The term "CP-IMAC" reflects the use of "chelating peptides" to specifically bind immobilized metal ions and purify proteins which contain such chelating peptides via IMAC principles. Chelating peptides are short amino acid sequences which are specifically designed to interact with and bind to metal ions. Smith, M. C., Furman, T.C., Ingolia, T.D., Pidgeon, C. (1988) J. Biol. Chem. 263, 7211–7215. A protein possessing a chelating peptide (herein termed a CP-protein) will bind to an immobilized metal ion with high specificity in a relatively stable manner. This allows one to remove all nonspecifically or weakly bound proteins from the column and later isolate the purified CP-protein. If desired, the CP-protein may then be enzymatically or chemically treated to remove the chelating peptide leaving only the purified protein of interest. However, the utility of CP-IMAC is restricted by the transient nature of the CP-protein/metal complex. The utility of chelating peptides in conjunction with proteins could be expanded to many other applications if one were able to more permanently bind the protein to the support matrix.

The instant invention describes a reversible method of forming a kinetically inert complex between a CP-protein and a metal ion by binding the CP-protein to the metal ion through CP-IMAC methodology and subsequently varying the oxidation state of the metal ion so as to convert the labile complex used in the CP-IMAC procedure to a kinetically inert complex.

SUMMARY OF THE INVENTION

The instant invention provides a method of crosslinking molecules through the use of a metal ion as a connective medium. This invention has broad applicability as set forth below in the detailed description and claims. Bifunctional molecules created through the use of this linkage method have a broad range of applications. Although other chemical means for crosslinking molecules exist, the specificity provided by chelating peptides and organic chelating species as set forth below, for metal ions provides one with the ability to engineer the linkage to occur at a particular place in the molecule, especially where that molecule is a protein.

The instant invention further provides a simplified and improved method for immobilizing proteins which is useful in the purification of proteins and in the use of proteins in biological assay systems. In conventional procedures, one generally purifies a protein (by CP-IMAC techniques or otherwise), elutes the purified protein from the chromatographic column, and then reintroduces this purified protein to a second column material which will immobilize the protein for use in affinity assay procedures. However, such methods require multiple steps and at least two different Solid Supports to prepare an affinity assay column. The instant invention simplifies existing procedures to a single column procedure by an improvement in the CP-IMAC technique.

The essence of the instant invention comprises the formation of a kinetically inert complex between a transition metal ion and a Biologically Active Molecule or reporter group which possesses an endogenous metal binding site or which has been modified to contain one. According to a method of this invention, the metal ion used in the purification of a protein by the CP-IMAC procedure is oxidized or reduced to form a kinetically inert complex between the CP-protein and the bound metal ion. This kinetically inert [immobilized metal/CP-protein] complex provides a component of an assay system useful for studying the interaction of any of a variety of ligands with the immobilized CP-protein. The instant invention takes advantage of the specificity inherent in the CP-IMAC technique yet opens new avenues in the development of assay systems of greater simplicity and effectiveness.

The invention further provides a method of purifying IPs or receptors on a Solid Support. For example, an immobilized CP-derivatized protein may be used to isolate and purify antibodies against the protein. Immobilization of IPs or other Biologically Active Molecules utilizing the methodology of %he instant invention enables one to orient these molecules so as to maximize exposure of the antigen or ligand binding site in an affinity chromatography system. As an example, medical diagnostic test kits employ IPs to indicate the presence of antigens characteristic of disease states. This invention provides a method useful for orienting such IPs so as to enhance their utility and efficacy in such systems.

Furthermore the invention provides a method of forming heterodimeric, homodimeric or multimeric complexes by crosslinking two or more Biologically Active Molecules or reporter groups with endogenous metal binding sites or ones that have been modified to contain metal binding sites.

DETAILED DESCRIPTION OF THE INVENTION BRIEF DESCRIPTION OF THE FIGURES

Figure 2:
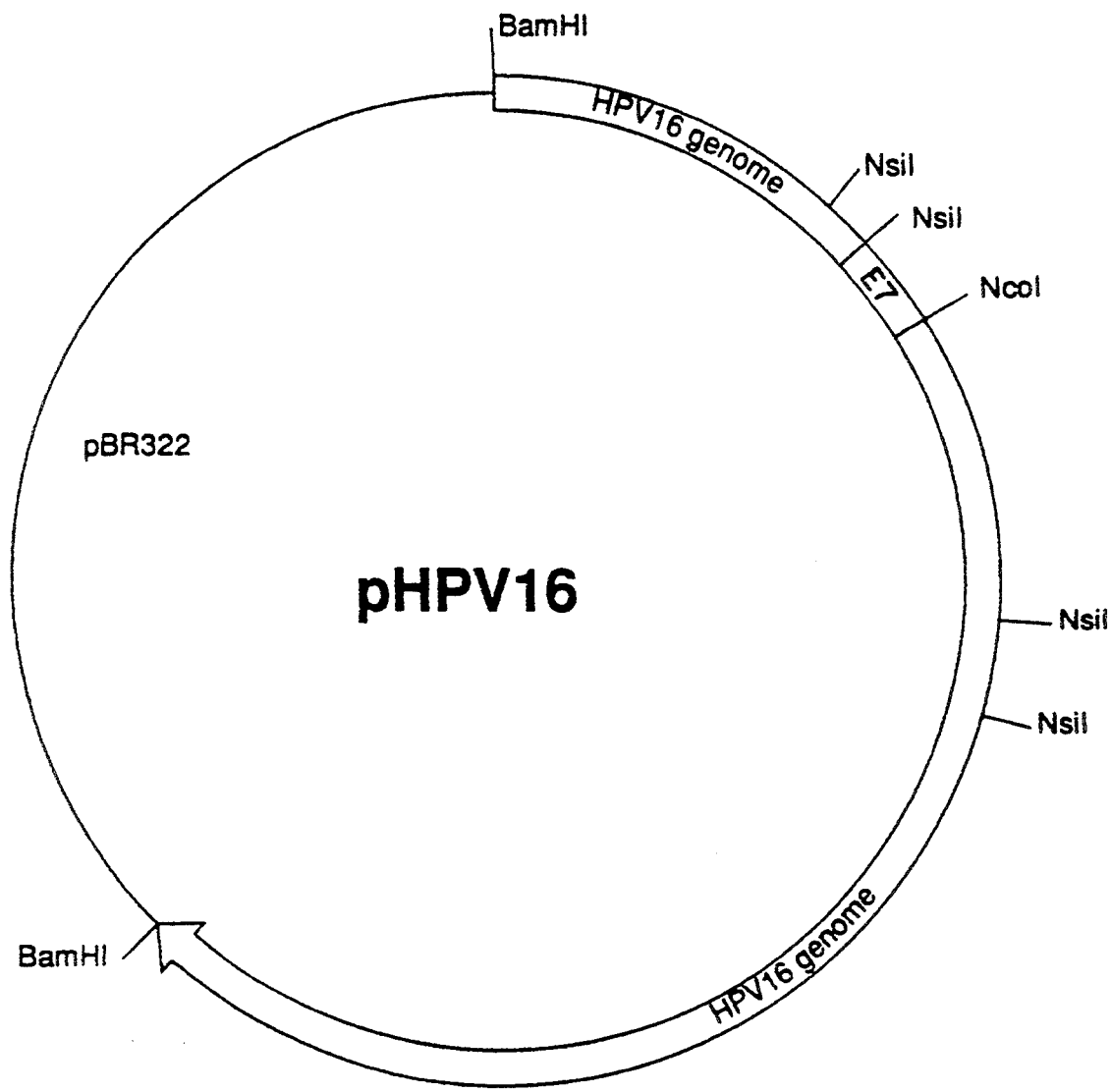

The restriction site and function maps presented in the accompanying drawings are approximate representations of the recombinant DNA vectors discussed herein. The restriction site information is not exhaustive; therefore there may be more restriction sites of a given type on the vector than are illustrated in the drawings.

FIG. 1—A schematic representation of the assay system as exemplified herein utilizing the CP-E7 fusion oncoprotein and the RB anti-oncoprotein.

FIG. 2—A restriction site and function map of plasmid pHPV16.

Figure 3:
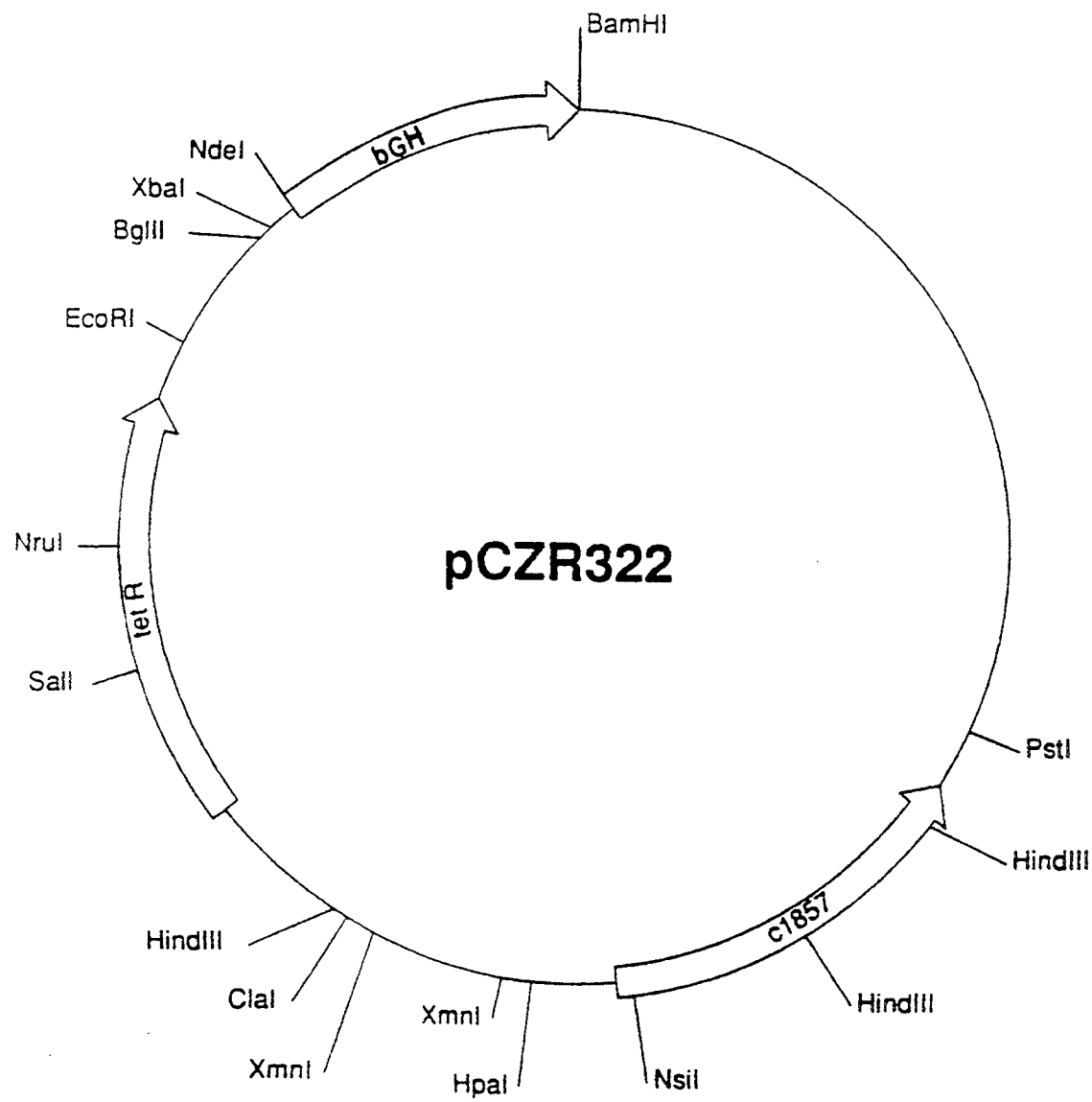

FIG. 3—A restriction site and function map of plasmid pCZR322.

Figure 4:
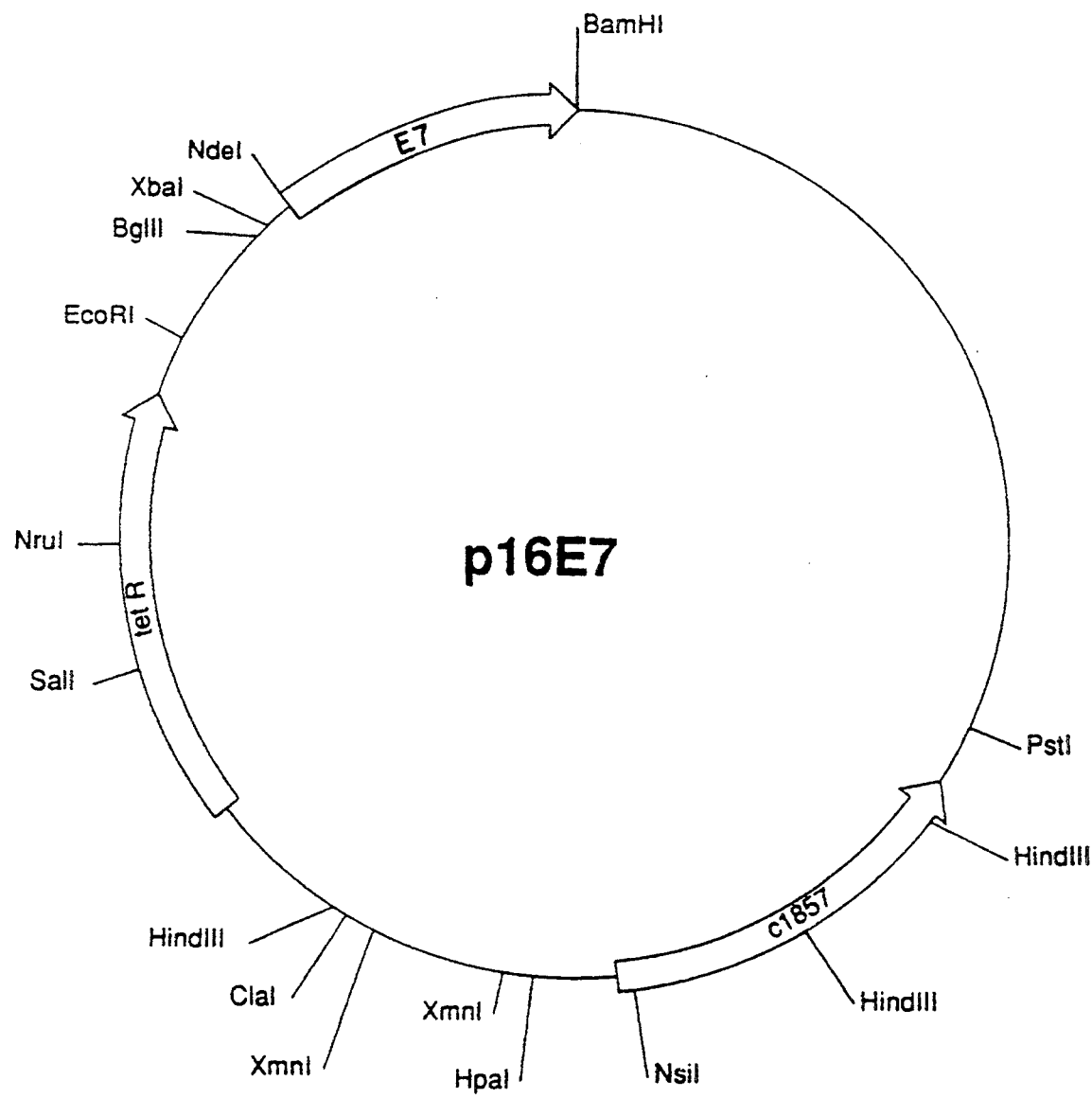

FIG. 4—A restriction site and function map of plasmid p16E7.

Figure 5:
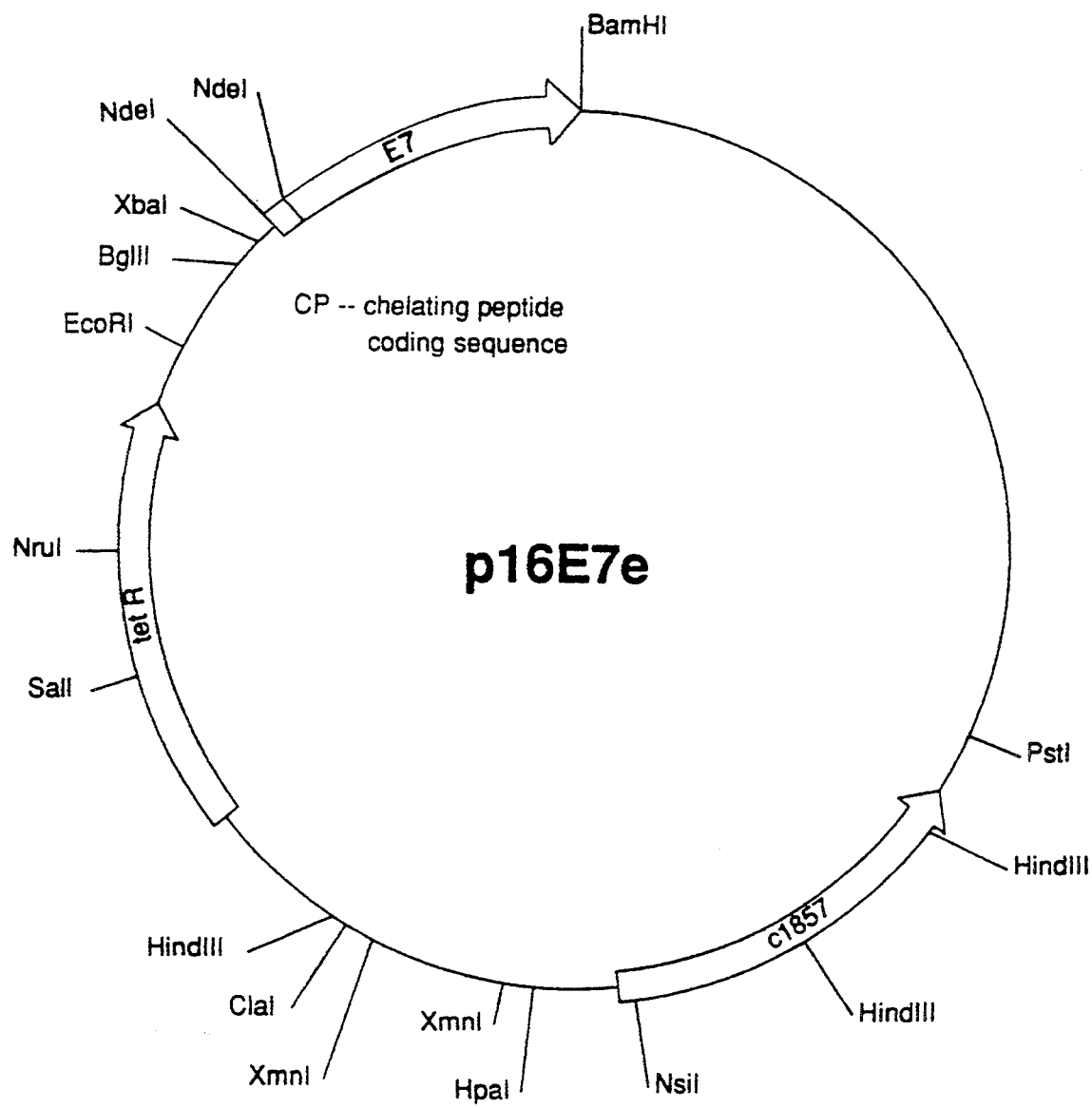

FIG. 5—A restriction site and function map of plasmid p16E7e.

Figure 6:
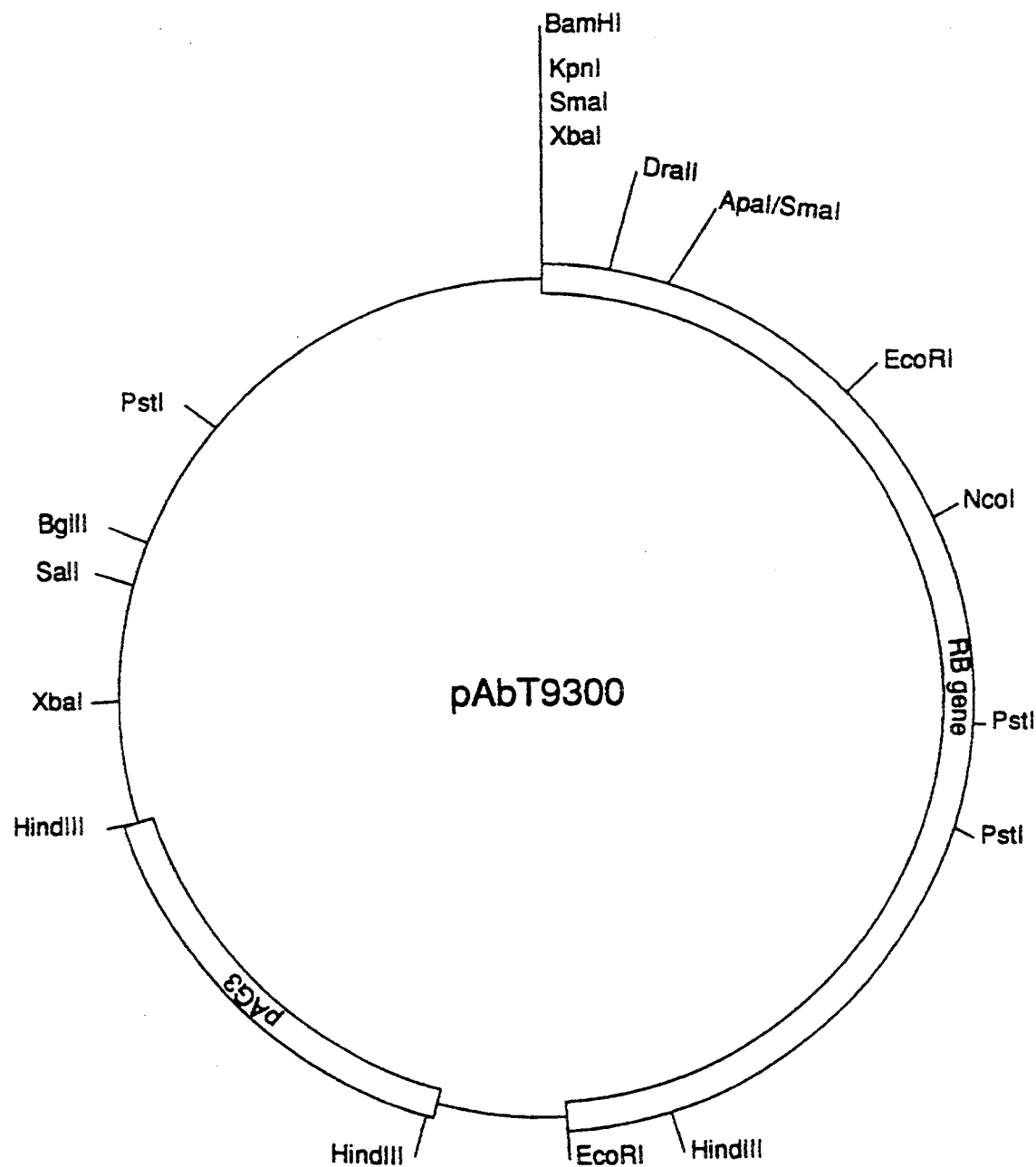

FIG. 6—A restriction site and function map of plasmid pAbT9300.

Figure 7:
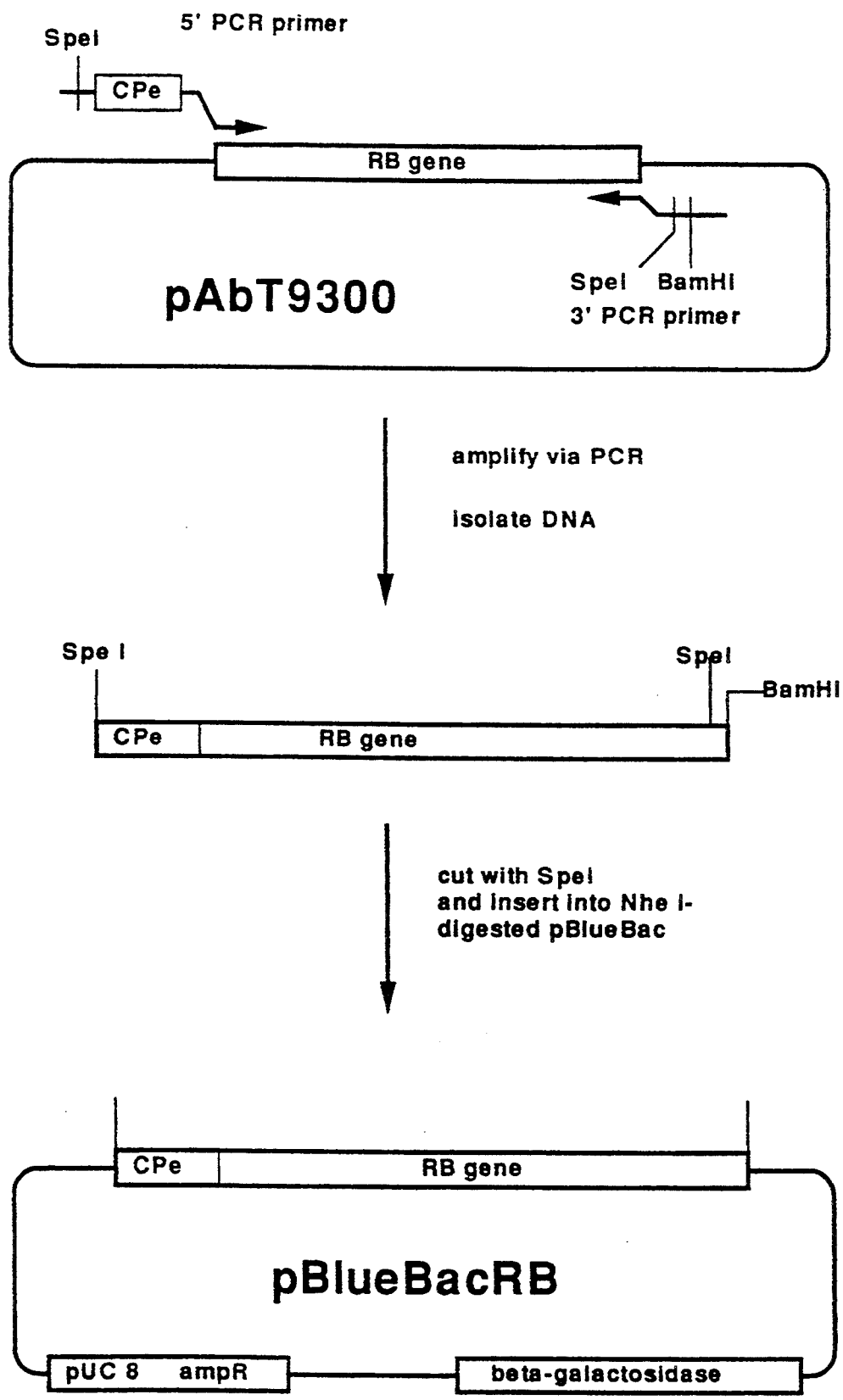

FIG. 7—A schematic representation of the synthesis of plasmid pBlueBacRB.

Figure 8:
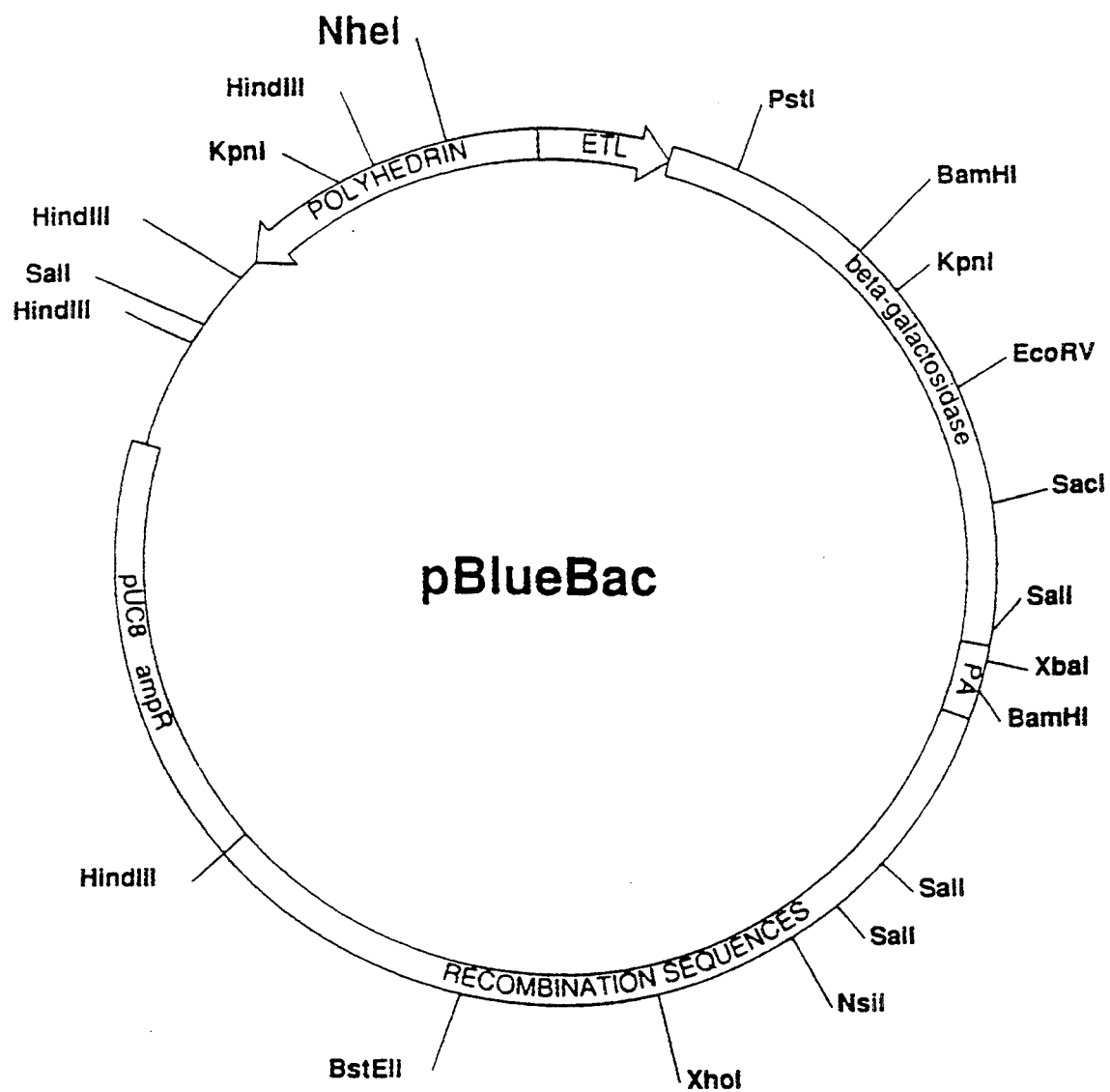

FIG. 8—A restriction site and function map of plasmid pBlueBac.

Figure 9:
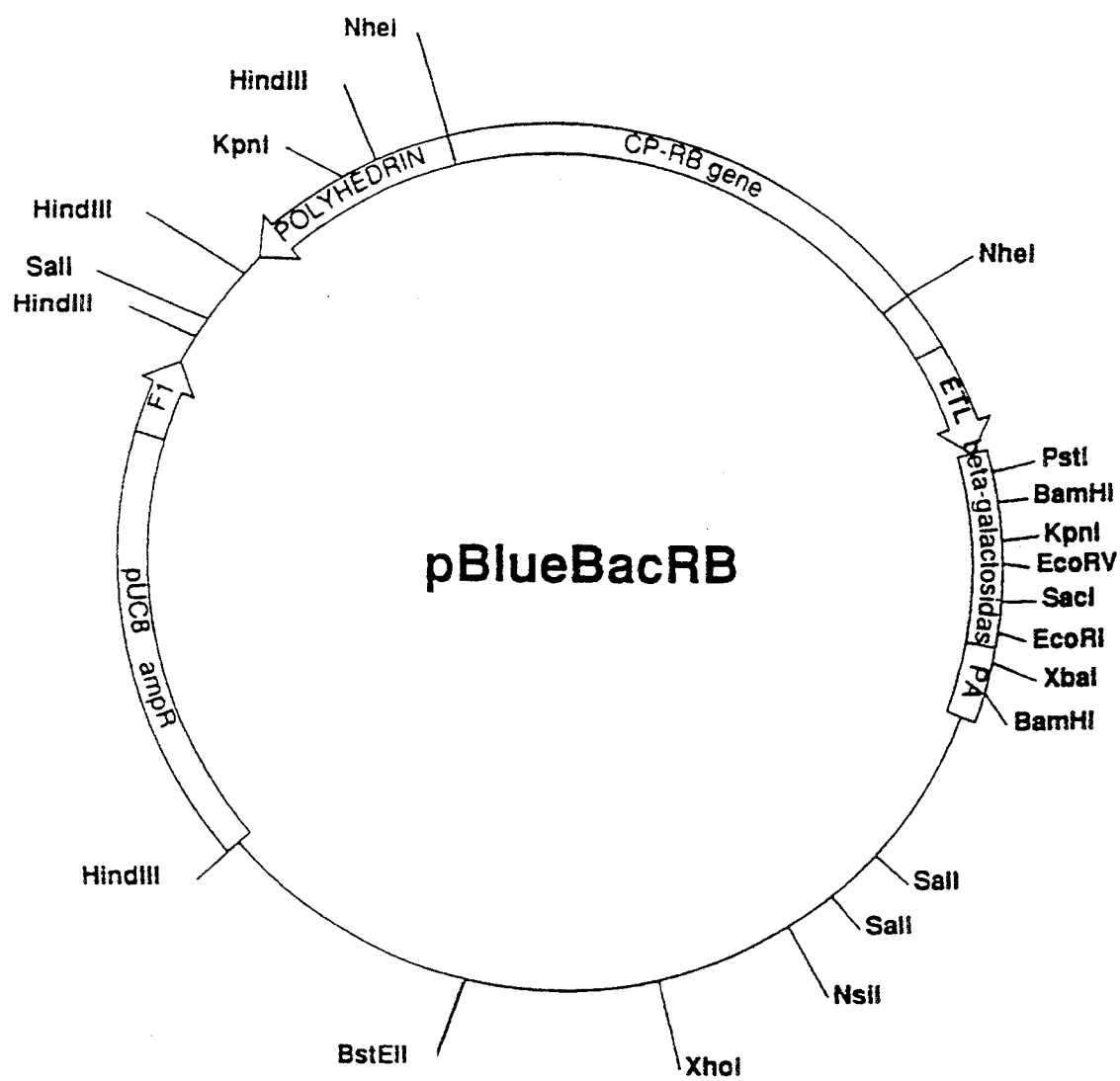

FIG. 9—A restriction site and function map of plasmid pBlueBacRB.

Figure 10:
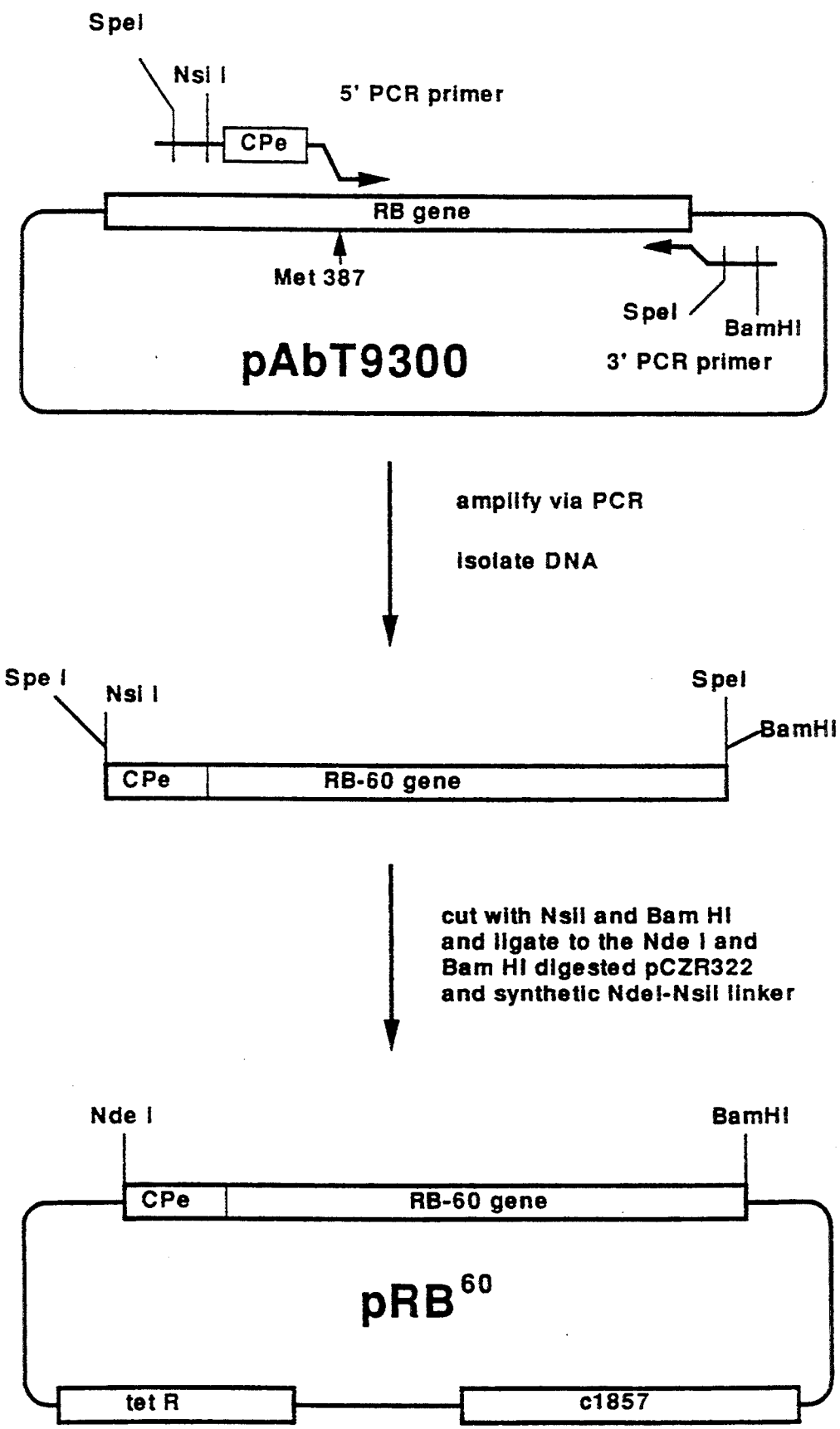

FIG. 10—A schematic representation of the synthesis of plasmid pRB$^{60}$.

Figure 11:
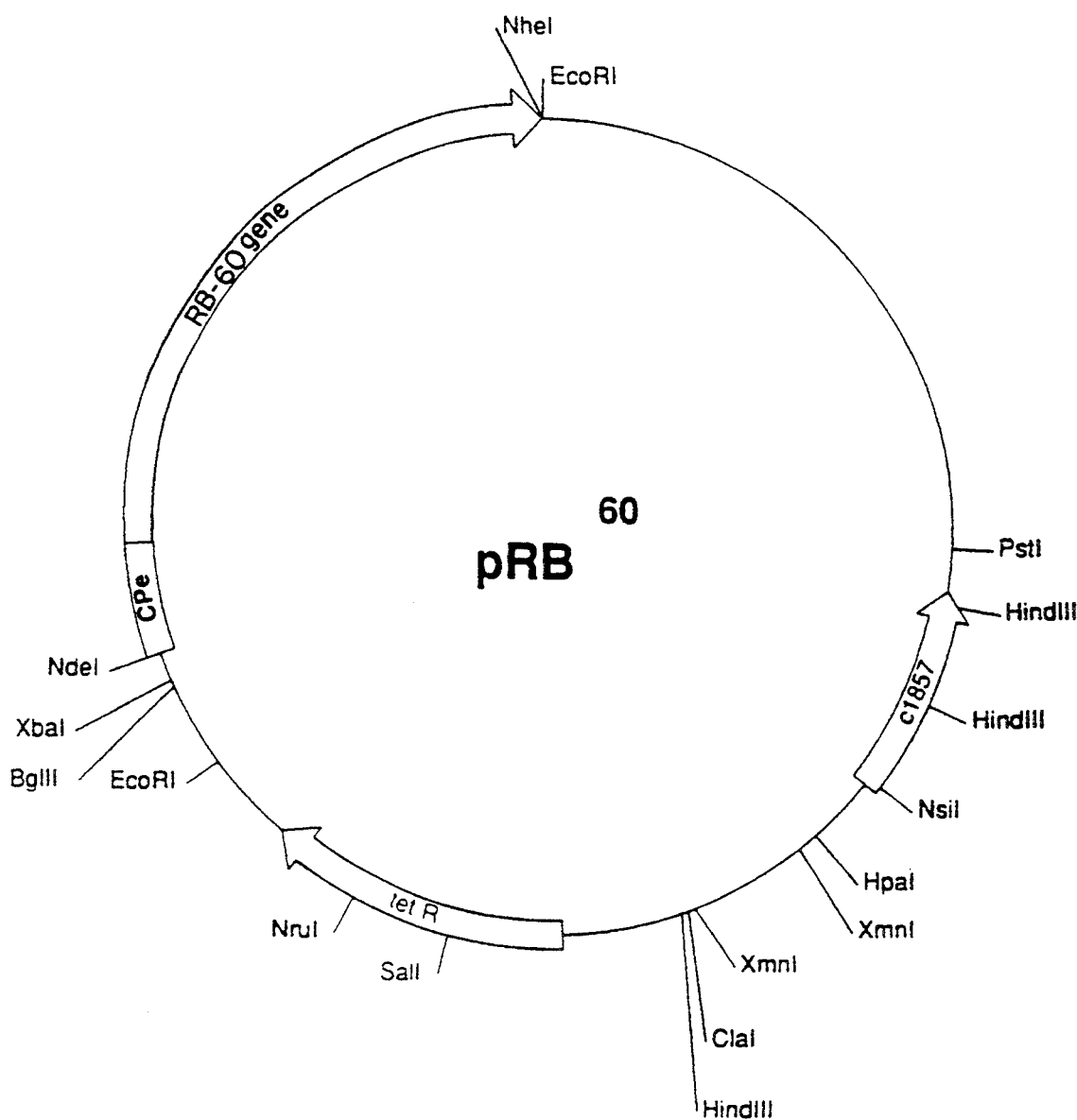

FIG. 11—A restriction site and function map of plasmid pRB$^{60}$.

Figure 12:
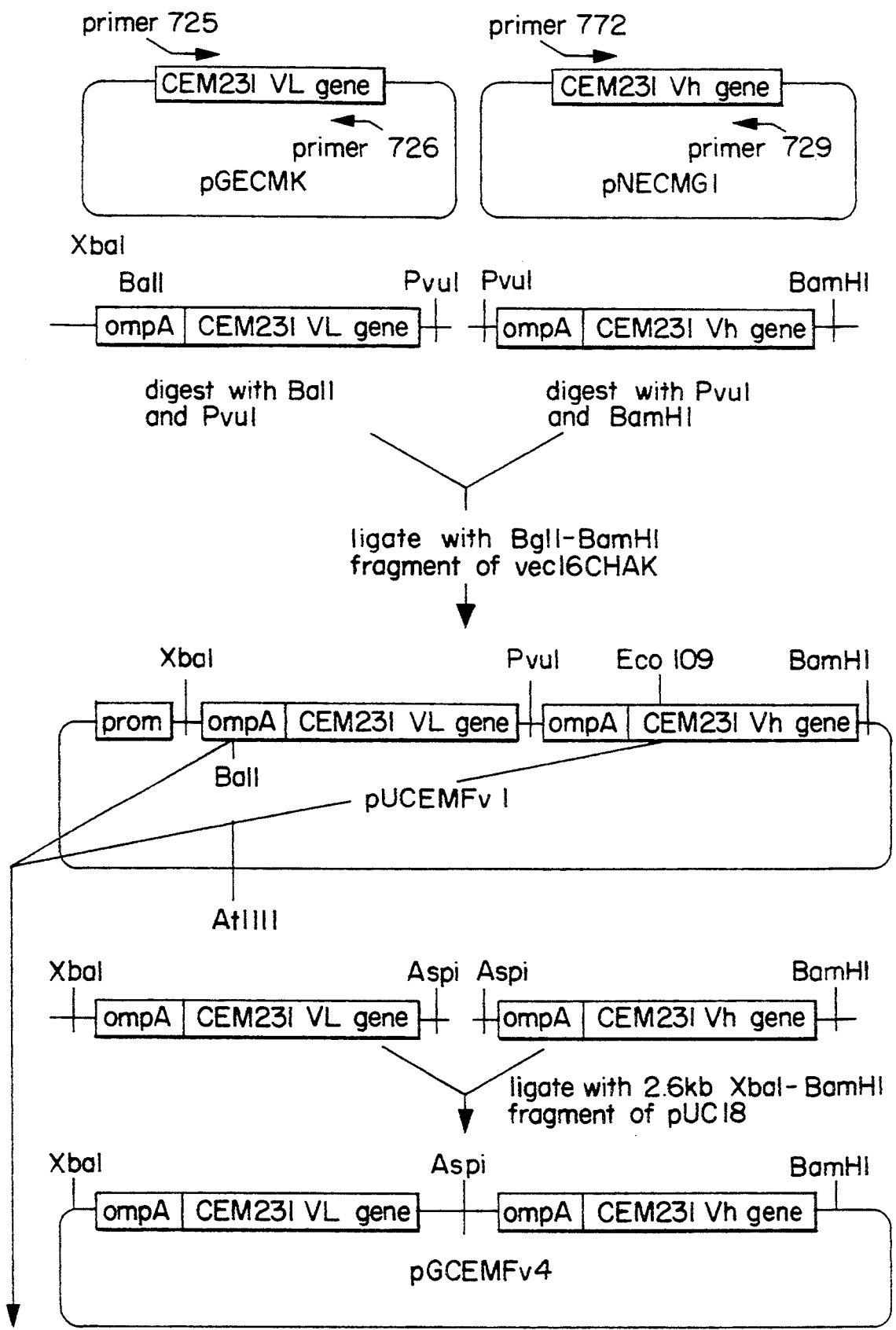

FIG. 12—A schematic representation of the creation of plasmid pJECMFv6.

Figure 13:
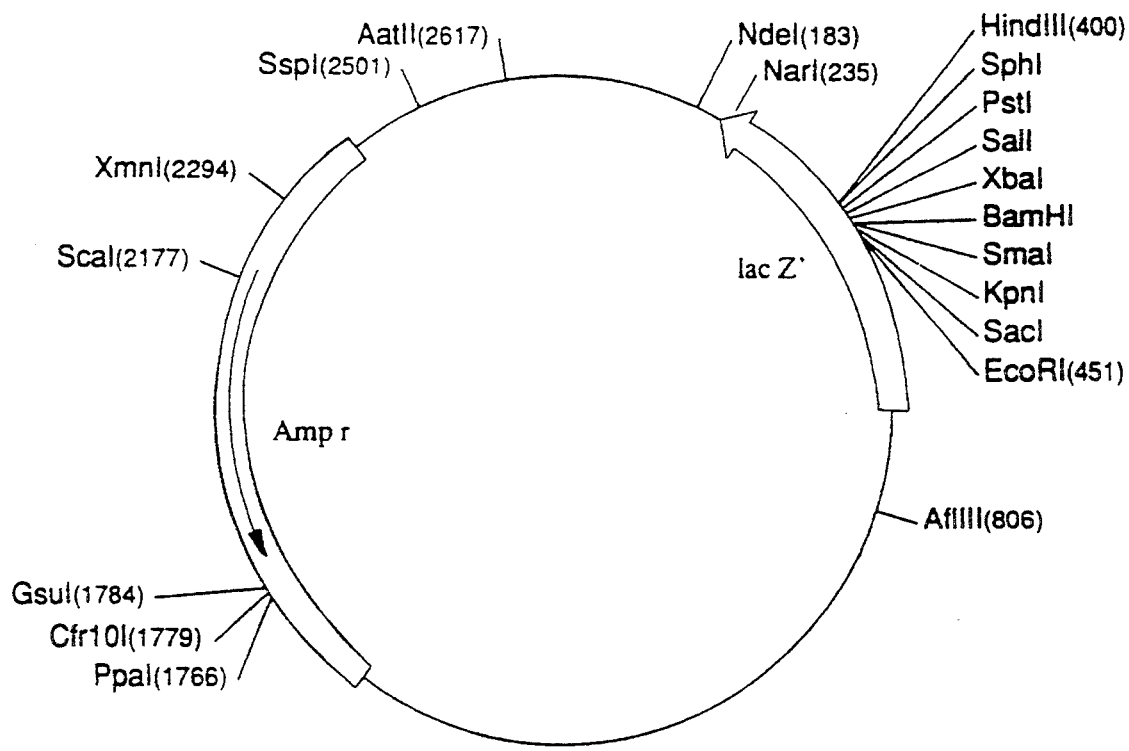

FIG. 13—A restriction site and function map of plasmid pUC18.

Figure 14:
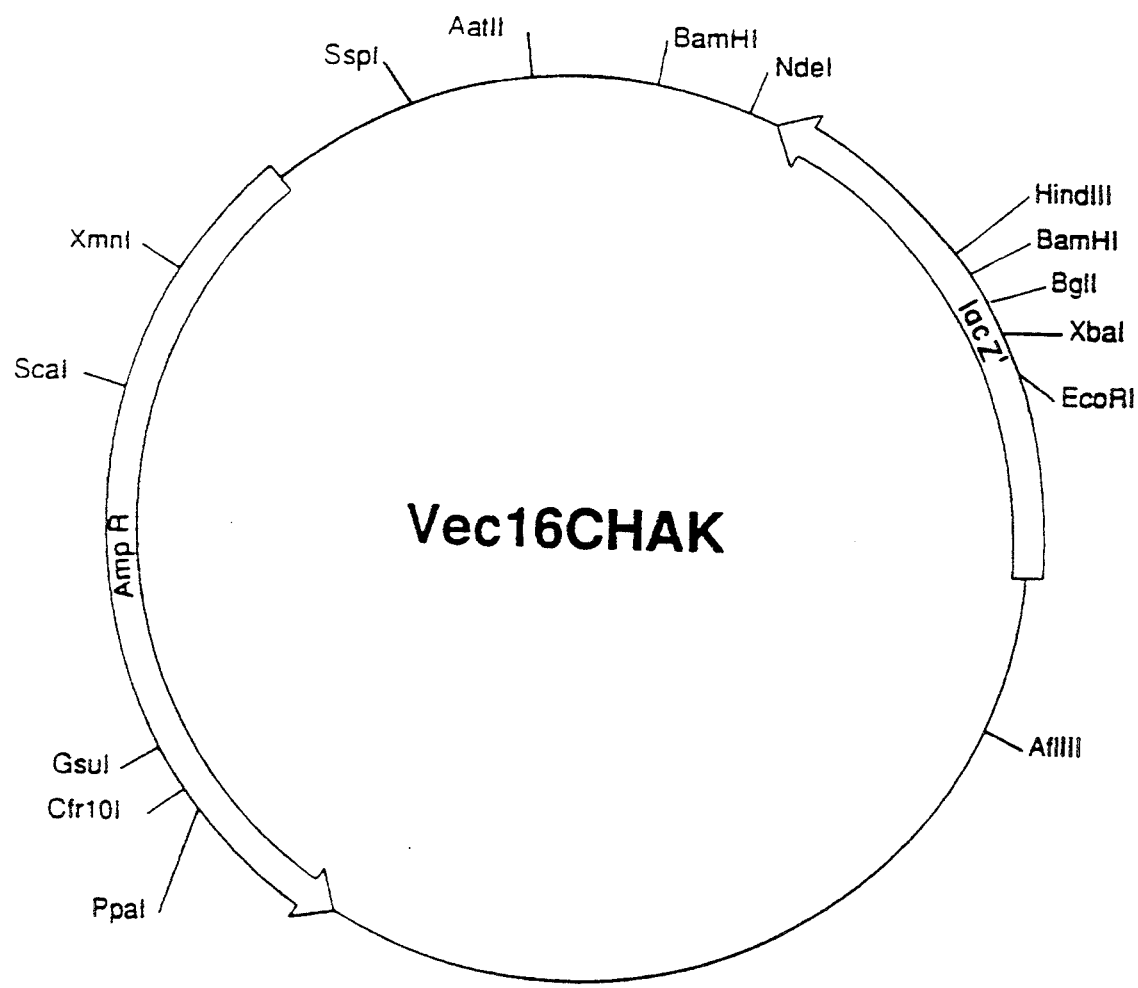

FIG. 14—A restriction site and function map of plasmid Vec16CHAK.

Figure 15:
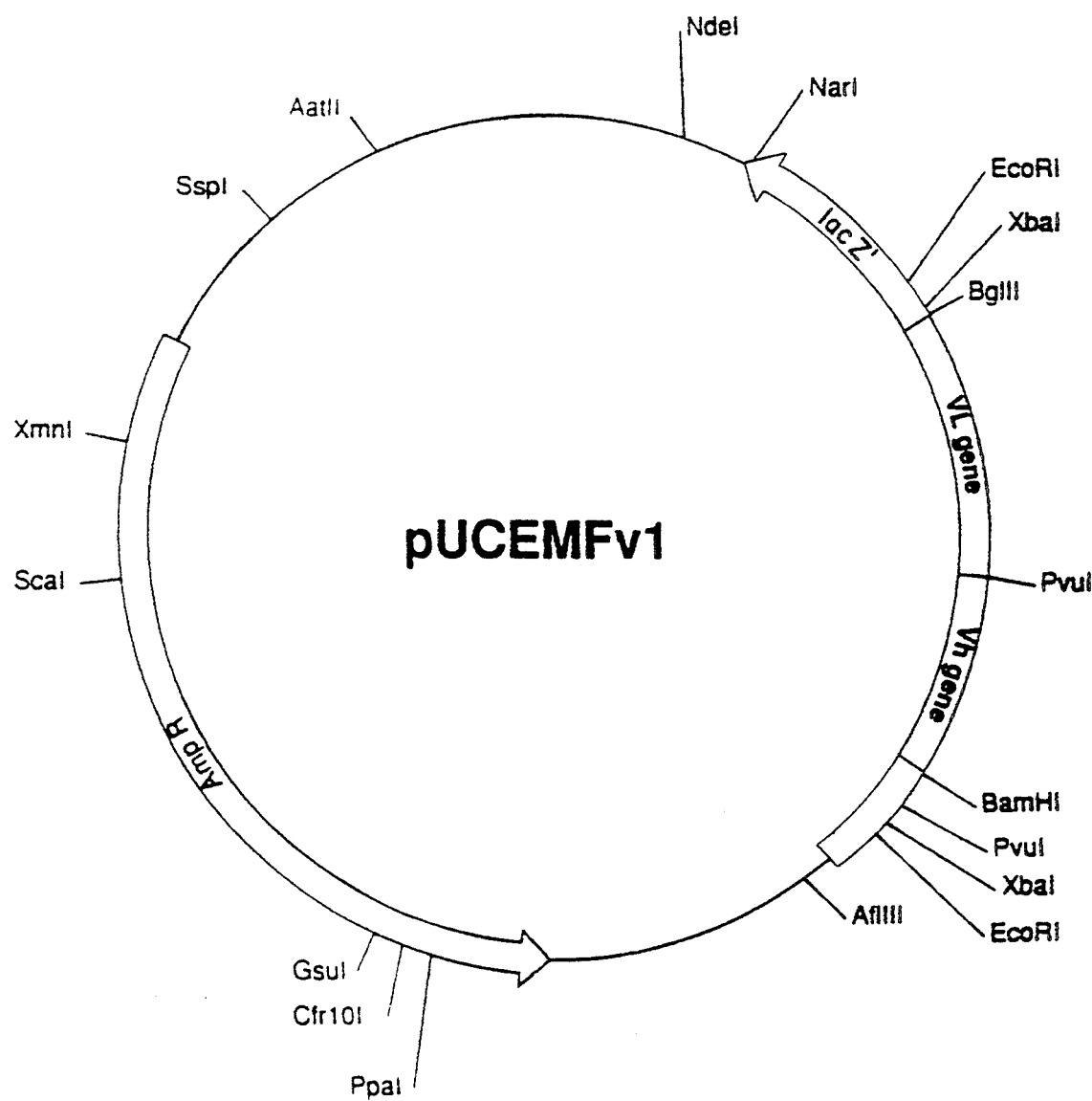

FIG. 15—A restriction site and function map of plasmid pUCEMFv1.

Figure 16:
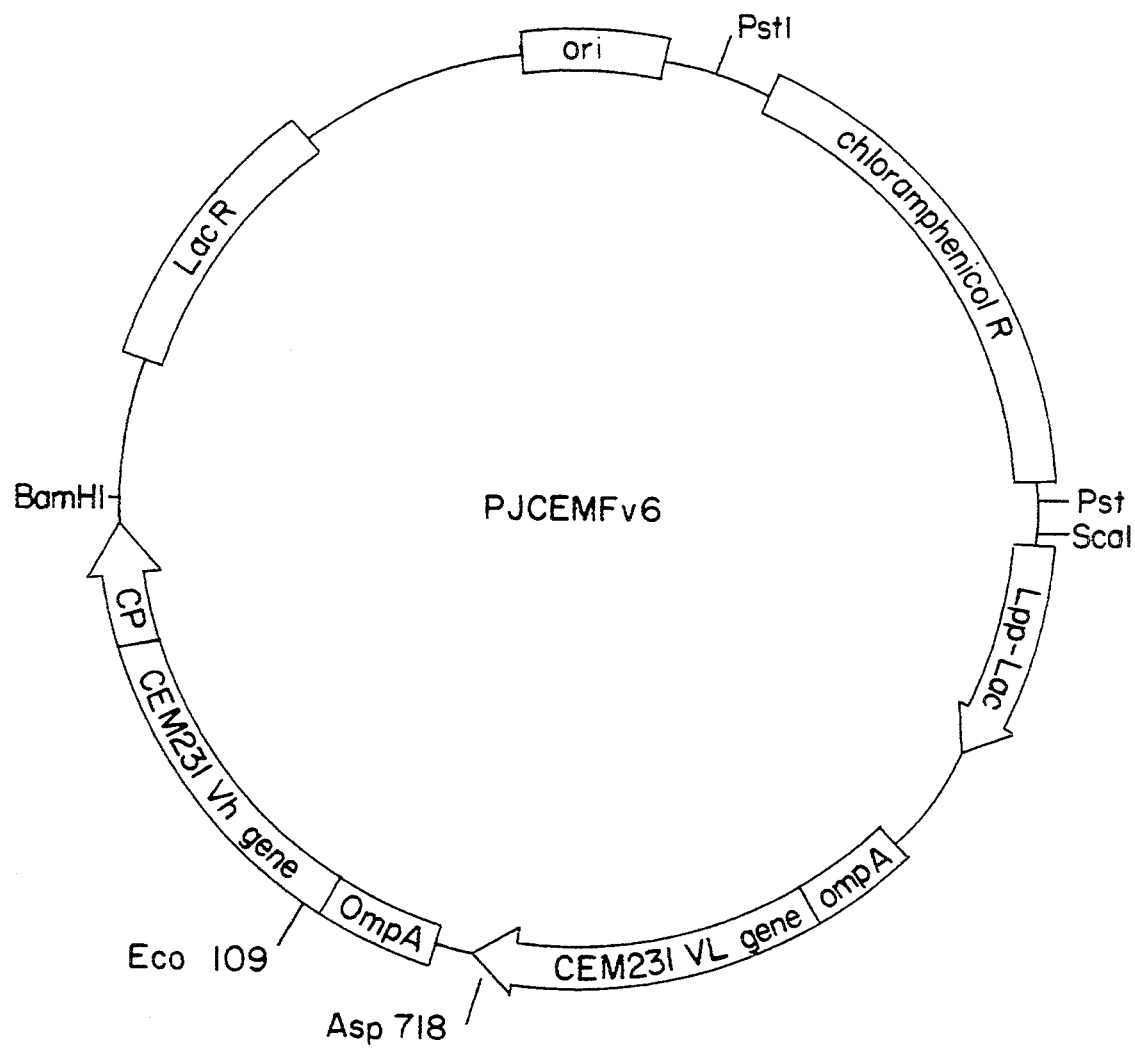

FIG. 16—A restriction site and function map of plasmid pJCEMFv6.

Figure 17:
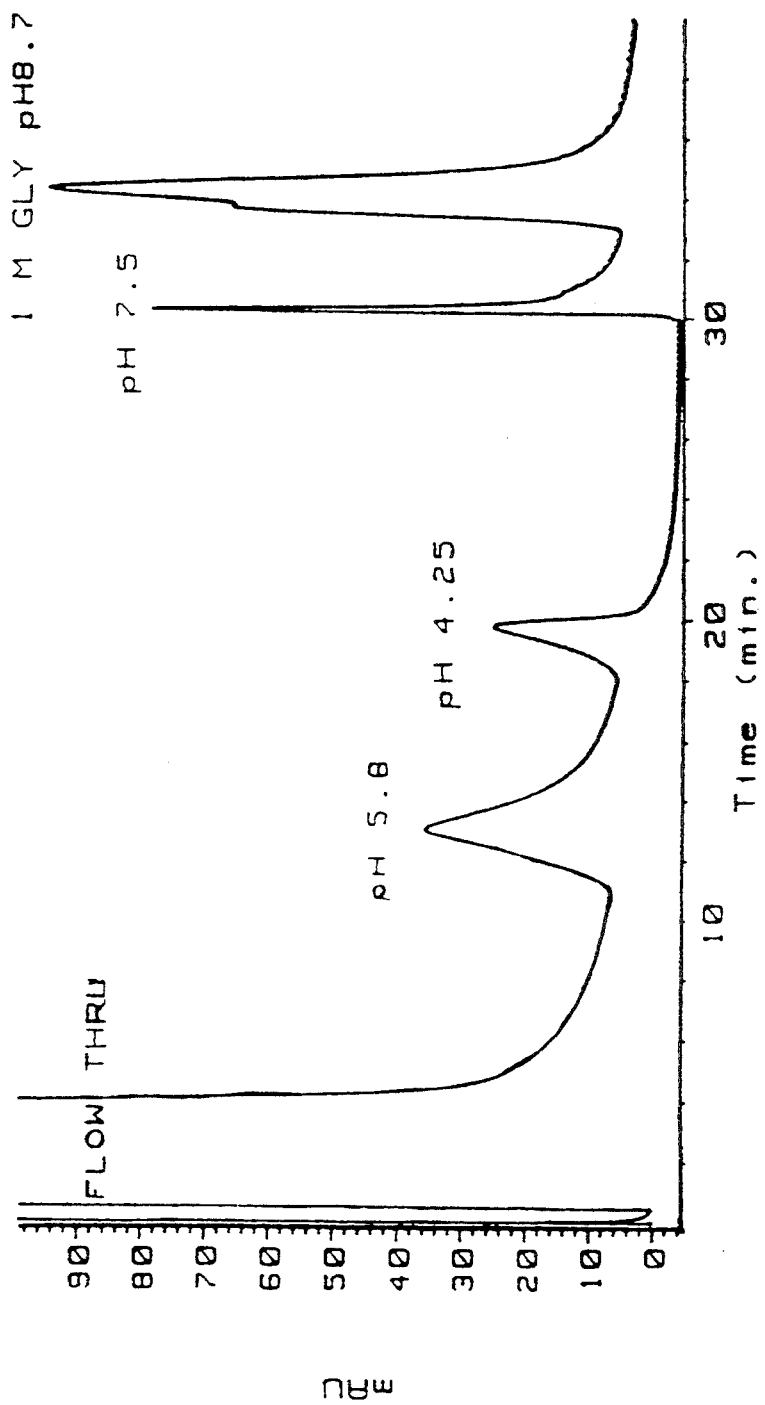

FIG. 17—IMAC Chromatography of CHEL 13 media. 20 ml of media was concentrated to 2.5 ml and loaded onto the 2.×30 mm Ni(II) IMAC column at 1.0 ml/min. Bound protein was eluted with a series of step gradients. Step 1; 50% buffer A, 50% buffer B (pH 5.8), step 2; 100% buffer B, step 3; 100% buffer A, step 4; 100% buffer C.

Figure 18:
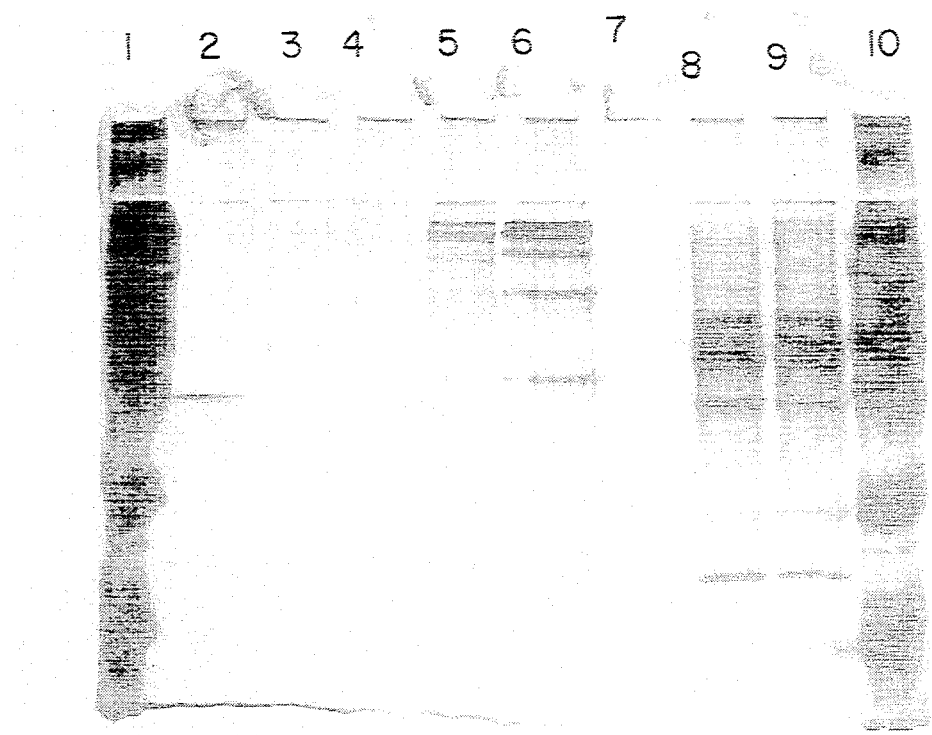

FIG. 18—SDS-PAGE analysis of fractions from the IMAC run in FIG. 17. Proteins were separated on a 10% gel in the absence of DTT.Lanes 1 & 10; high MW standards, lane 2; pH 8 wash, lane 3; pH 4.25 wash, lane 4; pH 7.5 wash, lanes 5 & 6; glycine wash fractions, lane 8; column flow through, lane 9 CHEL 13 media.

Figure 19:
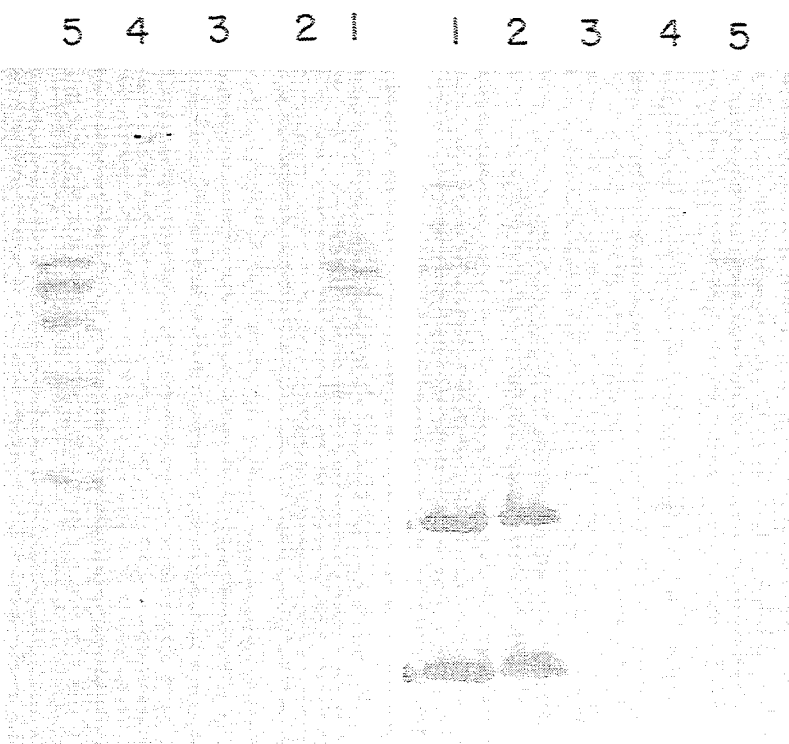

FIG. 19—Western blot analysis of IMAC fractions using A. anti human IgG heavy chain and B. anti human IgG light chain. Lane 1; glycine wash fraction, lane 2; pH 4.25 wash, lane 3; pH 5.8 wash, lane 4; column flow through, lane 5; CHEL 13 media.

Figure 20:
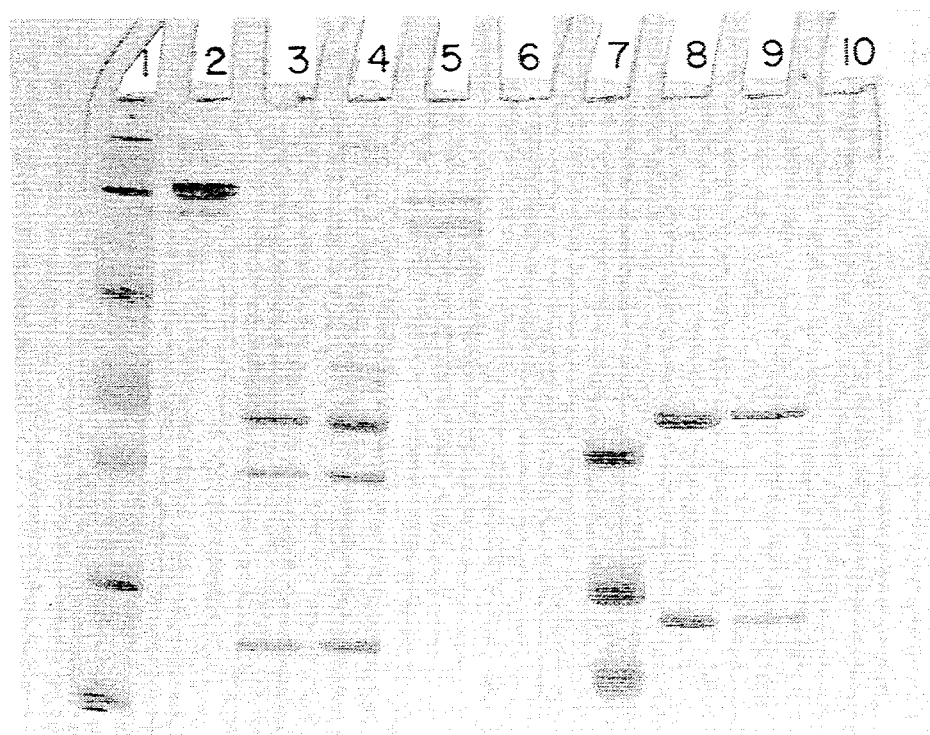

FIG. 20—Nonreducing and reducing SDS-PAGE analysis of IMAC fractions. Lanes 1–5 nonreducing, lanes 7–9 reducing. Lane 1; High MW standard, lane 2; XCEM control antibody, lane 3; CHEL 13 media, lane 4; column flow through, lane 5 glycine wash fraction, lane 6 & 10; blank, lane 7; low MW standard, lane 8 XCEM control antibody, lane 9; glycine wash fraction.

Figure 21:
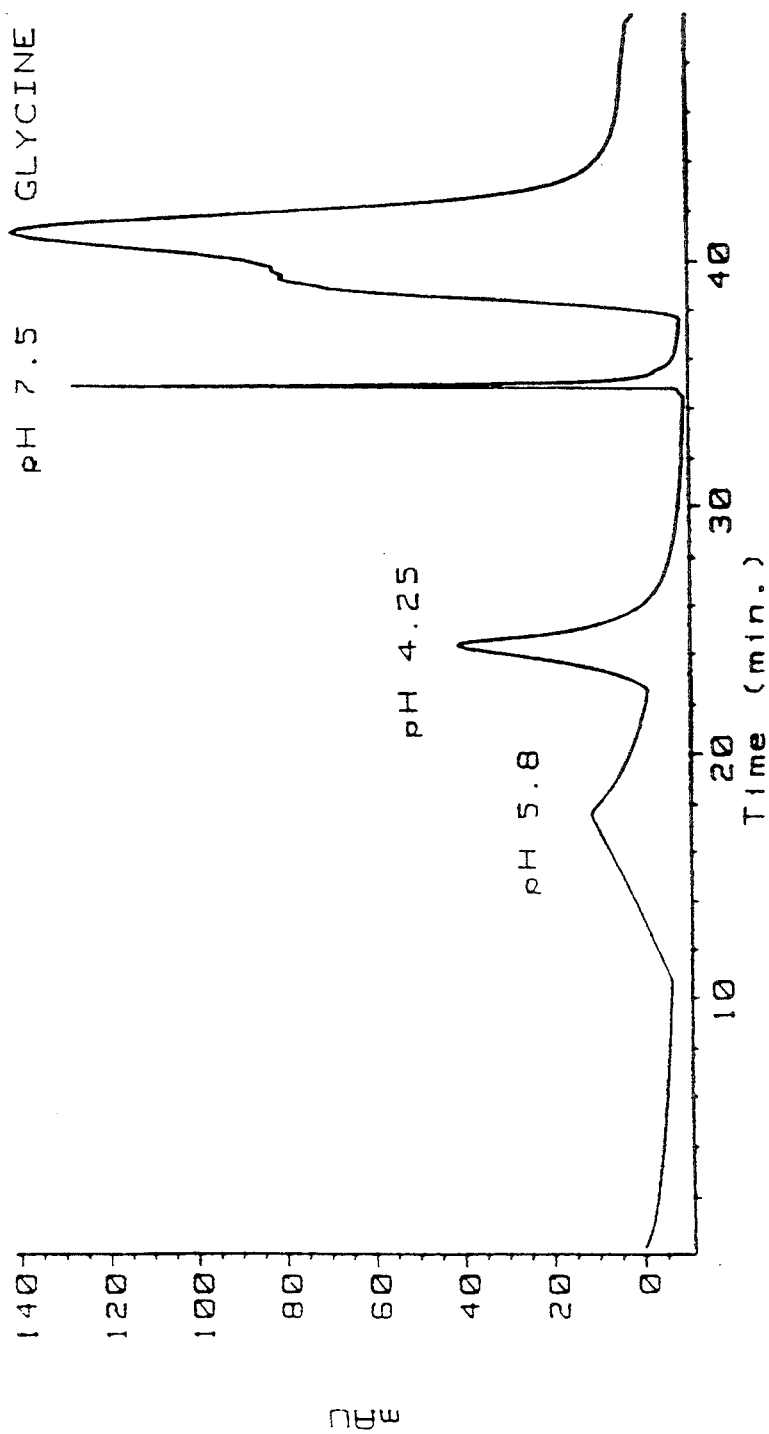

FIG. 21—IMAC chromatography of CHEL media (cells more adapted to serum free media). 300 ml of media was loaded onto the 4.6×50 mm IMAC column at 9.9 ml/min. Bound protein was eluted with a series of step gradients at 3.0 ml/min.

Step 1; 50% buffer A, 50% buffer B (pH 5.8), step 2; 100% buffer B, step 3; 100% buffer A.

The final gradient step was a 10 min gradient from 100% A to 100% C.100% buffer C.

Figure 22:
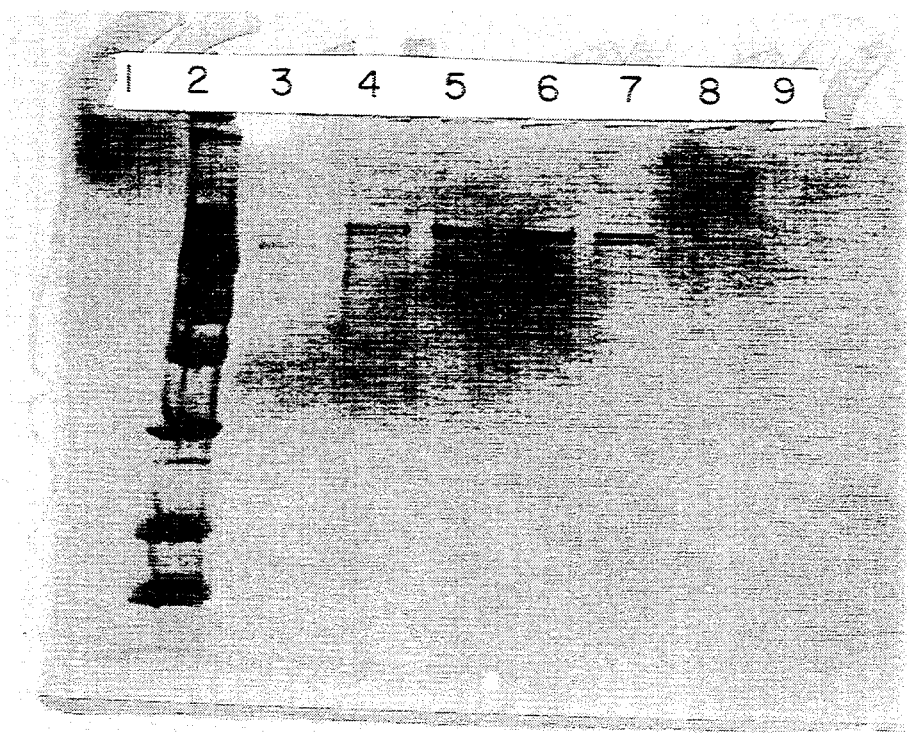

FIG. 22—Non-reducing SDS-PAGE analysis of the glycine gradient fractions from FIG. 21. Lane 2=high MW standards; Lane 3=fraction 39; Lane 4=fraction 40; Lane 5=fraction 42; Lane 6=fraction 43.

Figure 23:
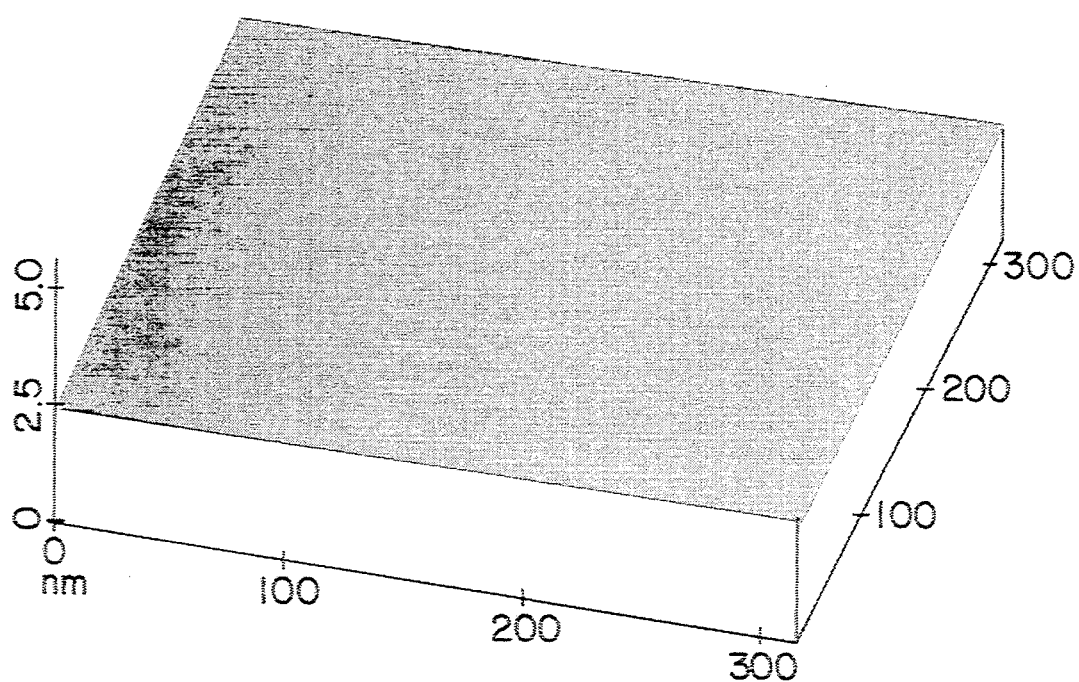

FIG. 23—Atomic force microscopy image of a freshly cleaved mica surface imaged under PBS, pH 7 using a 12 micrometer scanner head and a 100 micrometer cantilever. The force is approximately $10^{-7}$ newtons.

Figure 24:
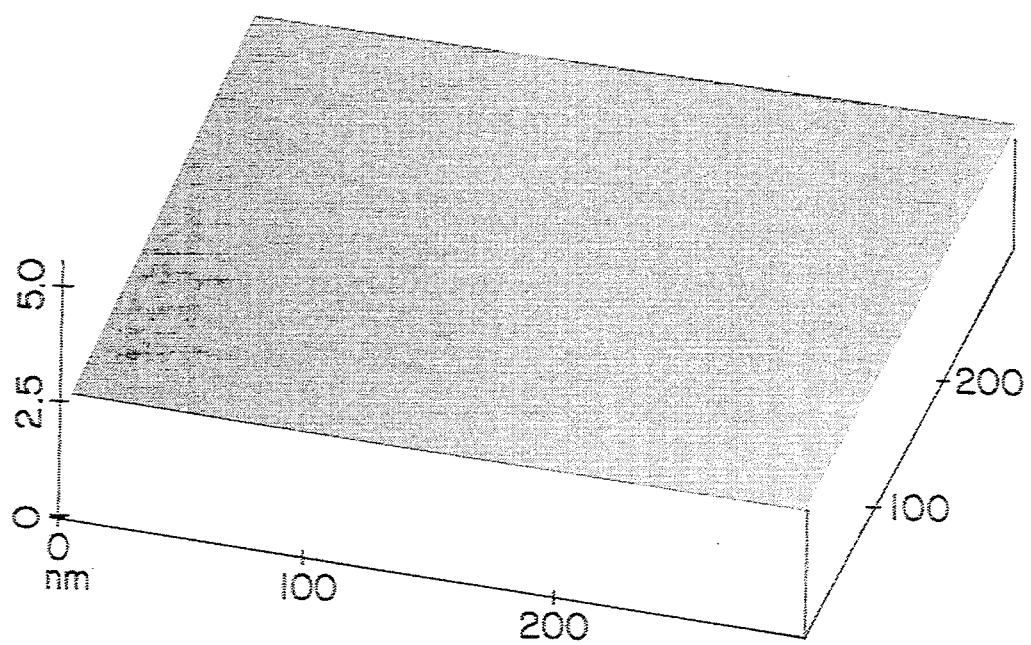

FIG. 24—Atomic force microscopy image of a nickel impregnated mica surface. 5 μl of 1 mM nickel chloride was spotted on a freshly cleaved mica surface, allowed to sit for 1 minute, and rinsed with Milli-Q ® water. This was air-dried at room temperature for 20 minutes, and imaged under PBS, pH 7 using a 12 micrometer scanner head and a 100 micrometer cantilever. The force is approximately $10^{-9}$ newtons.

Figure 25:
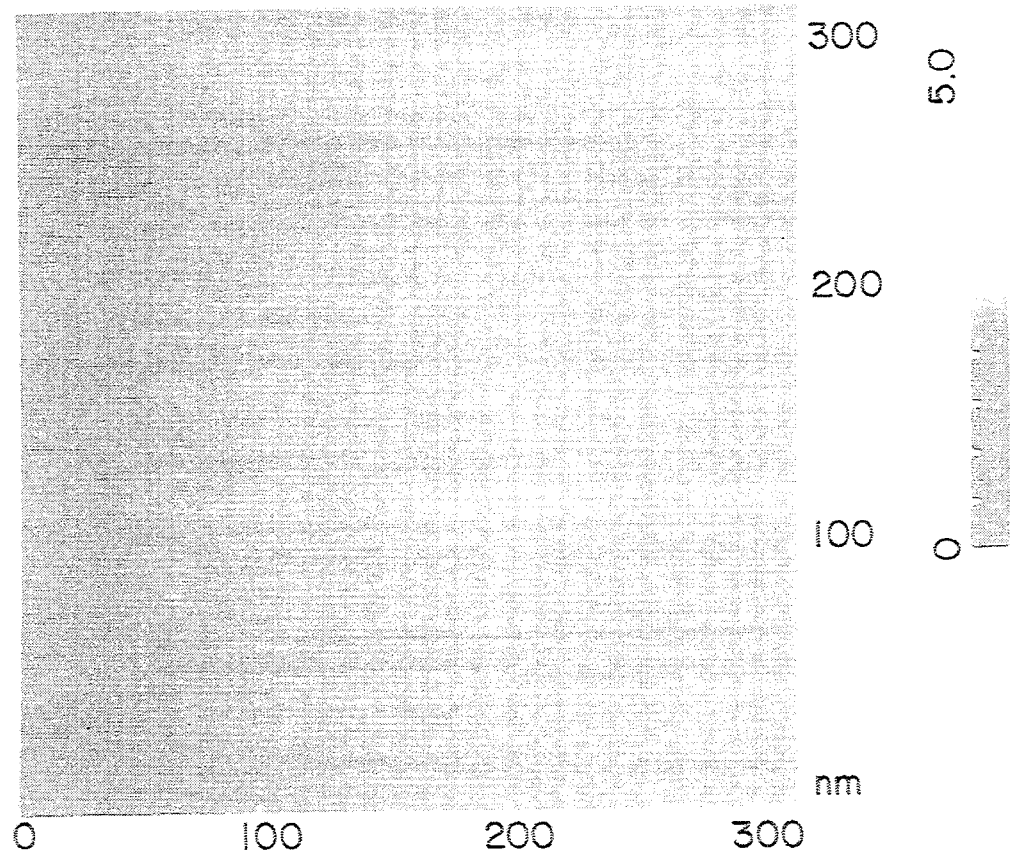

FIG. 25—Atomic force microscopy image of a Mica-CHEL 13. 100 μl of 0.5 μg/ml CHEL 13 was injected into the fluid cell on a freshly cleaved mica surface, and allowed to be in contact with the mica surface for 10 minutes. The fluid cell was then flushed with phosphate-buffered saline, and imaged under PBS, pH 7 using a 12 micrometer scanner head and a 100 micrometer cantilever. The force was approximately $10^{-9}$ Newtons.

Figure 26:
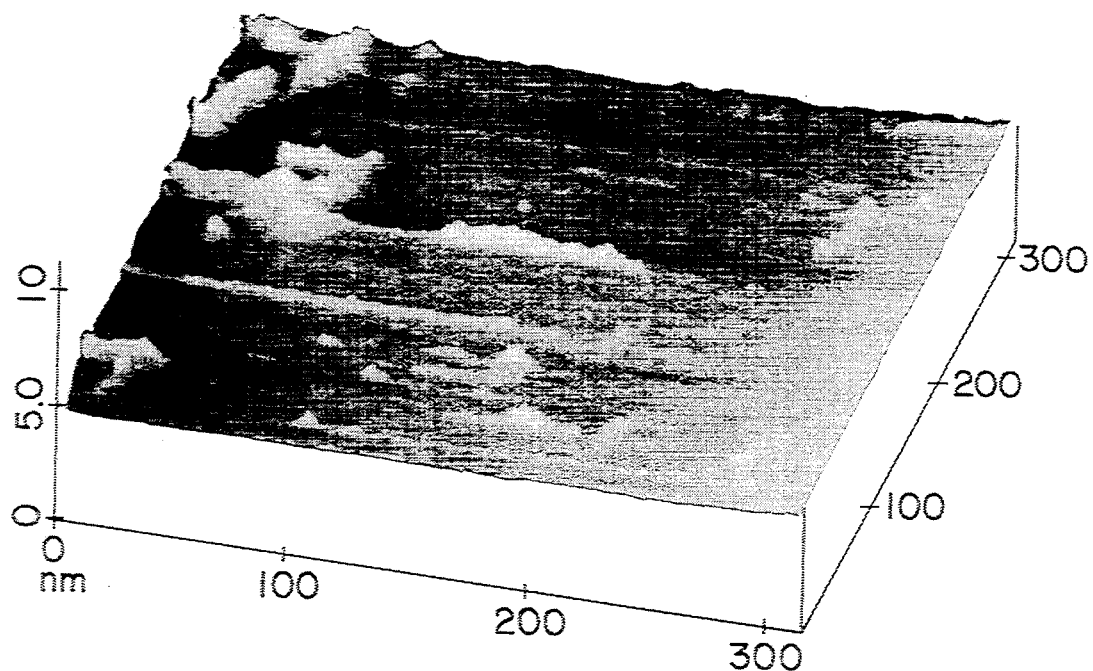

FIG. 26—Atomic force microscopy image of a Mica-Nickel with XCEM 449. 5 μl of 1 mM Nickel chloride was spotted on a freshly cleaved mica surface, allowed to sit for 1 minute, and rinsed with Milli-Q ® water. This was air-dried at room temperature for 20 minutes, and attached to a fluid cell. 100 μl of 0.5 μg/ml of XCEM 449 antibody was injected into the fluid cell for 10 minutes and then flushed with PBS. Images were made under PBS using the 12 micrometer scanner head and a 100 micrometer cantilever. The force was approximately $10^{-8}$ Newtons.

Figure 27:
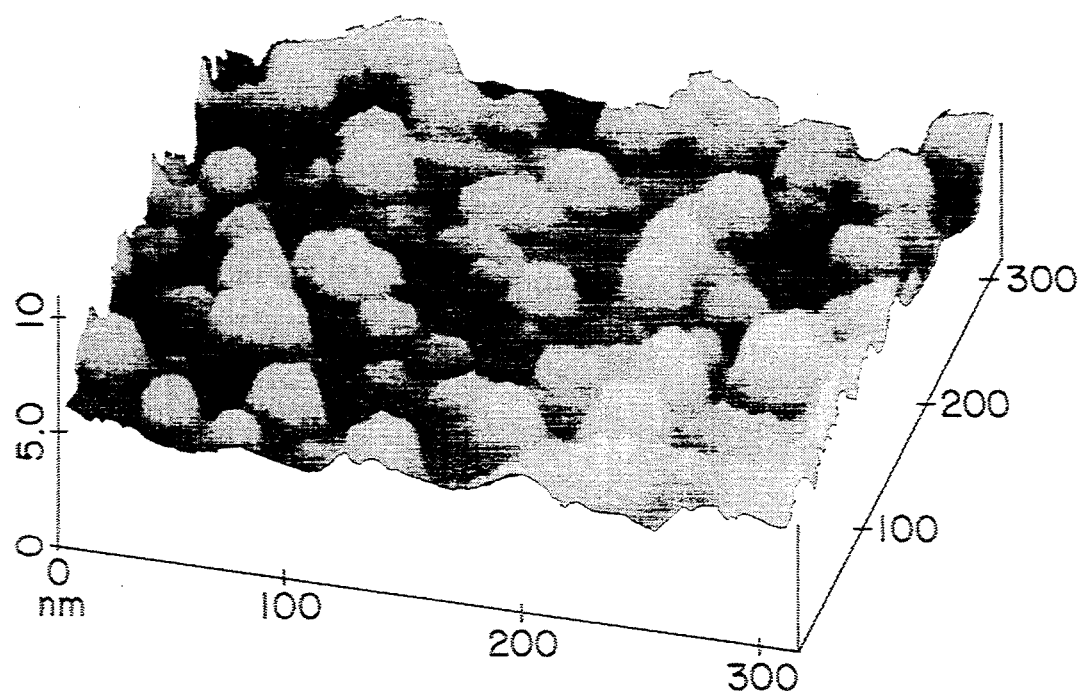

FIG. 27—Atomic force microscopy image of a nickel impregnated mica surface exposed to CHEL 13. 5 μl of 1 mM nickel chloride spotted on a freshly cleaved mica surface, allowed to sit for 1 minute, and rinsed with Milli-Q ® water. This was air-dried at room temperature for 20 minutes and attached to the fluid cell. 100 μl of 0.5 μg/ml of CHEL 13 was injected into the fluid cell and allowed to be in contact with the nickel impregnated mica surface for 10 minutes. The fluid cell was then flushed with PBS and imaged under PBS using a 12 micrometer scanner head and a 100 micrometer cantilever. The force was approximately $10^{-8}$ Newtons.

Figure 28:
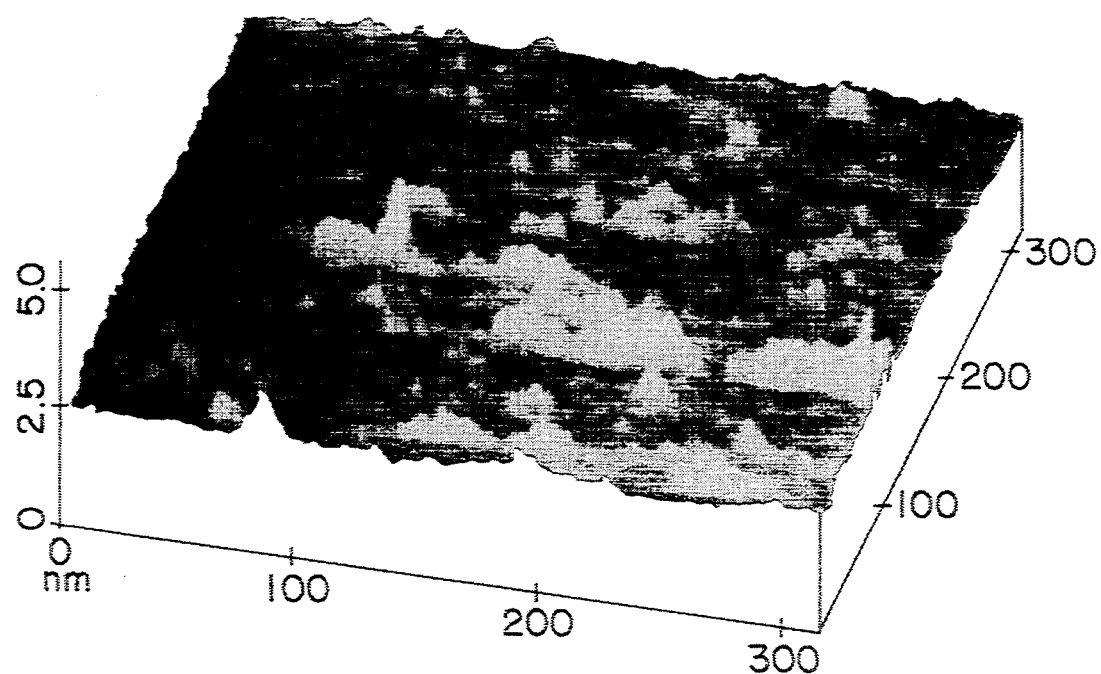

FIG. 28—Atomic force microscopy image of the nickel impregnated mica surface exposed to CHEL 13 containing bound nickel. 5 μl of 1 mM nickel chloride was spotted on a freshly cleaved mica surface, allowed to sit for 1 minute, and rinsed with Milli-Q ® water. This is air dried at room temperature for 20 minutes, and attached to the fluid cell. 180 μl of CHEL 13(0.5 μg/ml) was pre-incubated for 30 minutes with 20 μl of nickel chloride (10 mM). 100 μl of this material was injected into the fluid cell and incubated for 10 minutes with the Nickel-mica surface. The fluid cell was then flushed with PBS and imaged under PBS, using a 12 micrometer scanner head and a 100 micrometer cantilever. The force was approximately $10^{-9}$ Newtons.

DEFINITIONS

Ala—the amino acid alanine

Analog—a compound which is functionally similar to another yet possesses a different structure.

Anti-oncogene—a tumor-suppressing gene involved in controlling cellular growth. Inactivation of this type of gene leads to deregulated cellular proliferation as in cancer.

Anti-oncoprotein—a polypeptide which regulates cell growth encoded by an anti-oncogene.

Arg—the amino acid arginine.

Asn—the amino acid asparagine.

Asp—the amino acid aspartic acid.

Base pair (bp)—refers to DNA or RNA. The abbreviations A,C,G, and T correspond to the 5'-monophosphate forms of the nucleotides (deoxy)adenine, (deoxy)cytidine, (deoxy)guanine, and (deoxy)thymine, respectively, when they occur in DNA molecules. The abbreviations U,C,G, and T correspond to the 5'-monophosphate forms of the nucleosides uracil, cytidine, guanine, and thymine, respectively when they occur in RNA molecules. In double stranded DNA, base pair may refer to a partnership of A with T or C with G. In a DNA/RNA heteroduplex, base pair may refer to a partnership of T with U or C with G.

Biologically Active Molecule (BAM)—refers to compounds chosen from the group consisting of IPs, proteins, nucleotides, lipids, carbohydrates, enzymes, drugs and cofactors.

CHEL 13—The XCEM 449 antibody (Beidler, et al. (1988) J. Immunology 141:453–460 herein incorporated by reference) modified to incorporate a chelating peptide at the carboxy terminus of the heavy chain.

Chelating Peptide (CP)—an amino acid sequence capable of complexing with a metal ion having multiple coordination sites. The presence of the CP designation when associated with another molecule, such as "CP-enzyme", indicates that the molecule is covalently linked to a chelating peptide.

Chelator—an organic chelating agent or chelating peptide

CP-E7—a fusion protein comprising the amino acid sequence of the E7 oncoprotein or a functional derivative thereof covalently bound to a chelating peptide.

CP-Immobilized Metal Ion Affinity Chromatography (CP-IMAC) —a method of linking a fusion protein containing a chelating peptide or a free chelating peptide to a Solid Support where this Solid Support possesses a coordinately complexed metal ion as described in U.S. Pat. No. 4,569,794, the entire teaching of which is hereby incorporated by reference.

CP-RB—a fusion protein comprising the amino acid sequence of the RB anti-oncoprotein or a functional derivative thereof covalently bound to a chelating peptide.

CP-protein—a protein comprising an amino acid sequence of a protein directly or indirectly covalently bound to a chelating peptide.

CP-molecule—a hybrid molecule comprising the amino acid sequence of a chelating peptide directly or indirectly covalently bound to a molecule.

Cys—the amino acid cysteine or one-half of a cystine residue covalently linked via a disulfide bridge to another one-half cystine residue.

DNA—Deoxyribonucleic acid.

E7—an oncoprotein derived from the E7 gene of the human papillomavirus genome or a functional derivative thereof.

EDTA—an abbreviation for ethylenediamine tetraacetic acid.

Functional analog—refers to a molecule having similar functional properties but a modified structure relative to the naturally occurring form of that molecule or compound. A functional analog includes fragments of or additions to the parent molecule which have similar functional properties and reactivities as the parent molecule.

Fusion Protein—refers to a polypeptide which comprises the amalgamation of two amino acid sequences derived from heterogeneous sources.

Fusion Oncoprotein—a fusion protein wherein one amino acid sequence comprises the amino acid sequence of an oncoprotein.

Gln—the amino acid glutamine.

Glu—the amino acid glutamic acid.

Gly—the amino acid glycine.

His—the amino acid histidine.

IDA—an abbreviation for iminodiacetic acid.

IMAC—an abbreviation for immobilized metal ion affinity chromatography.

Immunoreactive Protein(s) (IP)—a term used to collectively describe antibodies, fragments of antibodies (such as but not limited to Fab, Fab', $Fab_2'$, and Fv fragments), and chimeric, humanized, or CDR-grafted antibodies capable of binding antigens of a similar nature as the parent antibody molecule from which they are derived, and "single chain polypeptide binding molecules" as described in PCT Application No. PCT/US 87/02208, International Publication No. WO 88/01649, International Publication Date: 10 Mar. 1988, the entire teaching of which is hereby incorporated by reference. IPS includes MAB 35 as described by Jean Pierre Mach and associates, CHA 255, CEM231, and XCEM449 (Beidler, et al.).

Ile—the amino acid isoleucine.

Leu—the amino acid leucine

Lys—the amino acid lysine.

Met—the amino acid methionine.

Milli-Q ® water—water purified through the Milli-Q ® filtration system available from Millipore Corporation, Ashby Road, Bedford, Mass. 01730.

mRNA—messenger RNA.

MWCO—an abbreviation for molecular weight cut-off.

Oncogene—a gene which encodes an oncoprotein.

Oncoprotein—a polypeptide encoded by an oncogene that affects the normal metabolic control and metabolism of a cell in such a way that it is neoplastically transformed.

Organic Chelating Agent—bidentate, tridentate, quadridentate, tripod, and macrocyclic ligands such as iminodiacetic acid, nitrilotriacetic acid, terpyridine, bipyridine, triethylenetetraamine, biethylene triamine.

Orn—the amino acid ornithine.

PBS—an abbreviation for phosphate-buffered saline

Phe—the amino acid phenylalanine.

Plasmid—an extrachromosomal self-replicating genetic element.

PMSF—an abbreviation for phenylmethylsulfonyl fluoride.

Pro—the amino acid proline.

RB protein—an anti-oncoprotein derived from the human retinoblastoma gene comprising the DNA sequence as disclosed in Friend, S.H., et al., (1987) P.N.A.S.-U.S.A. 84: 9059–9063 or a functional derivative thereof.

Reading frame—the nucleotide sequence from which translation occurs "read" in triplets by the translational apparatus of tRNA, ribosomes and associated factors, each triplet corresponding to a particular amino acid. Because each triplet is distinct and of the same length, the coding sequence must be a multiple of three. A base pair insertion or deletion (termed a frameshift mutation) may result in two different proteins being coded for by the same DNA segment. To insure against this, the triplet codons corresponding to the desired polypeptide must be aligned in multiples of three from the initiation codon, i.e. the correct "reading frame" must be maintained. In the creation of fusion proteins containing a chelating peptide, the reading frame of the DNA sequence encoding the structural protein must be maintained in the DNA sequence encoding the chelating peptide.

Recombinant DNA Cloning Vector—any autonomously replicating agent including, but not limited to, plasmids and phages, comprising a DNA molecule to which one or more additional DNA segments can or have been added.

Recombinant DNA Expression Vector—any recombinant DNA cloning vector in which a promoter has been incorporated.

Replicon—A DNA sequence that controls and allows for autonomous replication of a plasmid or other vector.

Reporter molecule (or reporter group)—refers to compounds commonly used in diagnostic applications such as visual dyes, fluorescent chelating agents, radioactive compounds, and other compounds which possess photometrically useful properties RNA—ribonucleic acid.

RP-HPLC—an abbreviation for reversed-phase high pressure liquid chromatography.

Ser—the amino acid serine.

Single Polypeptide Chain Binding Molecule—a polypeptide possessing immunological specificity as described in PCT International Patent Application number PCT/US87/02208 published Mar. 10, 1988 under International Publication Number WO 88/01649.

Solid Support—An insoluble natural or synthetic polymer in the form of a porous membrane, bead, microparticle, chromatographic resin, microtiter plate, mica, and the like.

Spacer—refers a polypeptide, protein, polysaccharide, polynucleotide or a synthetic organic moiety composed of from 1 to 50 monomer units Thr—the amino acid threonine.

Transcription—the process whereby information contained in a nucleotide sequence of DNA is transferred to a complementary RNA sequence.

Translation—the process whereby the genetic information of messenger RNA is used to specify and direct the synthesis of a polypeptide chain.

Tris—an abbreviation for tris(hydroxymethyl)aminomethane.

Trp—the amino acid tryptophan.

Tyr—the amino acid tyrosine.

Val—the amino acid valine.

Vector—a replicon used for gene manipulation bearing polynucleotide sequences corresponding to appropriate protein molecules which, when combined with appropriate control sequences, confers specific properties on the host cell to be transformed. Plasmids, viruses, and bacteriophages are suitable vectors, since they are replicons in their own right. Artificial vectors are constructed by cutting and joining DNA molecules from different sources using restriction enzymes and ligases. Vectors include Recombinant DNA cloning vectors and Recombinant DNA expression vectors. When vectors are introduced to bacterial cells the process is termed transformation. The analogous process in eucaryotic cells is termed transfection.

X-gal—an abbreviation for 5-bromo-4-chloro-3-indolyl beta-D-galactoside.

DETAILED DESCRIPTION OF THE INVENTION

The instant invention provides a method for preparing a kinetically inert transition metal complex with 2 or more of the same or different chelating agents wherein said chelating agents are covalently linked to a Biologically Active Molecule, a reporter molecule, or to a Solid Support, said method comprising the steps of:
a.) preparing a kinetically labile transition metal complex with a transition metal and 2 or more of the same or different of said chelating agents, and
b.) changing the oxidation state of said metal ion to form the kinetically inert transition metal complex.

There is a substantial advantage to forming a complex between the molecules containing the metal binding moieties while the metal ion is in a labile oxidation state rather than simply using the metal ion in its kinetically inert oxidation state initially: the direct formation of a complex between the metal ion in its inert oxidation state and the molecules containing a chelating peptide would be too slow as to have any practical utility. One advantage to the kinetically inert metal ion crosslinkage over covalent crosslinking methods is that the crosslinkage can be made labile again by the addition of the appropriate redox reagent. The potential reversibility of the linkage offers distinct advantages for the analysis of solid phase-immobilized proteins as well as the opportunity to recycle those reagents bound to a matrix. The invention provides compounds of the formula:

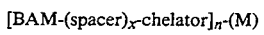

[BAM-(spacer)$_x$-chelator]$_n$-(M)

wherein:
"spacer" is a polypeptide, protein, polysaccharide, polynucleotide or a synthetic organic moiety composed of from 1 to 50 monomer units
"chelator" is an organic chelating agent or chelating peptide,
"M" is a transition metal ion capable of forming a kinetically inert transition metal ion complex and M is in a kinetically inert oxidation state,
n=1 to 4
x=0 or 1, and,
wherein each [BAM-(spacer)$_x$-chelator] is the same or different.

The invention further provides compounds of the formula:

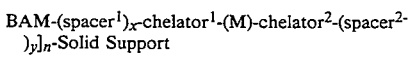

BAM-(spacer$^1$)$_x$-chelator$^1$-(M)-chelator$^2$-(spacer$^2$)$_y$]$_n$-Solid Support wherein:
wherein:
"BAM" is a Biologically Active Molecule or reporter group,
"spacer" is a polypeptide, protein, polysaccharide, polynucleotide or a synthetic organic moiety composed of from 1 to 50 monomer units, "chelator" is an organic chelating agent or chelating peptide, "M" is a transition metal ion capable of forming a kinetically inert transition metal ion complex and M is in a kinetically inert oxidation state.

x = 0 or 1, y = 0 or 1, n = number of units bound to the Solid Support.

In the preferred practice of the invention, the nucleus is a Solid Support as defined herein. Furthermore nucleus indicates a polypeptide, polynucleotide, protein or polysaccharide or a synthetic organic moiety composed from one to 50 monomer units wherein said nucleus has at least 2 chelators covalently bound to it.

The invention further provides heterogeneous or homogeneous transition metal ion polymers wherein each transition metal ion complex monomer is a group of the formula:

[(M)-chelator$^1$-(spacer$^1$)$_x$-BAM-(spacer$^2$)$_y$-chelator$^2$-]$_n$ wherein:

"BAM" is a Biologically Active Molecule or reporter group,

"spacer" is a polypeptide, protein, polysaccharide, polynucleotide or a synthetic organic moiety composed of from 1 to 50 monomer units, "chelator" is an organic chelating agent or chelating peptide, "M" is a transition metal ion capable of forming a kinetically inert transition metal ion complex and M is in a kinetically inert oxidation state.

and in each monomer unit, spacer$^1$ and spacer$^2$ are the same or different, chelator$^1$ and chelator$^2$ are the same or different, x = 0 or 1 y = 0 or 1 and n = 1 to 10$^6$.

Transition metal ions useful in the above compounds of the invention include V(II), Cr(III), Mn(IV), Fe(II), Ir(III), Ru(II), Os(II), Co(III), Rh(III), Pd(IV), or Pt(IV). In the preferred practice of the invention, the transition metal ion is selected from the group comprising Cr(III), Ru(II), or Co(III). In the most preferred practice of the invention as exemplified herein the transition metal ion is Co(III).

The term chelator as used in the description of the above compounds refers to an organic chelating agent selected from the group comprising bidentate, tridentate, quadridentate, tripod, and macrocyclic ligands. In the preferred practice of the invention at least one of said chelators is an organic chelating agent selected from the group comprising iminodiacetic acid, nitrilotriacetic acid, terpyridine, bipyridine, triethylenetetraamine, biethylene triamine and derivatives thereof. In the most preferred practice of the invention, as exemplified herein, at least one of said chelators is iminodiacetic acid.

It is also permissible in compounds of the above formulae that at least one of said chelators is a chelating peptide of the formula.:

(His)$_x$-(A)$_y$-(His)$_z$ wherein A is one or more amino acids, x = 1 − 10, y = 0 − 4, z = 1 − 10, and monomers, dimers, and trimers thereof wherein each monomer unit of said dimers or trimers is the same or different.

In the preferred practice of the invention, x = 1 − 3, y = 0 − 4, z = 1 − 3. In a further preferred practice of the invention said chelating peptide is selected from chelating peptides of the formula His-Trp-His-Met-Tyr, His-His-His-Met-Tyr, His-Trp-His-Trp-His, His-Trp-His-His, His-His-His-His-Tyr-Met-His-His-His-Tyr, His-Trp-His-His-His-Pro, His-His-His-His-His, His-Gly-His-Gly-Gly-Gly-His-Gty-His, and His-Gly-His-Gly-Gly-Gly-Gly-Gly-His-Gly-His. In the most preferred practice of the invention as exemplified herein, the chelating peptide comprises the formula His-Trp-His-His-His.

A variety of compounds may be incorporated into structures as a Biologically Active Molecule or reporter group. These Biologically Active Molecules and reporter groups are selected from the group comprising proteins, enzymes, drugs, fluorescent dyes, radioactive ligands, nucleotides, IPs, carbohydrates, or lipids. In further preferred compounds of the invention, at least one of said IPs is a protein. In further preferred compounds of the invention, at least one of said IPs is an enzyme. In further preferred compounds of the invention, at least one of said Biologically Active Molecules is an IP. In further preferred compounds of the invention, at least one of said Biologically Active Molecules is an antibody. In further preferred compounds of the invention, at least one of said IPs is an Fab, Fab' or Fv molecule. In further preferred compounds of the invention, at least one of said Biologically Active Molecules is a chimetic, humanized, or CDR-grafted antibody.

The instant invention further provides a method for purifying and immobilizing proteins by the synthesis of a kinetically inert transition metal ion complex between a chelating agent, wherein said chelating agent is covalently linked to a Biologically Active Molecule or reporter molecule, and a transition metal ion wherein said transition metal ion is immobilized on a Solid Support said method comprising the steps of:

a.) preparing a kinetically labile transition metal complex between the chelating agent which is attached to the Biologically Active Molecule or reporter molecule and said transition metal ion wherein said transition metal ion is immobilized on a Solid Support and said transition metal ion is in a kinetically labile oxidation state, and.

b.) changing the oxidation state of said metal ion to a kinetically inert oxidation state.

Subsequently the column may be used in an affinity binding assay. The principles and practice of the CP-IMAC purification procedure are provided in Smith, M.C. and Pidgeon, C. U.S. Pat. No. 4,569,794, issued Feb. 11, 1986, the entire teaching of which is hereby incorporated by reference.

Regarding the "kinetically inert complex" formed in the method, a distinction must be made between the terms "inert" and "stable" The term "inert" refers to the degree of lability. Lability refers to the ability of a particular complexed ion to engage in reactions that result in replacing one or more ligands in its coordination sphere by others. In an aqueous environment, the unoccupied [resin-chelator-$M^{n+}$] coordination positions are occupied by water molecules where M is a transition metal ion and n is the oxidation number. These water molecules must be displaced by the chelating peptide or organic chelating agent in order to form the [resin-chelator-Co(II)-chelator-protein] complex. When such reactions occur rapidly, the reaction is termed "labile". However, where such reactions occur very slowly or not at all, the complex is said to be kinetically "inert". Kinetic lability or inertness is related to the reaction rate and are not to be confused with thermodynamic stability or instability. Stability refers to the thermodynamic tendency of a species to exist under equilibrium conditions. Cotton and Wilkinson illustrate the point stating:

A simple example of this [labile vs. stable] distinction is provided by the $[Co(NH_3)_6]^{3+}$ ion which will persist for days in an acid medium because of its kinetic inertness or lack of lability despite the fact that it is thermodynamically unstable, as the following equilibrium constant shows:

$$[Co(NH_3)_6]^{3+} + 6H_3O^+ = [Co(H_2O)_6]^{3+} + 6NH_4^+ \quad K = 10^{25}$$

In contrast, the stability of $[Ni(CN)_4]^{2-}$ is extremely high:

$$[Ni(CN)_4]^{2-} = Ni^{2+} + 4CN^- \quad K = 10^{-22}$$

but the rate of exchange of $CN^-$ ions with isotopically labelled cyanide ion added to the solution is immeasurably fast by ordinary techniques. *Advanced Inorganic Chemistry*, Cotton, F.A. and Wilkinson, G. (1972) 3rd ed. Interscience Publishers, p.652.

Thus, the formation of the kinetically inert (molecule-chelator)-metal ion-(chelator-molecule) complex assures the effective linkage of the two molecules for periods of time ranging from days to years.

This metal binding moiety may be a chelating peptide or an organic chelating agent. Examples of such organic chelating agents include bidentate, tridentate, and quadridentate ligands such as iminodiacetic acid (IDA), nitrilotriacetic acid (NTA), terpyridine, bipyridine, triethylenetetraamine, biethylenetriamine and tripod ligands such as the polypyrazolyl borate ligands, and macrocyclic ligands such as 1,4,7 triazacyclononane, dimethylglyoxime, phenanthroline, diphenylglyoxime, and the like. Subsequent change of the metal ion oxidation state from a kinetically labile to a kinetically inert oxidation state will result in the formation of an inert complex between the molecules and the metal ion.

A variety of chelating peptides may be employed which will form a complex with an immobilized metal ion. Such chelating peptides are represented by the formula:

$$His)_x-(A)_y-(His)_z$$

where A is an amino acid, $x = 1-10$, $y = 0-4$, $z = 1-10$, and polymers thereof wherein each monomer unit of said polymer is the same or different.

In the preferred practice of the invention, the chelating peptide may be from 2 to 10 amino acids in length containing from at least one, and preferably 2 or more, histidine residues. In the preferred practice of the invention A is selected from the group comprising Trp, Gly, or Tyr. Those chelating peptides most preferred in the practice of the instant invention are shown in Table I below:

TABLE I

| letter designation | Chelating Peptides amino acid sequence |
|---|---|
| a) | His—Trp—His—Met—Tyr (Seq. ID #1) |
| b) | His—His—His—Met—Tyr (Seq. ID #2) |
| c) | His—His—His—His—Tyr (Seq. ID #3) |
| d) | His—Trp—His—Trp—His (Seq. ID #4) |
| e) | His—Trp—His—His—His (Seq. ID #5) |
| f) | His—His—His—His—Tyr—Met—His—His—His—Tyr (Seq. ID #6) |
| g) | His—His—His—His—His (Seq. ID #7) |
| h) | His—Trp—His—His—His—Pro (Seq. ID #8) |
| i) | His—Gly—His—Gly—Gly—Gly—His—Gly—His (Seq. ID #9) |
| j) | His—Gly—His—Gly—Gly—Gly—Gly—Gly—Gly—His—Gly—His (Seq. ID #10) |

It is permissible to have an N-terminal methionine residue, characteristic of recombinant proteins, and still retain the functional aspects of the chelating peptide sequences shown above. Furthermore, it is permissible to have from 1 to approximately 12 amino acids between the N-terminus of the CP-protein and the chelating peptide and retain the metal binding properties of the chelating peptide. It has been found that more than 6 amino acids may be placed at the amino terminus of some CP-RB constructs. The determination of how may amino acids may be placed between the chelating peptide and the structural protein is dependent on the properties of the structural protein. Accordingly, the peptide spacer should not be so large as to interfere with the physical characteristics of the structural protein. It is also permissible to have from 1 to approximately 12 amino acids following the chelating peptide when the chelating peptide is located at the C-terminus of the protein. It is also permissible to incorporate the chelating peptide into the primary structure of the protein so that it is surface exposed and capable of complexing with a metal ion.

A variety of metal ions may be incorporated into the practice of the instant invention. Octahedral complexes with filled ($d^6$) or half-filled ($d^3$) levels such as Cr(III), V(II), Mn(IV) and the low spin forms of Co(III), Fe(II), Ru(II), Os(II), Rh(III), Ir(III), Pd(IV) and Pt(IV) tend to be extremely inert and useful in the practice of the instant invention. Hanzik, Robert P. in *Inorganic Aspects of Biological and Organic Chemistry*, Academic Press, New York, 1976, P. 109. See also Cotton, F. A. and Wilkinson, G. supra. Those of ordinary skill in the art will appreciate the parameters involved in incorporating these metal ions into the practice of the instant invention. In the preferred practice of the invention the metal ion is selected from the group comprising Co, Cr, and Ru. In the most preferred practice of the invention the metal ion is Co. In the most preferred practice of the invention it is desirable to proceed from Co(II), Cr(II), or Ru(III) to Co(III), Cr(III), or Ru(II) respectively to form the inert complex. The metal ions Zn, Cu, or Ni are useful for purification purposes but do not appear to afford complexes as inert as those provided with the preferred metal ions, such as cobaltic ion.

Certain metal ions are more preferred for use with any particular chelating agent. In general, for the purposes of this invention, hard metal ions should be complexed with harder ligands and soft metal ions should be complexed with soft ligands. For example, when the chelating agent employed is iminodiacetic acid (IDA) preferred metal ions include Cr(III), V(II), Mn(IV), Co(III), Fe(II), Ru(II) and Pt(IV). When the chelating agent employed is nitrilotriacetic acid (NTA preferred metal ions include Cr(III), V(II), Mn(IV), Co(III), Fe(II), Ru(II) and Pt(IV). When the chelating agent employed is terpyridine, bipyridine, or polypyrazolyl borate ligands, preferred metal ions include Co(III), Fe(II), Ru(II), Os(II), Rh(III), Ir(III), Pd(IV) and Pt(IV). When the chelating agent employed is triethylenetetraamine, biethylenetetraamine, or 1,4,7-triazacyclonane, preferred metal ions include Co(III), Cr(III), Fe(II), Ru(II), Os(II), Rh(III), Ir(III), Pd(IV) and Pt(Iv).

Producing the necessary change in the oxidation state of the metal ion may be achieved by a variety of redox reagents. For example oxidizing agents such as oxygen, hydrogen peroxide, and peracids may be used in the practice of the invention. Examples of reducing agents include thiols, potassium ferrocyanide, potassium thiocyanate, sulfites, and sodium dithionite. These will be prepared in aqueous solutions of appropriate concentrations.

It will be recognized by those skilled in the art that not all redox reagents will be appropriate to change the oxidation state of these metal ions under all conditions so as to form kinetically inert complexes with the chelating agents provided. One factor in selecting the appropriate redox reagent is to take into consideration the electrochemical potential of the labile complex and use a reagent such that the overall free energy is such that reaction is spontaneous. It will also be recognized by those skilled in the art that not all redox reagents would be appropriate depending on the nature of the molecules to be crosslinked. The susceptibility of proteins or reporter molecules to inactivation by certain redox reagents must be considered as well.

The technique provided herein provides a broadly applicable method for crosslinking molecules to form homodimeric, hetero-dimeric, homo-multimeric, or heteromultimeric complexes. The chelating peptide or organic chelating agent may be coupled to a multitude of molecules such as drugs, fluorescent dyes, radioactive ligands, nucleotides, proteins, IPs, carbohydrates, lipids, or enzymes by chemical means well known in the art. For example, see Means, G.E. and Feeney, R.E., *Chemical Modifications of Proteins*, Holden Day, San Francisco, 1971. The second molecule in the pair may have the metal ion bound through the use of a chelating peptide or other multidentate metal binding moiety. Alternatively, these multidentate ligands may be attached to other molecules such as drugs, fluorescent dyes, radioactive ligands, nucleotides, proteins, IPs, carbohydrates, lipids, or enzymes by chemical means well known in the art.

For instance, in the practice of the method of this invention, chelating peptides may be incorporated into the primary structure of a protein so as to provide the metal chelating moiety. Such proteins are termed CP-proteins. Virtually any protein may be incorporated into a CP-protein form. The chelating peptide domain of the CP-protein will bind to an immobilized metal ion, metal ion CP-protein complex, or free metal ion resulting in the CP-protein being bound to the support, a CP-protein/metal ion complex, or a metal ion respectively. The metal ion may also be immobilized on a Solid Support or free in solution. The metal ion may also be attached to another molecule possessing a metal binding moiety, thereby allowing the formation of homo-dimeric and hetero-dimeric forms of the CP-molecule.

CP-proteins may be formed by a variety of methods. CP-proteins may be produced either by recombinant DNA technology or well known chemical procedures, such as solution or solid-phase peptide synthesis, or semisynthesis in solution beginning with protein fragments coupled through conventional solution methods. In the preferred practice of the invention, CP-proteins are produced through the use of recombinant DNA technology by the addition of an in-frame DNA sequence encoding a chelating peptide into the coding sequence of the protein of interest. Incorporation of the chelating peptide coding sequence may be achieved by conventional genetic cloning techniques or by the use of the Polymerase Chain Reaction (PCR) to create and amplify the synthetic gene encoding the CP-protein. Synthetic PCR primers may be created which contain the coding sequence of the chelating peptide thereby directly incorporating the chelating peptide coding sequence into the DNA produced via PCR. The expression products of such coding sequences are "CP-proteins" which possess a chelating peptide.

The placement of the chelating peptide in the ultimate CP-protein is largely dictated by the properties of the protein. The chelating peptide coding sequence may be incorporated into the protein coding sequence at or near either the 5' or 3' ends or the protein coding sequence such that the chelating peptide will occur at or near either the amino or carboxyl terminus of the protein. Furthermore, the chelating peptide may be incorporated into the primary structure of a protein so that it is surface exposed and is capable of complexing with a metal ion. In all circumstances, it is preferred that the chelating peptide should be incorporated into the protein so as to minimize any potential effect on the biological properties of the protein. In some instances, such as where steric hindrance may interfere with the binding of the chelating peptide to the metal ion thereby preventing immobilization, it may be desirable to provide some "spacer" between the chelating peptide and the protein sought to be immobilized. Such "spacers" would include peptides of from 1 to approximately 30 amino acids. Chelating peptides may also be linked to proteins through organic linkers of varying length to provide the desired spacing effect. The inclusion of a polypeptide spacer is readily achieved when the CP-protein is produced via recombinant DNA technology by insertion a DNA sequence encoding the desired polypeptide spacer (preserving the proper reading frame of the chelating peptide and protein molecules) between the DNA sequences encoding the chelating peptide and the protein sought to be immobilized.

It is useful in some applications to engineer a linkage between the chelating peptide and the protein to provide a specific proteolytic cleavage point between the chelating peptide and the protein. Proteolysis may be achieved by enzymatic (e.g., trypsin, chymotrypsin) or chemical (e.g., cyanogen bromide) means. Furthermore, the incorporation of a proline residue at an even numbered position from the N-terminus of the CP-protein facilitates removal of the chelating peptide through the action of DAP-I (diaminopeptidase), provided the CP sequence does not contain a proline.

Such CP-proteins may be conjugated to a wide variety of other CP-proteins and other non-proteinaceous compounds possessing metal binding moieties. For example, by using two identical proteins, each possessing a chelating peptide sequence, a kinetically inert linkage may be created between these CP-proteins wherein the inert form of the metal ion acts as a bridge between the proteins via the intercession of the chelating peptides resulting in the formation of a homo-dimer. Similarly, if the proteins are not the same, heterogeneous complexes may be formed in a similar manner. For example, two different IPs each possessing a chelating peptide may be coupled through the metal ion. The resultant compound would function as a bifunctional antibody. For example, two different IPs each possessing a chelating peptide, one of which has specificity to a tumor cell surface antigen and the second possesses specificity for an imaging reagent may be coupled through the metal ion and would be useful in the diagnosis and localization of tumors. Furthermore, chelating peptides may also be attached to the carboxy termini of the heavy chains of an antibody resulting in the formation of an Ab-(CP)$_2$ molecule. The chelating peptides of the antibody could then be used to couple the antibody to another CP-molecule such as a CP-fluorescent dye, a CP-drug, a CP-enzyme, a CP-radioactive ligand, CP-carbohydrate, or a CP-imaging reagent.

Alternatively, the inert metal complex could be formed using a linker functionality with two or more metal complexing groups. The metal complexing groups could be organic, chelating agents, or chelating peptides as those terms are defined above, or a mixture of the two. For instance, such complexes amy be represented in a schematic fashion as:

1) [BAM-(spacer)-chelator]$_n$-(M)-chelator-linker
2) [BAM-(spacer)-chelator-(M)-chelator-(spacer)]-linker
3) [(M)-chelator-(spacer)-BAM-(spacer)-chelator-]

In the above formulas 1,2, and 3, "BAM" is a Biologically Active Molecule or reporter group, "spacer" is a polypeptide, protein, polysaccharide, polynucleotide or a synthetic organic moiety composed of from 1 to 50 monomer units, "chelator" is transition metal ion chelating moiety capable of binding to one or more coordination sites of a transition metal ion, "M" is a transition metal ion capable of forming a kinetically inert transition metal ion complex and M is in a kinetically inert oxidation state. Furthermore, in formula 3 above, each [BAM-(spacer)$_x$-chelator]monomer is the same or different. It is preferred that from 5 to 50 monomer units (e.g., amino acids, hexoses, penroses, nucleotides, methylene groups, methine groups, acrylic acid residues, etc.) be used in the linker molecule. As demonstrated in formula 3) above, chelating functions do not have to be at the ends of the linker molecule. Finally, note that in the above formulas, a reporter molecule may be substituted for all but one of the Biologically Active Molecules.

The instant invention also provides an assay system said assay system comprising the steps of:

a) forming a kinetically inert complex between a protein possesing a chelator and a Solid Support possessing a transition metal ion, b) exposing said kinetically inert complex to a solution containing a potential inhibitor of the ligand-protein complex,
c) introducing the ligand,
d) removing non-specifically bound molecules, and
e) quantifying the concentration of ligand and potential inhibitor in the eluent.

This assay system facilitates the study of interactions of an immobilized CP-protein or protein immobilized via a organic chelating agent with various potential ligands. In the preferred practice of the invention, the protein with which one wishes to study the interaction of secondary molecules is produced in CP-protein form as outlined above. An IMAC column is prepared in substantial accordance with the teaching of Smith, et al., U.S. Pat. No. 4,569,794 referred to previously and incorporated by reference. Care must be taken when using many metal ions to avoid the presence or introduction of redox agents to the column matrix. The immobilized metal ion must be in the labile oxidation state. A solution containing the CP-protein is introduced to the IMAC column. When one has achieved the linkage of the CP-protein to the immobilized metal ion while in the labile oxidation state, three alternatives are available:

(1) release the CP-protein from the bound metal ion by lowering the pH or by the addition of competitors such as imidazole (i.e., conventional CP-IMAC purification), or
(2) cleave the immobilized CP-protein by chemical or enzymatic means at an appropriate point between the structural protein and chelating peptide sequences allowing isolation of substantially pure protein while leaving the chelating peptide bound to the matrix, or
(3) "lock" the CP-protein to the column matrix by changing the oxidation state of the metal ion.

By changing the oxidation state of the bound metal ion, as referred to in alternative (3) above, it is possible to change the kinetic parameters of the [metal ion-CP-protein] complex so as to achieve a kinetically inert linkage of the chelating peptide or CP-protein to the support matrix. This CP-protein, immobilized through the kinetically inert metal ion linkage, may then be used to study the interactions between the protein, ligands, potential ligands, and compounds which may interfere with the binding of ligands to the protein.

In one embodiment of the invention as exemplified herein, the instant invention provides an assay system to study the interaction of oncoproteins and anti-oncoproteins. This allows one to rapidly screen for inhibitors of the formation of the oncoprotein/anti-oncoprotein complex. It is well known that oncoproteins serve as intracellular mediators in the neoplastic transformation of normal cells. Anti-oncoproteins inhibit, or regulate, cell proliferation. Certain oncoproteins are believed to exert their influence by binding to the anti-oncoprotein, thereby preventing the anti-oncoprotein from achieving its function and causing the cell to become cancerous. In developing anti-cancer agents, it therefore would be desirable to determine those agents which interfere with the formation of the oncoprotein/anti-oncoprotein complex. However, isolating and determining compounds with such activity by current methodology is highly inefficient. Utilization of the invention described herein provides a sensitive and rapid means to determine compounds which interfere with the formation of the oncoprotein/anti-oncoprotein complex.

Briefly the procedure of such an oncoprotein/anti-oncoprotein assay proceeds as follows. A CP-oncoprotein is isolated by conventional CP-IMAC methodology. Nonspecifically bound molecules are then liberated by the introduction of a weak competitor. A kinetically inert complex is then formed by changing the oxidation state of the bound metal ion causing the metal ion to change from a labile to a kinetically inert oxidation state. A sample of a test compound is then introduced to the reaction vessel containing the immobilized CP-oncoprotein followed by the addition of the anti-oncoprotein. Antibodies against the anti-oncoprotein are then introduced. A second fluorescently or enzymatically labelled antibody against the anti-oncoprotein antibody is then introduced. Unbound molecules are washed free after each phase. In the preferred practice of the invention, fluorescently labelled anti-oncoprotein may be used as an alternative to the primary and secondary antibodies further simplifying the assay. The mixture is then scored for fluorescence or assayed for enzymatic activity. The presence of fluorescence or enzyme activity characteristic of the labelled anti-(anti-oncoprotein antibody) antibody indicates the formation of the oncoprotein/anti-oncoprotein complex. This in turn indicates that the test compound has not disrupted the formation of the oncoprotein/anti-oncoprotein complex. The absence or diminution of florescence or enzyme activity indicates that the test compound has disrupted the formation of the oncoprotein/anti-oncoprotein complex and is therefore a potential anticancer agent. The assay system described above may also be adapted to automated procedures such as a Pandex ® (Baxter-Dade Diagnostics) system allowing for efficient high-volume screening of potential anti-cancer agents.

The assay system described above is not limited merely to the study of anti-oncoprotein/oncoprotein interactions. Virtually any protein-ligand pair is adaptable for use in this system. For example this same principle could be adapted to screen for compounds which have high affinity for the modified penicillin binding proteins found in methicillin resistant Staphylococcus. Penicillin binding proteins are essential to the antimicrobial action of many β-lactam antibiotics. Methicillin resistant microorganisms produce penicillin binding proteins which have low affinity for a broad range of conventional β-lactam antibiotics. Incorporation of penicillin binding proteins isolated from methicillin resistant strains of Staphylococcus into CP-protein form enables them to be purified and immobilized on a column facilitating a rapid assay to screen for compounds which bind to these modified penicillin binding proteins. Through this technique, the scientist is provided with an effective tool in the search for drugs useful against methicillin resistant infections.

As exemplified herein, this invention provides an assay system useful to discover agents which inhibit the binding of the human papillomavirus (HPV) E7 protein (an oncoprotein) of HPV type 16 to the product of the human retinoblastoma gene, RB protein (an anti-oncoprotein). The HPV-E7 protein is the major transforming protein of the genital human papillomaviruses. The RB protein is believed to be the product of an anti-oncogene which functions to regulate normal cell growth. The HPV-E7 oncoprotein has been shown to complex with the RB anti-oncoprotein in vitro. Dyson, N., Howley, P.M., Munger, K., Harlow, E. (1989) Science 243 934–937. Thus it is reasonable to believe that the formation of the HPV-E7/RB complex results in loss of control of normal cell growth manifested by an uncontrolled proliferation of cells causing a tumor. Consequently, compounds which inhibit the formation of the HPV-E7/RB complex would be potent antiviral or anticancer agents for HPV-induced dysplasias and malignancies. In many instances, as is the case with HPVs, it is not possible to generate transforming viruses in tissue culture. Therefore, cell culture assays for the identification of anti-viral compounds would be impossible to develop. However, it is possible to utilize cloned viral genomes transformed into *E. coli* to generate sufficient quantities of the oncoprotein for use in a cell-free assay system as demonstrated by the instant invention.

The immobilized form of the CP-E7 protein is useful for the discovery of new compounds which bind to the E7 protein and may be useful as potential therapeutic agents. For example, a nuclear extract prepared from African green monkey kidney cell line BSC-40 (provided by A. Bruskin, Applied biotechnology, Cambridge, Mass.) infected with the RB recombinant vaccinia virus, vAbT334 (Applied bioTechnology, Cambridge, Mass.) was applied to the IDA-Co(III)-CPe-E7-resin complex. Non-specifically bound proteins were washed from the IDA-Co(III)-CPe-E7-resin complex. 2-mercaptoethanol was used to change the oxidation state of the cobalt ion to the +2 state creating a kinetically labile resin-IDA-Co(II)-CPe-E7-[ bound protein] complex allowing removal of the CP-E7-[bound protein] complex. A comparison of proteins bound to a resin-IDA-Co(III)-myoglobin and the resin-IDA-Co(III)-CPe-E7 by SDS-PAGE on a Novex Trisglycine system demonstrated that at least eight proteins from the nuclear extract bind E7 specifically. The molecular weights of proteins which bind to E7 from a nuclear extract of uninfected BSC-40 cells on the Novex gel were 350 kDa, 140 kDa, 54 kDa, 46 kDa, 41 kDa, 30 kDa, 21.5 kDa, and 13.5 kDa. The molecular weights of these proteins from BSC-40 cells infected with the RB recombinant vaccinia virus vAbT334 on the Novex gel were 300 kDa, 140 kDa, 110 kDa, 46 kDa, 41 kDa, 30 kDa, 25 kDa, and 20 kDa. The proteins from a duplicate gel were transferred to ProBlot ® (Applied Biosystems, Foster City, Calif.) for amino acid sequence analysis. Sequence analysis of the 46 kDa protein gave the following N-terminal sequence, M-E-V-K-K-P-A-A-A-A-A-P-G-T-A-E-K-L-S-P-K-A-A  (Seq. ID#11)

which shares homology with rat collagen binding protein (GP46) and mouse serine protease inhibitor homolog J6. The 30 kDa protein, which has the following N-terminal sequence:

M-K-G-D-P-K-K-K-X-W  (Seq. ID#12)

shares homology with the human high mobility group protein HMG1. These proteins may be readily sequenced to design a set of degenerate probes for use in hybridization protocols to isolate DNA sequences encoding said proteins. These genes may then be incorporated into well known recombinant expression systems to allow production and isolation of such proteins. Thus, the instant invention also includes these novel E7 binding molecules.

Competition experiments with free E7 were carried out to confirm the specific binding of these nuclear proteins to the resin-IDA-Co(III)-CPe-E7 complex.

Aliquots of the precleared nuclear extract described above were added to varying amounts of free E7 (0, 100, 500, 1000, and 5000 ng) and 5 µl of resin-IDA-Co(III)-CPe-E7 complex and allowed to incubate for two hours at 4° C. with gentle rotation. The samples were centrifuged, the supernatants removed, and the resins washed twice with 1 ml of NP-40 buffer with 10 minutes of gentle rotation after adding buffer. The resin-IDA-Co(III)-CPe-E7 complexes were treated with Novex TrisGlycine SDS-PAGE 2X sample buffer, and 5 µl of β-mercaptoethanol, boiled for 5 minutes, and centrifuged for 3 minutes. The β-mercaptoethanol reduced the Co(III) to the kinetically labile Co(II) state so as to release proteins bound to the resin. The supernatants (50 µl/lane) were electrophoresed on a Novez Tris-Glycine 4–20% gel. The gels showed that the bands unique to the Co(III)-CPe-E7 resin described above can be diminished or eliminated by competition with excess free E7.

This assay is useful in the detection of inhibitors of other HPV E7 proteins. There are at least twelve HPV types which infect the human genital tract. The lesions caused by and/or with which these viruses are associated, range from benign genital warts to dysplasia to carcinoma-in-situ and invasive carcinoma. E7 proteins of HPVs 6, 11, 16, and 18 each bind to the RB protein with different affinities. Munger, K, Werness, B.A., Dyson, N., Phelps, W.C., Harlow, E., and Howley, P.M. (1989) EMBO J. 8: 4099–4105. This assay system methodology provides a useful mechanism to determine agents which prevent inactivation of the RB protein by a variety of HPV E7 oncoproteins and consequently would be useful for the discovery of agents useful in the treatment and prevention of diseases associated with these various HPVs.

Furthermore, it has been demonstrated that viral oncoproteins from a variety of DNA tumor viruses bind to the RB protein. Examples of these include the adenovirus E1A oncogene product (Whyte, P. et al. (1988) Nature 334. 124–129), the SV40 large T antigen (DeCaprio, J.A., et al. (1988) Cell 54, 275–283), and the polyomavirus large T antigen. Each of these proteins shares a region of amino acid sequence homology with HPV E7. This region of amino acid sequence homology is involved in the formation of the oncoprotein/anti-oncoprotein complex. This observation is supported by studies indicating that mutations in this region of homology prevent formation of the oncoprotein/RB complex. Munger, et al., supra., DeCaprio, et al., supra. Therefore, the instant invention provides a significant advance toward discovery of anticancer agents to those forms of cancer induced by DNA tumor viruses. Moreover, since the anti-oncoprotein appears to interact with this region of amino acid sequence homology, a synthetic structural analog of this region may also be used in this assay (in place of the full length protein itself) to discover agents which inhibit cellular transformation by a wide variety of oncogene products.

It should be noted that this invention is not limited merely to studying those agents which interact with E7 and/or RB proteins. Nearly any oncoprotein/anti-oncoprotein "pairs" can be selected and incorporated into this methodology. For example the oncoprotein HPV E6, adenovirus E1B, and or SV40 large T antigen may also be expressed as CP-proteins and bound to the matrix in substantially the same manner as described above. The anti-oncoprotein p53 is bound by each of these oncoproteins. In the preferred practice of the invention, the CP-oncoprotein is immobilized on the matrix to allow identification of an oncoprotein binding inhibitor. It is also possible to immobilize the CP-anti-oncoprotein for identification of inhibitors of oncoprotein/anti-oncoprotein interactions. In this case one would identify molecules which would bind to the anti-oncoprotein. It should be noted that this class of inhibitors also may possess the undesirable characteristic of inhibiting the normal function of the anti-oncoprotein. Clearly, this invention's utility is enhanced by its adaptability to determine inhibitors of a potentially infinite variety of oncoprotein/anti-oncoprotein interactions merely by incorporation of the desired oncoprotein into a CP-protein form either through recombinant DNA technology or by chemical synthesis.

A schematic representation of the principles of the oncoprotein/anti-oncoprotein assay system as exemplified herein is shown in FIG. 1. As exemplified herein, both the E7 oncoprotein and RB anti-oncoproteins are expressed as CP-proteins. They are produced by addition of an inframe DNA sequence encoding a chelating peptide 5' to the coding sequence for the E7 and RB proteins. The product of these coding sequences are E7 and RB CP-proteins, each possessing a chelating peptide at the amino terminus, hereinafter referred to as CP-E7 and CP-RB respectively. As exemplified herein, an iminodiacetic acid (IDA) molecule possessing a bound Co(II) ion is covalently attached to a hydrophilic resin, such as fast flow agarose or TSK-PW gel. The immobilized Co(II) ion interacts with the chelating peptide portion of the CP-E7 and CP-RB proteins linking the CP-E7 and CP-RB proteins to the column. This provides a facile method for purification of the CP-E7 and CP-RB proteins. The CP-E7 and CP-RB proteins are purified from the crude mixture by virtue of the formation of the [CP-protein/Co(II)-Resin] complex, i.e., the "unlocked" form. The RB protein may then be isolated in free form either by cleaving the fusion protein at the RB structural sequence/chelating peptide interface while still linked to the column or eluting the CP-RB protein from the gel by addition of excess imidazole and later removing the chelating peptide by chemical or enzymatic methods. If the chelating peptide does not interfere with the function of the polypeptide to which it is fused, it is not necessary to remove the chelating peptide for later use of the CP-protein.

In the case of CP-E7, the protein is "locked" to the matrix by oxidation of the bound cobalt ion from the +2 to +3 oxidation state by introducing to the column oxygen, an oxygen containing gas, or other oxidant which is capable of oxidizing the Co(II) to Co(III) but will not oxidize the CP-E7 molecule to an inactive state. In the preferred practice of the invention, this is done by the following batch process. The contents of the column containing the immobilized IDA-Co(II)-CP-E7 complex were transferred to a test tube. The space above the settled gel was replaced with the oxygen or an oxygen containing gas and then capped. The tube was continuously inverted for 24 hours to mix the oxygen containing gas with the bead containing the IDA-Co(II)-CP-E7 complex to oxidize the Co(II) to Co(III). The CP-E7-Co(III) complex thereby assumes the "locked" form.

The "locked" form of CP-E7 provides an ideal ligand for assay of those molecules which bind to E7 or for molecules which inhibit the binding of a known E7 ligand, such as RB, by addition of the E7-ligand and a potential competitor. As previously indicated, this methodology is not restricted to the E7 oncoprotein. Any protein capable of expression as a fusion protein may be immobilized on the column matrix by this method. Consequently assays for binding or enzymatic activity of such bound CP-proteins may readily be developed by methodology substantially similar to that described above.

The immobilized CP form of a protein may also be used to isolate and purify antibodies against that protein from serum said method comprising the steps of:
a) forming a kinetically inert complex between a BAM possesing a chelator and a Solid Support possessing a bound transition metal ion,
b) exposing said kinetically inert complex to a solution containing Immunoreactive Protein against said BAM,
c) removing non-specifically bound molecules, and
e) removing bound Immunoreactive Protein.

A variety of techniques are well known in the art for the generation of antibodies against known proteins. By incorporating the protein against which one desires antibodies into a CP-protein form or by the addition of an organic chelating agent and immobilizing it on a column as previously described, one may isolate the desired antibodies from serum or other solution. After elution of unbound protein from the column, the anti-CP-protein antibodies may be eluted from the column by well known procedures without removing the immobilized CP-protein itself. One thereby obtains essentially pure anti-CP-protein antibodies. A carefully controlled gradient may be used to elute different species of anti-CP-protein antibodies which either bind to the CP-protein with differing affinities or bind multiple epitopes on the CP-protein molecule. The antibody-CP-protein complex may also be removed intact by changing the oxidation state of the bound metal ion to a kinetically labile form and eluting the antibody-CP-protein complex as previously described.

For example, as demonstrated in Example 10 herein, the immobilized CPe-E7 protein was used to purify anti-E7-antibodies from rabbit sera. The production of anti-E7-antibodies was performed in substantial accordance with the teaching of Reichlin, M. (1980) Methods In Enzymology 70:159–165, herein incorporated by reference, on an immunization schedule as recommended by Hazelton Research Products, Inc., P.O. Box 7200, Denver, Pa. 17517. CPe-E7 immobilized on a Co(III)-IDA-resin (as described in Examples 1 through 4.B. herein) was used to prepare the affinity column for antibody isolation. The sera obtained from the injected rabbits was applied to the IDA-Co(III)-CPe-E7 resin complex and allowed to react for ninety (90) minutes. Unbound protein was washed from the column and the anti-E7-antibodies were removed from the column using a 0 to 100% gradient of buffer B (100 mM glycine, 7.5M urea, pH 2.5). The presence of the anti-E7-antibodies was confirmed using standard ELISA procedures and SDS-PAGE.

Assay systems developed according to the practice of the instant invention, such as the E7/RB oncoprotein-/anti-oncoprotein assay described above, are readily adaptable to automated procedures such as where the reaction vessel is the well of a multiwell Pandex ® assay plate or a microtiter plate.

To generate the CP-E7 fusion oncoprotein, the coding sequence for the E7 protein is isolated from the pHPV16 plasmid (Behringwerke, A.G., Heidelberg, Germany) which contains the HPV16 genome cloned into the BamHI site of pBR322 (Durst, et. al. 1983). A restriction site and function map of the pHPV16 plasmid is shown in FIG. 2. The pHPV16 plasmid is digested with the NcoI and NsiI restriction endonucleases to obtain the 301 base pair nucleotide sequence containing the HPV16E7 structural gene.

The E7 coding sequence is then cloned into plasmid pCZR322. A restriction site and function map of plasmid pCZR322 appears in FIG. 3. Plasmid pCZR322 contains the human growth hormone (hGH) gene cloned downstream of a thermo-inducible lambda pL promoter. The DNA sequence encoding human growth hormone (hGH) of plasmid pCZR322 is replaced with the 301-bp NsiI-NcoI fragment encoding the E7 gene. The resultant plasmid is denoted p16E7. Insertion of the E7 coding sequence into pCZR322 is facilitated by the use synthetic oligonucleotide linkers. It is readily apparent to one skilled in the art that a variety of expression plasmids may be used in the practice of the instant invention. Examples of some commercially available expression plasmids useful in the practice of the instant invention include pNH series plasmids (commercially available from Stratagene, LaJolla, Calif.), and the pKK223 series, pPL-lambda, p43J001, pDR540, and pDR720 (commercially available from Pharmacia, Piscataway, N.J.). The conditions necessary for efficient protein expression are readily available to one skilled in the art.

Plasmid pCZR322 was digested with the NdeI and BamHI restriction endonucleases to excise the hGH coding sequence. The 5.8 kb BamHI-NdeI vector fragment was isolated by agarose gel electrophoresis and then treated with calf intestinal alkaline phosphatase to remove the 5′ phosphate groups from the linearized DNA molecules according to techniques well known in the art. A protocol for this procedure appears in *Molecular Cloning: A Laboratory Manual*, Sambrook, J., Fritsch, E.F. and Maniatis, T., Cold Spring Harbor Press, 1989, pgs. 1.58–1.61. The E7 sequence isolated above, still possessing 5′ phosphate groups, is added to the dephosphorylated DNA in the presence of synthetic linkers and T4 DNA ligase. A single stranded deoxynucleotide linker having the sequence 5′-TATGCA-3′ is used to ligate the end of the vector DNA cut by the NdeI endonuclease to the end of the E7 coding sequence cut by the NsiI restriction endonuclease. A double stranded deoxynucleotide linker of the formula:

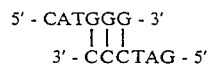

is employed to facilitate the ligation of the NcoI end of the E7 coding sequence to the BamHI end of the vector DNA. These oligonucleotide linkers may be prepared by techniques well known in the art using conventional DNA synthesizing equipment such as an Applied Biosystems Model 380A or 380B DNA synthesizer (commercially available from Applied Biosystems, Foster City, Calif.). The DNA was ligated in the presence of T4 DNA ligase. A restriction site and function map of plasmid p16E7 appears in FIG. 4. The ligation mixture was then used directly to transform competent *E. coli* DH5αF′ cells (BRL, Gaithersburg, Md.).

The sequence encoding the CP-E7 fusion oncoprotein is achieved by insertion of the DNA sequence encoding the chelating peptide 5′ to the DNA sequence encoding the E7 oncoprotein in plasmid p16E7. Synthetic oligonucleotides encoding the chelating peptides given in Table 1 which have been engineered to possess NdeI recognition sequences were purchased from Promega, Inc. (Madison, Wis.) and Indiana University School of Medicine (Indianapolis, Ind.). It is readily apparent to one of ordinary skill in the art that the DNA sequences encoding these chelating peptides may be created by synthetic methodology. Furthermore, any of the nucleotide sequences encoding these chelating peptides may be incorporated into vectors which express CP-proteins by one skilled in the art. In the preferred practice of the invention as exemplified herein, a synthetic DNA fragment encoding the Met-His-Trp-His-His-His chelating peptide, was cloned into the p16E7 plasmid utilizing the unique NdeI site of that plasmid at the 5' end of the E7 coding sequence. The resultant plasmid is denoted p16E7e reflecting the incorporation of the DNA sequence encoding the His-Trp-His-His-His chelating peptide into plasmid p16E7. A restriction site and function map of plasmid p16E7e is found in FIG. 5. Plasmid p16E7e was then transformed into competent E. coli DH5αF' cells (BRL, Gaithersburg, Md.).

The parental expression vector of plasmid pCZR322 and plasmid p16E7e contains the bacteriophage lambda pL promoter under the control of a temperature sensitive repressor. The repressor is functional at 30° C. but is non-functional at 42° C. The expression plasmid p16E7e was transformed into E. coli strain L201 cells (M. Lei, Lilly Research Laboratories). Cells were grown at 30° C. to an $OD_{600}$ of 0.6–0.8 in 2x TY broth containing 5 μg/ml tetracycline, and then induced for protein expression by growing at 42° C. for 16 hours. Cells were collected by centrifugation, lysed, and the proteins analyzed by SDS-PAGE according to the teaching of Laemmli, 1970 the entire teaching of which is hereby incorporated by reference.

The DNA sequence encoding the CP-RB proteins were created in a slightly different manner through the use of PCR. The DNA sequence encoding the human retinoblastoma gene and a truncated version thereof was amplified using PCR. The coding sequence for the RB protein was isolated from the pAbT9300 plasmid (Applied Biotechnology, Cambridge, Mass.). A restriction site and function map of the pAbT9300 plasmid is shown in FIG. 6. The nucleotide sequence corresponding to the RB gene plasmid is contained on the 4600 bp KpnI and SacI fragment of pAbT9300.

This 4600 bp KpnI-SacI fragment is too large to be expressed fully in E. coli. Consequently, two routes to the production of an RB protein for use in the assay system are available: (1) express the complete RB gene in a baculovirus expression system, or (2) subclone the 60 kd C-terminal region of the RB protein which contains the E7 binding domain (Hu, Q., Dyson, N. and Harlow, E. (1990) EMBO J. 9, 1147–1155) into plasmid pCZR322 for expression in E. coli cells. As exemplified herein, both approaches are employed. Consequently, two versions of the CP-RB fusion anti-oncoprotein are produced. These are termed CPe-RB[60] and CPe-RB. The CPe-RB[60] protein comprises the 60 kd carboxyl terminal E7 binding region of the RB protein operably linked to the His-Trp-His-His-His chelating peptide. CPe-RB refers to the entire RB protein or a functional derivative thereof operably linked to the His-Trp-His-His-His chelating peptide. As previously stated a variety of chelating peptides as provided above may also be incorporated into the practice of the invention. The DNA sequences encoding both the CPe-RB and CPe-RB[60] protein are created by the use PCR.

A description of the principles and techniques involved in the use of PCR is provided in Molecular Cloning: A Laboratory Manual, 2nd. Edition, Sambrook, A, Fritsch, E.F., and Maniatis, T. (1989) Cold Spring Harbor Press, the entire teaching of which is hereby incorporated by reference. All of the primers described for use in the PCR process may be synthesized by techniques well known in the art such as by employing an Applied Biosystems Model 380A or 380B DNA synthesizer (commercially available from Applied Biosystems, Foster City, Calif.) in substantial accordance with the directions provided by the manufacturer.

A schematic representation of the synthesis of plasmid pBlueBacRB is provided in FIG. 7. The DNA sequence encoding the CPe-RB protein is created by PCR amplification of the 2790 bp sequence of the pAbT9300 plasmid corresponding to the translated region of the RB gene. The 5'-primer used for the amplification of this 2790 bp coding sequence incorporates a sequence encoding a SpeI restriction endonuclease cleavage site, the Met-His-Trp-His-His-His amino acid sequence, and the first 20 nucleotides of the RB gene. The DNA sequence of this 48-mer 5'-primer is:

5'-GATCACTAGTATGCACTGGCATCAC-CATATGCCGCCCAAAACCCCCCG-3'     (Seq. ID#13)

The modifications to 5'-primer described above necessary to express CP-RB proteins which incorporate other chelating peptides and/or restriction enzyme cleavage sites are readily apparent to one skilled in the art.

The 3'-primer used for the amplification of the 2790 bp coding sequence incorporates a sequence encoding SpeI and BamHI restriction endonuclease cleavage sites and the DNA sequence complementary to the last 7 codons of the RB gene. The DNA sequence of this 37-mer 3'-primer is:

5'-GATCGGATCCACTAGTT-CATTTCTCTTCCTTGTTTGA-3'     (Seq. ID#14).

The DNA sequence encoding the CPe-RB protein created by the PCR is inserted into the baculovirus expression plasmid pBlueBac (commercially available from Invitrogen Corporation, San Diego, California). A restriction site and function map of plasmid pBlueBac appears in FIG. 8.

A baculovirus expression system provides distinct advantages over procaryotic expression systems. The primary advantage in this instance is the large size (130 kbp) of the viral genome which can accommodate substantial segments of foreign DNA such as the CPe-RB coding sequence or CP-RB coding sequences which incorporate other chelating peptides. Secondly baculoviruses are non-infectious to vertebrates; a distinct safety advantage when expressing oncogenes. A comprehensive review of the baculoviral life cycle may be found in Doerfler, W. and Bohm, P. (1986) The Molecular Biology of Baculoviruses, Springer-Verlag, New York. Recombinant baculoviruses are generated by replacing the polyhedrin gene of the wild type baculovirus with a foreign gene through homologous recombination. A distinctive plaque morphology is produced when expression of the polyhedrin gene is lacking. The recombinant baculovirus is produced by inserting the foreign (CP-RB) DNA into a special baculovirus expression vector so that the foreign (CP-RB) DNA is flanked on both sides by polyhedrin DNA. As exemplified herein, the approximately 2,810 bp CPe-RB PCR product is cleaved with SpeI and inserted into the unique NheI restriction site of the pBlueBac baculovirus expression vector. The ends created by cleavage with NheI or SpeI are identical so that two DNA molecules which have been cleaved with NheI or SpeI can be ligated to each other. The vector produced by incorporation of the CPe-RB sequence into pBlueBac is denoted pBlueBacRB. Other baculovirus expression vectors useful in the practice of the instant invention include, but are not limited to, pVL941, pVL1393, pVL1392, pAc700, pAc701, and pAc702. Modifications necessary to the 5′ and 3′ PCR primers used in producing a CP-RB coding sequence for incorporation into these alternative vectors is readily appreciated by one of ordinary skill in the art.

The vector containing the foreign (CP-RB) DNA is then transfected along with the purified wild-type baculovirus DNA into insect cells. Plasmid pBlueBacRB (FIG. 9) is used to transfect *Spodoptera frugiperda* Sf9 cells. Through homologous recombination, the foreign (CP-RB) gene replaces the polyhedrin gene. Once a successful recombination event has occurred, the foreign (CP-RB) gene is consequently under control of the polyhedrin promoter. Cells in which a successful recombination event has occurred are readily identified under a light microscope by the lack of the bright shiny appearance characteristic of cells infected with the wild-type virus or a virus where the polyhedrin gene is expressed. In the case of pBlueBac, colonies indicate the presence of the recombinant baculovirus by their characteristic blue color produced by the β-galactosidase gene of the pBlueBac parent vector gene when cultured in the presence of X-gal. Potential recombinant plaques are then screened to determine if they produce the CP-RB protein. The positive recombinants are then plaque purified until free of wild-type recombinants.

In a manner similar to that outlined above, the DNA sequence encoding the CP-$RB^{60}$ protein is created by PCR amplification of the approximately 1290 bp fragment of the pAbT9300 plasmid corresponding to the 60 kd C-terminal region of the RB gene (FIG. 10). The 5′-primer used for the amplification of the truncated RB coding sequence incorporates a sequence encoding the SpeI and NsiI restriction endonuclease cleavage sites, the Met-His-Trp-His-His-His chelating peptide, and the first 22 nucleotides of the truncated RB gene beginning at the codon corresponding to $Met_{387}$. The DNA sequence of this 50-mer 5′-primer is:

5′-GATCACTAGTATGCATTGGCATCAC-
CATATGATTTTAAATTCAGCAAGTG-3′ (Seq. ID#15)

It should be noted that chelating peptides other than the Met-His-Trp-His-His-His chelating peptide may be incorporated into the practice of the invention. It is readily apparent to one skilled in the art the modifications which would be made to 5′-primer described above so as to express CP-$RB^{60}$ proteins which incorporate other chelating peptides such as those illustrated in Table 1. The 3′-primer used for the amplification of the truncated RB is the same primer as the 3′-primer used in the PCR amplification of the full length RB DNA sequence.

Plasmid $pRB^{60}$ is the plasmid which expresses the CP-$RB^{60}$ protein. Plasmid pRB is created by replacing the hGH coding sequence of plasmid pCZR322 with the CP-$RB^{60}$ coding sequence produced by PCR. A diagram of this procedure appears in FIG. 10. Plasmid pCZR322 is cleaved with the NdeI and BamHI restriction endonucleases to excise the hGH coding sequence. The 5.8 kb BamHI-NdeI vector fragment was isolated by agarose gel electrophoresis and then treated with calf intestinal alkaline phosphatase to remove the 5′ phosphate groups from the linearized DNA molecules. The CP-$RB^{60}$ PCR product was digested with the NsiI and BamHI restriction endonucleases. The resulting CP-$RB^{60}$ DNA sequence possessing 5′ phosphate groups is added to the dephosphorylated DNA in the presence of a synthetic linker and T4 DNA ligase. A single stranded deoxyribonucleotide linker having the sequence 5′-TATGCA-3′ is used to ligate the end of the vector cut by the NdeI endonuclease to the end of the CP-$RB^{60}$ coding sequence cut by the NsiI restriction endonuclease. The resultant plasmid is denoted $pRB^{60}$. A restriction site and function map of $pRB^{60}$ appears in FIG. 11. The ligation mixture was then used directly to transform competent *E. coli* DH5αF′ cells (BRL, Gaithersburg, Md.).

The expression plasmids p16E7e and $pRB^{60}$ isolated from the *E. coli* cells above are transformed into competent *E. coli* strain L201 cells (M.Lei, Lilly Research Laboratories). Cells are grown at 30° C. to an $OD_{600}$ of 0.6–0.8 in 2x TY broth containing 5 μg/ml tetracycline, and then induced for protein expression by growing at 42° C. for 16 hours. Cells are collected by centrifugation at 4400×g for 10 minutes. Cells are lysed by heating to 100° C. for 5 minutes in sample buffer (0.0625M Tris-HC1, pH6.8, 2% SDS, 10% glycerol, 5% 2-mercaptoethanol, 0.001% bromphenol blue) and the proteins analyzed by SDS-PAGE according to the teaching of Laemmli, 1970.

Verification of CP-$RB^{60}$ and CP-E7 protein identities is accomplished by Western Blot analysis as follows. Proteins from induced p16E7e- or $pRB^{60}$- containing L201 cells are separated by SDS-PAGE and transferred electrophoretically to nitrocellulose in 0.05M Tris-HCl, pH8.3, 0.38M glycine, 20% methanol at 40 volts (200–300 mA) for 16 hours. All subsequent steps are performed at 22° C. with shaking. Filters were blocked for 16 hours with 5% BLOTTO (5% dry milk powder, 20 pg/ml thimerosal, Antifoam A) washed twice with TBS-Tween (20 mM Tris-HCl, 500 mM NaCl, 0.05% Tween, pH 7.5) and incubated for 2 hours with mouse monoclonal antibodies against HPV16 E7 (commercially available from Triton Biosciences, Alameda, Calif.) or rabbit polyclonal antibodies against RB as appropriate, diluted 1:100 or 1:20,000 respectively in TBS-Tween-3% BLOTTO. Filters were then washed for 10 minutes with TBS-Tween. Biotinylated goat-anti-mouse antibody or biotinylated goat-anti-rabbit antibody, respectively, (BRL, Gaithersburg, Md.), diluted 1:667 in TBS-Tween-3% BLOTTO, was added and incubated for 1 hour. Filters were then washed three times for 5 minutes with TBS-Tween. Streptavadin-alkaline phosphatase conjugate (BRL, Gaithersburg, Md.), diluted 1:12,000 in AP 7.5 (0.1M NaCl, 2.0 mM $MgCl_2$, pH7.5) containing 0.05% Tween, was added and incubated for 10 minutes. Filters were washed twice for 10 minutes with AP 7.5 containing 0.05% Tween, then washed twice with carbonate buffer (0.1M $NaHCO_3$, 50 mM $MgCl_2$, pH9.8). Color development solution was prepared just prior to use by adding 44 ml of nitroblue tetrazolium chloride (75 mg/ml in 70%N, N-dimethylformamide) and 33 ml of 5-bromo-4-chloro-3-indolyl-p-toluidine salt (50 mg/ml in 100% N-dimethylformamide) to 10 ml of carbonate buffer. Color development solution was added to filters and incubated until desired intensity was achieved. Color development was stopped by rinsing in distilled water for 10 minutes with at least one water change to ensure complete removal of development solution.

E coli engineered to overproduce the CPe-RB$^{60}$ and CPe-E7 proteins contained inclusion bodies or granules enriched in expression product, and were isolated as the first step in the purification. The frozen cell paste was suspended and Na$_2$EDTA containing 4 mg/ml of lysozyme was added. The solution became highly viscous and was then cooled on ice for another thirty minutes. The chilled suspension was sonicated with a Vibracell sonicator to lyse the cells. The lysate was then centrifuged and the pellet was washed with 1M NaCl. The pellet was then washed with 1M urea and then with distilled water. The washed pellet was lyophilized to dryness and then dissolved in sulfitolysis reagent (7.5M urea, 0.5M Tris, 100 mM Na$_2$SO$_3$, 10 mM Na$_2$S$_4$O$_6$, pH 8.2) to convert the cysteines in E7 and RB$^{60}$ to S-sulfonates. The reaction was stirred at room temperature for three hours or more.

The sulfitolysis reaction mixture was filtered through a 0.45 micron filter and applied to a Ni(II) or Co(II) IMAC column prepared as described (Smith, et al, 1987). As stated earlier, Ni(II) may be used for purification purposes but not for the formation of a kinetically inert complex between the CP-protein and the metal ion. As exemplified herein, Ni(II) was used to isolate the CP-RB and CP-RB$^{60}$ proteins as they are not destined to be locked to the resin. In the preferred practice of the invention as exemplified herein, when the Co(II) column was prepared, all of the buffers and water were degassed and purged with helium to exclude air, so as to prevent the premature oxidation of Co(II) to Co(III). A one ml sample of the sulfitolysis solution was injected onto the column and washed with A buffer at 0.2 ml/min until the baseline returned to zero, generally about 1.5 column volumes. The bound CP-E7 and CP-RB$^{60}$ proteins may then eluted by either lowering the pH or by introducing a displacing ligand, such as imidazole. The B buffer used to generate the descending pH gradient was 50 mM acetic acid, 0.5M NaCl, 7M urea, pH 3.7. A gradient from 0 to 100% B over 150 minutes, or about three column volumes, generated a linear pH gradient from pH 7.5 to 3.7. In the preferred practice of the invention as exemplified herein, the CP-E7 and CP-RB$^{60}$ proteins were eluted with an imidazole gradient. The B buffer used to generate an imidazole gradient consisted of 0.5M imidazole, 50 mM NaH$_2$PO$_4$, 0.5M NaCl, 7M urea, pH 7.5. A gradient of 0 to 100% B over 300 ml, or about 4.5 column volumes, was used to elute the CP-RB and CP-RB60 proteins. The protein content of the peaks in the chromatogram was determined by SDS-PAGE using the Novex Tricine-PAGE gel system and by Western Blots. Pools were made of the fractions containing CP-RB$^{60}$ and CP-E7 and then desalted over a Sephadex G25 column. The desalted pools were then lyophilized to dryness. The N-terminal sequences of CP-RB$^{60}$ and CP-E7 were obtained on an ABI 477A Protein Sequencer following the manufacturers instructions. Amino acid analysis of the CP-RB$^{60}$ and CP-E7 proteins were carried out on a Beckman 6300 Automatic Analyzer.

In order to fulfill its role in the assay system, the CP protein is "locked" to the support-immobilized metal ion. The metal ion may be linked to resins such as Toyopearl ® AF-Chelate 650M (TosoHaas, Rohm and Haas Building, Independence Mall West, Philadelphia, Pa. 19105) resin through bifunctional molecules. Such bifunctional molecules comprise two domains: one being designed to bind to the resin of choice and the second possessing a metal ion chelating capability such as IDA which provide the means by which to immobilize the metal ion on the resin and hold the metal ion in a conformation accessible to the CP protein.

As exemplified herein the CPe-E7 protein was locked to the support by the following procedure. The contents of the column containing the immobilized IDA-Co(II)-CPe-E7 complex was transferred to a test tube. The space above the settled gel was replaced with the oxygen or an oxygen containing gas and then capped. The tube was continuously inverted for 24 hours to mix the oxygen containing gas with the bead containing the immobilized IDA-Co(II)-CPe-E7 complex to oxidize the Co(II) to Co(III). The CPe-E7 thereby assumes the "locked" conformation. Equal aliquots of the beads possessing the immobilized IDA-Co(III)-CPe-E7 complex may then be transferred to a reaction vessel for example an Eppendorf tube, or the well of a microtiter plate. The test compound is then introduced to the reaction vessel containing the IDA-Co(III)-CPe-E7 complex. Subsequently, the RB, CPe-RB, RB$^{60}$ or CPe-RB$^{60}$ proteins are introduced to the tube. The presence of the formation of the oncoprotein/anti-oncoprotein complex may be determined in a variety of manners. In the preferred practice of the invention, the binding is measured by scoring the level of fluorescence through the use of fluorescently labelled RB, CPe-RB, RB$^{60}$ or CPe-RB$^{60}$ proteins in the assay. Alternatively, the oncoprotein may be labelled by radioactivity or enzymatic conjugation. All direct modification of the oncoproteins must be achieved in such a manner so as not to inhibit the formation of the oncoprotein/anti-oncoprotein complex. In the alternative, enzymatic, fluorescently, or radioactively labelled antibodies against the oncoprotein may be introduced to the tube to determine the presence of the oncoprotein/antioncoprotein complex.

This invention further provides a method for the orientation of Immunoreactive Proteins on a Solid Support said method comprising the steps of:

a) forming a compound of the formula compound of the formula:

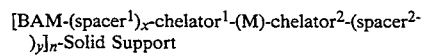

wherein:
"BAM" is an Immunoreactive Protein,
"spacer" is a polypeptide, protein, polysaccharide, polynucleotide or a synthetic organic moiety composed of from 1 to 50 monomer units,
"M" is a transition metal ion capable of forming a kinetically inert transition metal ion complex and M is in a kinetically labile oxidation state.
x=0 or 1,
y=0 or 1,
n=number of monomers bound to the Solid Support, and
  b) changing the oxidation state of said transition metal ion to a kinetically inert oxidation state.

IP molecules are commonly linked to Solid Supports through various chemical means for use in immunoaffinity chromatographic procedures and immunologically based clinical laboratory test kits. Commonly used methods of linkage, such as through lysine residues, often result in the Immunoreactive molecules being bound to the support in random configurations. Consequently, the antigen binding sites of many IP molecules are rendered inaccessible to the antigen. Therefore, a greater quantity of the IP is necessary to provide equivalent binding to a given quantity of antigen. Furthermore, unless one can accurately quantify the fraction of antigen binding sites of these IPs which are exposed relative to those which are rendered inaccessible due to the random orientation of conventional linkage methods, the consistency from lot to lot is difficult to assure, even though the accuracy of the product is more than adequate. Therefore, it is desirable to orient such IP molecules to a support so as to maximize the exposure of the antigen binding site(s) to the environment and consequently to the potential antigen. The instant invention provides a method by which one may achieve specific orientation of IP molecules and concomitantly achieve the desirable goals outlined above.

The ability to orient antibodies is illustrated in FIGS. 23–28. FIG. 23 is an atomic force microscopy image of a freshly cleaved mica surface imaged under PBS, pH 7 using a 12 micrometer scanner head and a 100 micrometer cantilever. The force is approximately $10^{-7}$ Newtons. This figure demonstrates that the freshly cleaved mica surface when imaged under these conditions is visually and atomically flat. FIG. 24 is an atomic force microscopy image of the mica surface after exposure to nickel. nickel chloride was exposed to a freshly cleaved mica surface, rinsed, air-dried, and imaged under the same conditions. This photograph illustrates that the nickel impregnated mica surface is also atomically flat under these conditions.

Atomic force microscopy of proteins was then investigated to determine if the orientation and immobilization of proteins could be accomplished via the immobilized metal ion. FIG. 25 is an atomic force microscopy image of mica contacted with the bare CHEL 13 protein. CHEL 13 was exposed to a freshly cleaved mica surface and imaged under the same conditions as above. The smearing of the protein by the cantilever movement demonstrates that a bare protein does not bind to the mica surface alone. The CHEL13 protein was able to be pushed by the low force of $10^{-9}$ N. FIG. 26 is an atomic force microscopy image of a mica surface impregnated with nickel and exposed to XCEM 449, the parent antibody of CHEL13 without the chelating peptide. The surface was prepared as in FIG. 25 above and imaged under the same conditions as above. One should note that the smearing of the protein by the cantilever suggests that the antibody without the chelating peptide is not specifically bound to the nickel impregnated mica surface.

Next, the protein containing the chelating peptide was then exposed to the nickel impregnated mica surface. FIG. 27 is an atomic force microscopy image of mica-nickel after exposure to CHEL 13. Size determinations of the globular structures showed them to be approximately 142 angstroms by 34 angstroms. This is comparable to measurements of an IgG1 antibody performed by conventional electron microscopy which yielded 150 angstroms by 38 angstroms. Cantilever measurement of distance is dependent upon the rigidity of the structure measured. The globular structures shown in this photograph did not move with the cantilever demonstrating that the protein containing the chelating peptide is bound to the nickel impregnated mica surface.

To insure that the immobilization was not due merely to some particular aspect of the CHEL13 protein and that the linkage to the surface was indeed occurring through the immobilized metal ion, CHEL13 containing bound nickel ion was exposed to the nickel impregnated mica surface. FIG. 28 is a representation of this experiment. Protein moved by cantilever yielded smeary images at best. This suggests that the protein is not bound to the mica and when taken in comparison with the results demonstrated by FIG. 27, the specific binding to the mica surface has indeed occurred through the nickel ion.

In the preferred practice of the invention as exemplified herein, IPs are incorporated into CP-protein form. As previously described, a CP-IP may be synthesized by recombinant DNA technology or well known chemical procedures, such as solution or solid-phase peptide synthesis, or semi-synthesis in solution beginning with protein fragments coupled through conventional solution methods. Recombinant CP-IPs (CP-IPs) are produced by inserting a DNA sequence encoding a chelating peptide in the region of the coding sequence distal to the DNA sequence encoding the antigen binding site of the molecule. Such CP-IPs possess the immobilized metal ion binding capabilities of other CP-proteins. Where one is using the method of this invention to maximize the exposure of the antigen binding site of such CP-IPs, it is preferred to attach the metal binding moiety distal to the the antigenic binding site of IP molecule. These CP-IPs may then be purified by conventional CP-IMAC methodology and/or locked to a support matrix by changing the oxidation state of the bound metal ion so as to achieve a kinetically inert complex.

The DNA sequences of a wide variety of IP molecules are known and have been isolated. These may also be modified by incorporation of a chelating peptide into their primary structure allowing them to be used in the method of the instant invention. Examples of such IPs include but are not limited to, fragments of antibodies (such as but not limited to Fab, Fab', $Fab_2'$, and Fv fragments), and chimeric, humanized, or CDR-grafted antibodies capable of binding antigens of a similar nature as the parent antibody molecule from which they are derived, and "single chain polypeptide binding molecules". Preferred IPs include a CEM, a CEL 007, or Mab 35 antibody or an antigen binding fragment thereof, a CHA 255 antibody or a fragment thereof, and the Fv fragment of CEM231.6.7.

An Fv molecule represents the dimer formed when the Vh (variable region of an immunoglobulin's heavy chain) and VL (variable region of an immunoglobulin's light chain) fragments of an antibody are combined. The notation Fv-CP denotes an Fv molecule covalently linked to a chelating peptide where the linkage is such as not to impair the antigen binding capacity of the Fv molecule. Cleavage of the pro-peptide sequences and assembly of the mature Fv-CP molecule occurs during transport into the periplasm resulting in the active Fv-CP molecule being secreted into the media. Stability of the the resultant Fv-CP molecule may be enhanced through the inclusion of cysteine residues capable of forming disulfide bridges in those areas of close association between the Vh and VL regions.

As exemplified herein, the DNA sequence encoding the His-Trp-His-His-His chelating peptide sequence was inserted in-frame at the 3' end of the coding sequence of the variable region of the heavy chain antibody fragment of the CEM231.6.7 antibody. The DNA sequence of the heavy chain antibody fragment of the CEM231.6.7 antibody is contained on plasmid pNCEMG1. Details of the construction of plasmid pNCEMG1 can be found in European Patent Application 89302312.7, Publication Number 0 332 424, published Sep. 13, 1989, the entire teaching of which is hereby incorporated by reference. The DNA sequence of the light chain antibody fragment of the CEM231.6.7 antibody is contained on plasmid pCEMK. Details of the construction of plasmid DCEMK can be found in the same European Patent Application, 89302312.7 referenced above. These two coding sequences were incorporated into plasmid pJCEMFv6 under control of the Lpp promoter and Lac operator regions. The schematic representation of the creation of plasmid pJCEMFv6 is provided in FIG. 12. The expression product of this plasmid is a pro-Vh fragment possessing a His-Met-His-His-His chelating peptide sequence at the carboxyl terminus of the Vh fragment and a pro-VL fragment.

The DNA sequences encoding the VL and Vh fragments were amplified by PCR. The PCR primers used in the construction of plasmid DJCEMFv6 are listed in Table II and will henceforth be referred to by number.

TABLE II

| OLIGONUCLEOTIDE PRIMERS | |
|---|---|
| PRIMER # | DNA SEQUENCE (5' to 3') |
| 725 | 5'-ATCGCGATCGCAGTGGCACTGGCTGGTTTCG CCACCGTGGCGCAGGCCGACATTG-3' (Seq. ID #16) |
| 726 | 5'-TGCCACTGCGATCGCGATAGCTGTCTTTTTC ATGATATATCTCCTTCTATTTCAGCTCCAGCTT GGT-3' (Seq. ID #17) |
| 729 | 5'-TAGCCGGATCCAAGCTTGGAATTCCTATGAG GAGACGGTGACCGTGGT-3' (Seq. ID #18) |
| 772 | 5'-GCTATCGCGATCGCAGTGGCACTGGCTGGTT TCGCTACCGTGGCGCAGGCCGATGTGCAGCTG GTGGAGTCT-3' (Seq. ID #19) |
| 823 | 5'-AAACATTGGCATCATCATTGAAAGGAGATAT ATCATGAAAA-3' (Seq. ID #20) |
| 824 | 5'-TTCAATGATGATGCCAATGTTTCAGTTCCAG TTTGGTACCAGCACCGAACGTGA-3' (Seq. ID #21) |
| 828 | 5'-ATTGGATCCTAAGCTTCAGGAGGAAACGGTA ACAGTGGTACCTGCACCCCAAACATCGAAGTA-3' (Seq. ID #22) |
| 830 | 5'-ATTCATTAATGCAGCTGGCACGACAGGTTT-3' |

TABLE II-continued

| OLIGONUCLEOTIDE PRIMERS | |
|---|---|
| PRIMER # | DNA SEQUENCE (5' to 3') |
| | (Seq. ID #23) |
| 871 | 5'-ATATTGGATCCTTAGTGATGGTGCCAGTGGG AGGAAACGGTAACCGTAGTACCTGCACCCCAA ACATCGA-3' (Seq. ID #24) |
| 872 | 5'-TGCTGGTACCAAACTGGAACTGAAAGGTGG TAGCGGTGGTAGCGGTGGTTCTGGTGGCTCCG GAGGTGATGTGCAGCTGGTGGAGTCT-3' (Seq. ID #25) |

The 5' and 3' PCR primers used in the amplification the VL coding sequence of pGCEMK were primers 725 and 726 respectively. Primers 725 and 726 encode the positive strand sequence corresponding to the BglI and PvuI restriction endonuclease cleavage sites respectively. The 5' and 3' PCR primers used in the amplification of the Vh coding sequence of pNCEMG1 were primers 772 and 729 respectively. Primers 772 and 729 encode the positive strand sequence corresponding to the PvuI and BamHI restriction endonuclease cleavage sites respectively. The DNA encoding the VL region produced by PCR was digested with the BglI and PvuI restriction endonucleases. The DNA encoding the Vh region produced by PCR was digested with the PvuI and BamHI restriction endonucleases. The sticky ends produced by the PvuI digestion at the 5' end of the VL coding sequence and 3' end of the Vh coding sequence are compatible.

The vector Vec16CHAK was digested with the BqlI and BamHI restriction enzymes to produce sticky ends compatible with the 5' end of the VL coding sequence and the 3' end of the Vh coding sequence respectively. Vector Vec16CHAK is constructed in the following manner. The plasmid pUC18 was digested with the EcoRI and HindIII restriction endonucleases. Plasmid pUC18 is commercially available from GIBCO/BRL, Gaithersburg, Md. A restriction site and function map of plasmid pUC18 appears in FIG. 13 of the accompanying drawings. The approximately 2.6 kb fragment of vector DNA was isolated and purified on a TBE (Tris-Borate electrophoresis buffer, 0.089M Tris, 0.089M boric acid, 0.002M EDTA) agarose gel containing ethidium bromide in substantial accordance with the teaching of Maniatis, T., Fritsch, E.F., and Sambrook, J., *Molecular Cloning: A Laborstory Manual,* Cold Spring Harbor Press (1982), p.150–172. The DNA was visualized under long wave (300–360 nm) uv light and the band corresponding to the EcoRI-HindIII digested vector DNA was isolated by electrophoresis onto DE81 DEAE paper (Schleicher and Schuell, Keene, N.H.). The DNA was removed from the membrane by elution in 1M NaCl then precipitated with ethanol. Two synthetic oligonucleotides of the formula:

```
                    XbaI                                              (Seq. ID #26)
    5'-    AAT TCT CTA GAT AAC GAG GCG CAA AAA ATG AAA

AAG ACA GCT ATC GCG ATC GCA GTG GCA CTG GCT GGT

TTC GCC ACC GTG GCG CAG -3'
           BglI              BamHI
``` and

-continued

```
5'-   GAT CCT GCG CCA CGG TGG CGA AAC CAG CCA GTG    (Seq. ID#27)

CCA CTG CGA TCG CGA TAG CTG TCT TTT TCA TTT TTT

GCG CCT CGT TAT CTA GAG -3'
``` were synthesized using an Applied Biosystems Model 380A or 380B DNA synthesizer (Applied Biosystems, Foster City, Calif.) and annealed. The double stranded polylinker prepared by annealing these two oligonucleotides was ligated with the approximately 2.6 kb vector DNA of pUC18. The resultant vector is denoted Vec16CHAK. A restriction site and function map of Vec16CHAK appears in FIG. 14. The vector DNA was ligated and the resultant plasmid denoted pUCEMFv1.

Plasmid pUCEMFv1 was then digested with XbaI and Eco109. The XbaI-Eco109 fragment was held for religation into plasmid p6CEMFv6 at a later point in the procedure.

Plasmid pUCEMFv1 further served as a template for the amplification of the ompA-VL and ompA-Vh coding sequences. The 5' and 3' primers for the ompA-VL coding sequence were primers 830 and 824 respectively. This resulted in a omp-AVL fragment flanked by XbaI and AspI restriction sites. The ompA-Vh region amplification employed 5' primer 823 and 3' primer 828. The ompA signal peptide is described in Ghrayeb, J. et al. (EMBO J. 3: 2437–2442, 1984) herein incorporated by reference. This produced a fragment encoding the ompA-Vh fragment flanked by AspI and BamHI restriction sites. These fragments were digested with XbaI, AspI and BamHI to produce sticky ends and added to XbaI and BamHI digested pUC18 DNA. The resultant vector denoted pUCEMFv4 was religated and used to transform competent E. coli DH5α cells as above.

The AspI-BamHI fragment of plasmid pGCEMFv4 encoding the ompA-Vh fragment of CEM231.6.7 was used as a template for PCR. The 3' PCR primer (#872) used contains a sequence encoding the His-Trp-His-His-His chelating peptide and a BamHI restriction site. The 5' primer (#871) encodes an AspI restriction endonuclease cleavage site. Following PCR, this fragment was religated into the AspI-BamHI digested pUCEMFv4 vector. The resulting vector is denoted p6CEMFv10 and was used to transform competent E. coli DH5α cells as above.

The vector pGCEMFv10 is digested with the BamHI and Eco109 restriction endonucleases. The approximately 0.3 kb Eco109-BamHI fragment was isolated and purified in substantial accordance with the above. This was ligated to the XbaI-Eco109 fragment derived from pUCEMFv1 and the approximately 2.6 kb XbaI-BamHI digested pUC18 vector DNA in a three fragment ligation. The resulting vector denoted p6CEMFv6 was used to transform competent E. coli DH5α cells as above.

The plasmid p6CEMFv6 was digested with the XbaI and BamHI restriction endonucleases and the fragment containing the tandem VL and Vh coding sequences was isolated and purified as above. This fragment was inserted in to the XbaI-BamHI region of the plasmid pJG105. Plasmid pJG105 was a chloramphenicol resistant expression plasmid derived previously and is described in Ghrayeb et. al. (EMBO J. 3: 2437–2442, 1984). The resulting plasmid is denoted pJCEMFv6. This results in the VL and Vh tandem sequence being under control of the Lpp-Lac promoter and operator regions. Plasmid pJCEMFv6 also contains the chloramphenicol resistance gene.

The plasmid pJCEMFv6 plasmid DNA was used to transform E. coli strain DH10B (BRL, Gaithersburg, Md.). Cells were grown overnight at 30° C. in expression media (Tryprone 24 g/L, yeast extract 48 g/L, disodium phosphate 6.1 g/L, monosodium phosphate 6.1 g/L) containing either 0.0, 0.01 or 0.1 mM isopropylthiogalactoside. After culture, the media was separated from the bacteria by centrifugation and tested for antibody activity to human carcinoembryonic antigen (CEA) by an ELISA inhibition assay. The inhibition assay, a 96 well microtiter plate was first coated with a monoclonal murine antibody CEV124 that reacts with CEA. After binding, the plate was incubated with a source of CEA to enable binding to the antibody on the plate. The material to be tested or a Fab' fragment of CEM231.6.7 (the latter provides a standard curve for inhibition) are added to the plate, followed later by a dilution of antibody XCEM449 antibody conjugated to biotin. Finally after washing, the presence or absence of the biotin conjugate was determined by reaction with Avidin-HRP followed by OPD substrate (Sigma Chem. Co., St. Louis, Mo.). The results show that pJCEMFv6 in DH10B produces active Fv antibody (based on the Fab' standard curve) that contains the His-Trp-His-His-His chelating peptide.

The culture media containing the Fv-CP molecule was then introduced to a column of a hydrophobic resin possessing an immobilized Co(II) ion for purification of the Fv molecule. The column was washed with a weak metal ion complexing agent to remove any non-specifically bound molecules. The Co(II) ion was then oxidized to Co(III) by introducing oxygen, or an oxygen containing gas, or other oxidant which is capable of oxidizing the Co(II) to Co(III) but will not oxidize the CP-Fv molecule to an inactive state to the column material. In the preferred practice of the invention, this was done in a batch process. The contents of the column containing the immobilized IDA-Co(II)-CP-Fv complex were transferred to a test tube. The space above the settled gel was replaced with the oxygen or an oxygen containing gas and then capped. The tube was continuously inverted for 24 hours to mix the oxygen containing gas with the bead containing the immobilized IDA-Co(II)-CP-Fv complex to oxidize the Co(II) to Co(III). Consequently the Fv-CP molecule formed a kinetically inert complex with the immobilized Co(III) ion. The kinetically inert immobilized IDA-Co(III)-CP-Fv complex may then be used either in column immunopurification chromatographic procedures, as reagents in clinical diagnostic test kits, or any of a variety of other applications.

EXAMPLES

The following Examples are merely illustrative of the practice of the invention and should not be considered to limit the scope of the invention in any way.

Example 1. Creation of Plasmid p16E7.

Plasmid p16E7 is the parent of CP-E7 expression vector p16E7e. The coding sequence for the E7 protein was isolated from the pHPV16 plasmid (Behringwerke, A.G., Heidelberg, Germany) and contains the HPV16 genome cloned into the BamHI site of pBR322 (Durst, et. al. 1983). A restriction site and function map of the pHPV 16 plasmid is shown in FIG. 2. The pHPV16 plasmid is digested with the NcoI and NsiI restriction endonucleases to obtain the 301 base pair nucleotide sequence containing the HPV-E7 structural gene.

To construct plasmid p16E7, the 301-bp fragment encoding the E7 gene was inserted in plasmid pCZR322. A restriction site and function map of plasmid pCZR322 appears in FIG. 3. PCZR322 was derived from plasmid pL110. Plasmid pL110 was obtained from the strain E. coli K12 RV308/pL110. Construction of plasmid pL110 and E. coli strain K12 RV308/pL110 is provided in the issued U.S. Pat. No. 4,874,703, Jaskunas, S. Richard, issued Oct. 17, 1989, the entire teaching of which is hereby incorporated by reference. The bacterium E. coli K12 RV308/pL110 was cultured in TY broth (1% triptone, 0.5% yeast extract, 0.5% sodium chloride, pH 7.4) with 50 μg/ml of kanamycin at 25° C. according to conventional microbiological procedures. After the culture was diluted 1:10 into fresh broth and after 3 hours incubation at 37° C., about 0.5 ml of the culture was transferred to a 1.5 ml Eppendorf tube and centrifuged for about 15 seconds. Unless otherwise indicated, all the manipulations were done at ambient temperature. The resultant supernatant was carefully removed with a fine-tip aspirator and the cell pellet was resuspended in about 100 μl of freshly prepared lysozyme solution which contained 2 μg/ml lysozyme, 50 mM glucose, 10 mM EDTA and 25 mM Tris-HCl, pH 8. About 200 μl of alkaline SDS (sodium dodecyl sulfate) solution (0.2N NaOH, 1% SDS) were added and the tube was gently inverted and then kept at 0° C. until lysis was complete (~5 minutes). Next, about 150 μl of 3M sodium acetate were added and the contents of the tube mixed gently by inversion for a few seconds. The tube was maintained at 0° C. for at least 60 minutes and then centrifuged for 15 minutes to yield an almost clear supernatant. The supernatant was transferred to a second centrifuge tube to which 3 volumes of cold 100% ethanol were added. After the tube was held on dry ice/ethanol for 5 minutes, the resultant precipitate was collected by centrifugation (5 minutes) and the supernatant was removed by aspiration. The collected pellet was dissolved in 100 μl of TE (10 mM Tris-HCl, pH 8.0, 1 mM EDTA) and constituted the desired pL110 plasmid DNA.

The desired ~5.8 kb fragment of pL110 was obtained in the following manner. Approximately 5 μg of plasmid pL110 in 50 μl of high salt buffer (100 mM NaCl, 20 mM Tris-HCl, pH 8.0, 10 mM MgCl₂, 5 mM 2-mercaptoethanol) was incubated with ~10 units of XbaI restriction enzyme at 37° C. Approximately ½ hour later ~10 units of BamHI was added and the solution incubated for approximately one-half hour longer. The desired ~5.8 kb XbaI-BamHI restriction fragment was conventionally separated and isolated by agarose gel electrophoresis (Maniatis et al., 1982) and then dissolved in about 100 μl of TE buffer and stored at 0° C. for future use. Plasmid pCZ244 was digested with the BamHI and XbaI restriction endonucleases and the ~0.8 kb fragment isolated in substantial accordance with the above.

About 1 μg of the plasmid pL110 ~5.8 kb BamHI-XbaI fragment and 0.5 μg of the plasmid pCZ244 ~0.6 kb BamHI-XbaI fragment was ligated and the resultant plasmid was then used to transform E. Coli K12 RV308 in substantial accordance with the above teaching. Plasmid pCZ244 was derived from plasmid pCZR1140. Construction of pCZR1140 may be found in Schoner, R.G. et al., European Patent Application No. 85301469.4, Publication No. 0 154 539, published Sep. 11, 1985, the entire teaching of which is hereby incorporated by reference. Plasmid pCZR1140 was digested with ClaI, the ends filled with Klenow and religated to remove the ClaI restriction site. pCZ244 was formed by insertion into this plasmid the following NdeI-BamHI sequence encoding the Met-Glu-Phe-Met human proinsulin derivative:

NdeI

CATATGGAATTCATGTTCGTCAATCAGCACCTTTGTGGTTCTCACC

TCGTTGAAGCTCTCTACCTAGTGTGCGGGGAACGAGGCTTCTTCTA

CACACCCAAGACCCGCCGGGAGGCAGAGGACCTGCAGGTGGGGCAG

GTGGAGCTGGGCGGGGGCCCTGGTGCAGGCAGCCTGCAGCCCTTGG

CCCTGGAGGGGTCCCTGCAGAAGCGTGGCATTGTGGAACAATGCTG

TACCAGCATCTGCTCCCTCTACCAGCTGGAGAACTACTGCAACTAG

ACGCAGCCCGCAGGCCGGAT CC - (Seq. ID #28)

BamHI

Some of the resultant transformants, as conventionally shown by agarose gel electrophoresis (Maniatis et al., 1982) and other tests, contain only the desired ~6.4 kb plasmid (FIG. 11). Such a transformant, herein designated as E. coli K12 RV308/pCZR2441 was selected, plated on TY agar containing appropriate antibiotics and then cultured using conventional microbiological techniques. Plasmid pCZR2441 was digested with BamHI and NdeI as above and the sequence:

NdeI

CATATGTTCCCAACCATTCCCTTATCCAGGCTTTTTGACAACGCTATG (Seq. ID #29)

-continued
CTCCGCGCCCATCGTCTGCACCAGCTGGCCTTTGACACCTACCAGGAG

TTTGAAGAAGCCTATATCCCAAAGGAACAGAAGTATTCATTCCTGCAG

AACCCCCAGACCTCCCTCTGTTTCTCAGAGTCTATTCCGACACCCTCC

AACAGGGAGGAAACACAACAGAAATCCAACCTAGAGCTGCTCCGCATC

TCCCTGCTGCTCATCCAGTCGTGGCTGGAGCCCGTGCAGTTCCTCAGG

AGTGTCTTCGCCAACAGCCTGGTGTACGGCGCCTCTGACAGCAACGTC

TATGACCTCCTAAAGGACCTAGAGGAAGGCATCCAAACGCTGATGGGG

AGGCTGGAAGATGGCAGCCCCCGGACTGGGCAGATCTTCAAGCAGACC

TACAGCAAGTTCGACACAAACTCACACAACGATGACGCACTACTCAAG

AACTACGGGCTGCTCTACTGCTTCAGGAAGGACATGGACAAGGTCGAG

ACATTCCTGCGCATCGTGCAGTGCCGCTCTGTGGAGGGCAGCTGTGCC

TTCTAGCTGCCCCC<u>GGAT CC</u>
                   BamHI encoding met-hGH flanked by NdeI and BamHI restriction sites is substituted. The resultant ~6.4 kb vector is denoted pCZR300.1. PCZR322 was derived from pCZR300.1 by ligation of the ~6.4 kb xbaI-NdeI fragment of DCZR2441 with the linker mercially available from Applied Biosystems, Foster City, Calif.). The DNA was ligated in the presence of T4 DNA ligase. The ligation mixture was then used directly to transform competent E. coli DH5αF' cells (BRL, Gaithersburg, Md.). Plasmid DNA was prepared

| | |
|---|---|
| 5'- CTAGAGGGTATTAATAATGTATCGC TATTATAAAGGAGGATAAACA-3' | (Seq. ID #30) |
|     \|\|\|\|\|\|\|\|\|\|\|\|\|\|\|\|\|\|\|\|\|\|\|\| \|\|\|\|\|\|\|\|\|\|\|\|\|\|\|\|\|\|\|\|\|\| | |
| 3'-TCCCATCCTTATTACATAGCG ATAATATTTCCTCCTATTTGTAT-5' | (Seq. ID #31) |

Plasmid pCZR322 contains the human growth hormone (hGH) gene cloned downstream of a lambda pL promoter. Plasmid p16E7 was created by replacing the hGH coding sequence with the E7 coding sequence using synthetic oligonucleotide linkers. A diagram of this procedure appears in FIG. 4. Plasmid pCZR322 was cleaved with the NdeI and BamHI restriction endonucleases to excise the hGH coding sequence. The desired 5.8 kb BamHI-NdeI restriction fragment is separated and isolated by agarose gel electrophoresis and then treated with calf intestinal alkaline phosphatase to remove the 5' phosphate groups from the linearized DNA molecules according to techniques well known in the art. A protocol for this procedure appears in *Molecular Cloning: A Laboratory Manual*, Sambrook, J., Fritsch, E.F. and Maniatis, T., Cold Spring Harbor Press, 1989, pgs. 1.58–1.61. The E7 sequence isolated above, still possessing 5' phosphate groups, was added to the dephosphorylated DNA in the presence of synthetic linkers. A single stranded 6-nucleotide linker having the sequence 5'-TATGCA-3' was used to ligate the end of the vector DNA cut by the NdeI endonuclease to the end of the E7 coding sequence cut by the NsiI restriction endonuclease. A double stranded linker of the formula:

5' - CATGGG - 3'
          \|\|\|
    3'-CCCTAG - 5' is employed to facilitate the ligation of the NcoI end of the E7 coding sequence to the BamHI end of the vector DNA. These oligonucleotide linkers czn be prepared by techniques well known in the art using conventional DNA synthesizing equipment such as an Applied Biosystems Model 380A or 380B DNA synthesizer (comfrom transformed cells and verification of proper construction was achieved by double stranded DNA sequence analysis using a Sequenase kit (United States Biochemical Corporation, Cleveland, Ohio). A restriction site and function map of plasmid p16E7 appears in FIG. 4.

Example 2. Construction of Plasmid p16E7e.

The plasmid coding for the CP-E7 fusion oncoprotein was created by insertion of a synthetic oligonucleotide encoding the Met-His-Trp-His-His-His chelating peptide at the 5' end of the sequence encoding the E7 protein in plasmid p16E7 prepared in substantial accordance with the teaching of Example 1 above. A synthetic oligonucleotide linker of the sequence

| | |
|---|---|
| 5'-TATGCACTGGCATCACCA-3' | (Seq. ID #32) |
|    \|\|\|\|\|\|\|\|\|\|\|\|\|\|\|\|\|\| | |
| 3'- ACGTGACCGTAGTGGT-5' | (Seq. ID #33) | encoding the chelating peptide, engineered to possess NdeI recognition sequences, was purchased from Indiana University School of Medicine (Indianapolis, Ind.) and cloned into the p16E7 plasmid utilizing the unique NdeI site of that plasmid at the 5' end of the E7 coding sequence. Such double stranded oligonucleotides may also be produced by techniques well known in the art using conventionally available DNA synthesizing equipment or from commercial sources specializing in such syntheses. A restriction site and function map of plasmid p16E7e appears in FIG. 5. Plasmid p16E7e was used to transform competent *E. Coli* DH5αF' cells (BRL, Gaithersburg, Md.). Verification of desired construction was achieved by DNA sequence analysis as described for Example 1.

The parental expression vector (pCZR322) contains the bacteriophage lambda pL promoter under the control of a temperature sensitive repressor. The repressor is functional at 30° C. but is non-functional at 42° C. The expression plasmids p16E7 and p16E7e were used to transform E. coli strain L201 cells (M. Lei, Lilly Research Laboratories). Cells were grown at 30° C. to an $OD_{600}$ of 0.6–0.8 in 2x TY broth containing 5 mg/ml tetracycline, and then induced for protein expression by growing at 42° C. for 16 hours. Cells were collected by centrifugation at 4400 x g for 10 minutes. Cells were lysed by heating to 100° C. for 5 minutes in sample buffer (0.0625M Tris-HCl, pH6.8, 2% SDS, 10% glycerol, 5% 2-mercaptoethanol, 0.001% bromphenol blue) and the proteins analyzed by SDS-PAGE according to the teaching of Laemmli, 1970 the entire teaching of which is hereby incorporated by reference.

Example 3. Western Blot Analysis

Proteins were separated by SDS-PAGE and transferred electrophoretically to nitrocellulose in 0.05M Tris-HCl, pH8.3, 0.38M glycine, 20% methanol at 40 volts (200–300 mA) for 16 hours. All subsequent steps were performed at 22° C. with shaking. Filters were blocked for 16 hours with 5% BLOTTO (5% dry milk powder, 20 pg/ml thimerosal, Antifoam A, Sigma Chemical Co.) washed twice with TBS-Tween (20 mM Tris-HCl, 500 mM NaCl, 0.05% Tween ® (Sigma), pH 7.5) and incubated for 2 hours with HPV16 E7 mouse monoclonal antibodies (Triton Biosciences, Alameda, Calif.) or rabbit polyclonal antibodies against RB as appropriate, diluted 1:100 or 1:20000 respectively in TBS-Tween-3% BLOTTO. Filters were then washed for 10 minutes with TBS-Tween. Biotinylated goat-anti-mouse antibody or biotinylated goat-anti-rabbit antibody respectively (BRL), diluted 1:667 in TBS-Tween-3% BLOTTO, was added and incubated for 1 hour. Filters were then washed three times for 5 minutes with TBS-Tween. Streptavadin-alkaline phosphatase conjugate (BRL), diluted 1:12,000 in AP 7.5 (0.1M NaCl, 2.0 mM $MgCl_2$, pH7.5) containing 0.05% Tween, was added and allowed to incubate for 10 minutes. Filters were washed twice for 10 minutes with AP 7.5 containing 0.05% Tween ®, then washed twice with carbonate buffer (0.1M $NaHCO_3$, 50 mM $MgCl_2$, pH9.8). Color development solution was prepared just prior to use by adding 44 µl of nitroblue tetrazolium chloride (75 mg/ml in 70% N-dimethylformamide) and 33 ml of 5-bromo-4-chloro-3-indolyl-p-toluidine salt (50 mg/ml in 100% N-dimethylformamide) to 10 ml of carbonate buffer. Color development solution was added to filters and incubated until the desired intensity was achieved. Color development was stopped by rinsing in distilled water for 10 minutes with at least one water change to ensure complete removal of development solution.

Example 4.A. Purification of HPV16 CPe-E7 Protein

E. coli engineered to overproduce the CP-E7 proteins contained inclusion bodies or granules enriched in expression product, and were isolated as the first step in the purification. Each gram of frozen cell paste was suspended in ten ml of 50 mM Tris, pH 8 and stirred at room temperature for at least twenty minutes. After the cells were suspended, one ml of 50 mM Na2EDTA containing 4 mg/ml of lysozyme was added per gram of original cell paste. The solution was stirred at room temperature for at least twenty minutes or until the solution became highly viscous, and then cooled on ice for another thirty minutes. The chilled suspension was sonicated with a Vibracell sonicator (Sonics & Materials, Inc.) at a setting of 8, for three two-minute cycles with five minute intervals on ice between cycles. The lysate was then centrifuged at 4° C. at 3000 x g for forty minutes. The pellet was washed with 1M NaCl by resuspending the pellet and centrifuging for 40 minutes at 3000 X g and 4° C. The pellet was then washed with 1M urea following the same procedure, and then with distilled water. The washed pellet was lyophilized to dryness and then dissolved (10 mg solids/ml) in sulfitolysis reagent (7.5M urea, 0.5M Tris, 100 mM $Na_2SO_3$, 10 mM $Na_2S_4O_6$, pH 8.2) to convert the seven cysteines in E7 to S-sulfonates. The reaction was stirred at room temperature for at least three hours.

The sulfitolysis reaction mixture was filtered through a 0.45 micron filter and applied to a Ni(II) or Co(II) IMAC column equilibrated in A buffer (50 mM $NaH_2PO_4$, 0.5M NaCl, 7M urea, pH 7.5). The Ni(II) or Co(II) IMAC column was prepared as described (Smith, et al 1988). In the preferred practice of the invention, when the Co(II) column is prepared, all of the buffers and water were degassed and purged with helium to exclude air, so as to prevent the premature oxidation of Co(II) to Co(III). Briefly, a 1.0×10.0 cm HR column was poured with Pharmacia Fast-Flow Chelating Gel, connected to an FPLC, and washed with four column volumes of distilled water before applying 4 ml of a 50 mM $NiCl_2$ or $CoCl_2$ solution to the column. The metal loaded column was washed again with four column volumes of distilled water before equilibrating with A buffer. A one ml sample of the sulfitolysis solution was injected onto the column and washed with A buffer at 0.2 ml/min until the baseline returned to zero, generally about 1.5 column volumes. The bound material was then eluted by either lowering the pH or by introducing a displacing ligand, such as imidazole. The B buffer used to generate the descending pH gradient was 50 mM acetic acid, 0.5M NaCl, 7M urea, pH 3.7. A gradient from 0 to 100% B over 150 minutes, or about three column volumes, generated a linear pH gradient from pH 7.5 to 3.7 and was used to elute CPa-E7, CPb-E7, and CPc-E7. The B buffer used to generate an imidazole gradient consisted of 0.5M imidazole, 50 mM $NaH_2PO_4$, 0.5M NaCl, 7M urea, DH 7.5. A gradient of 0 to 100% B over 300 ml, or about 4.5 column volumes, was used to elute CPa-E7 through CPe-E7 from the column.

The protein content of the peaks in the chromatogram was determined by SDS-PAGE using the Novex Tricine-PAGE system and by Western Blots. A blank IMAC run using the same imidazole gradient, was used to determine whether Ni(II) leached off the column at high imidazole concentrations. The Ni(II) concentration of each fraction was measured by titrating with excess EDTA, as described previously (Smith, et al. 1987). Pools of the fractions containing CP-E7 were desalted over a Sephadex G25 column equilibrated in 50 mM ammonium bicarbonate pH 8.0 buffer. The desalted pools were then lyophilized to dryness.

The N-terminal sequences of CPe-E7 was obtained on an ABI 477A Protein Sequencer following the manufacturers instructions. Amino acid analysis of the CPb-E7, CPc-E7, and CPe-E7 proteins was carried out on a Beckman 6300 Automatic Analyzer.

Example 4.B. Preparation of Kinetically Inert Immobilized Resin-IDA-Co(III)-CPe-E7 Complex The purified CPe-E7 protein, prepared in accordance with the teaching of Example 4.A. above, was immobilized by forming the kinetically inert immobilized resiniminodiacetic acid-Co(III)-CPe-E7 complex in the following manner.

Co(II), immobilized through IDA, was prepared using commercially available IDA resins, such as Pharmacia Chelating Sepharose® Fast Flow (Pharmacia LKB Biotechnology, 800 Centennial Avenue, Piscataway, N.J. 08854, Toyopearl® AF-Chelate 650M (TosoHaas, Rohm and Haas Building, Independence Mall West, Philadelphia, Pa. 19105), or PerSeptive Biosystems Poros® MC/P (PerSeptive Biosystems, University Park at MIT, 38 Sidney Street, Cambridge, Mass. 02139). The resin (4.0 ml of settled resin) was washed three times with 15 ml of degassed Milli-Q® water, centrifuged after each wash, and kept under a nitrogen atmosphere. A 50 mM solution of $CoCl_2$ was prepared by bubbling nitrogen through 50 ml of Milli-Q® water in a 100 ml round bottom flask for twenty minutes. Solid $CoCl_2$ (0.325 g) was added to the water with nitrogen bubbling through the solution. A blanket of nitrogen was kept over the $CoCl_2$ solution.

In order to prepare the Co(II)-IDA-resin, 12 ml of the 50 mM $COCl_2$ solution was transferred to the washed resin with a disposable plastic syringe, and allowed to react for 15 minutes, under a nitrogen atmosphere. The resin was centrifuged and washed three times with 15 ml of degassed Milli-Q® water, under nitrogen. The washed Co(II)-IDA resin was then equilibrated with buffer (100 mM phosphate, 0.5M NaCl, 7M urea, pH 7.5) by washing twice with 15 ml of degassed buffer. The resin was also equilibrated in buffer without urea with the same results.

The purified CPe-E7 protein (or myoglobin) was added to the Co(II)-IDA-resin blanketed with nitrogen, at a final concentration of 3.0 mg protein/ml of resin. The vessel containing the Co(II)-IDA-resin and purified CPe-E7 protein was capped tightly and gently rotated overnight to form the immobilized kinetically labile resin-IDA-Co(II)-CPe-E7 complex.

The immobilized kinetically labile resin-IDA-Co(II)-CPe-E7 complex was then oxidized to form the immobilized kinetically inert resin-IDA-Co(III)-CPe-E7 complex by gently bubbling air or 95% $O_2$/5% $CO_2$ through the resin-IDA-Co(II)-CPe-E7 slurry, without foaming, for at least 8 hours (or 4 hours in the case of myoglobin). The oxidation of Co(II) to Co(III) was judged to be complete by adding 100 B1 of a 0.5M EDTA pH 8.3 solution to a 100 μl aliquot of the slurry and mixing for 10 minutes. If the Co(II) has been oxidized to the kinetically inert Co(III) state, then the resin will retain its pink color and the supernatant will be clear. If the oxidation is incomplete then the supernatant will be pink and the resin clear. In most instances, after 8 hours of gently bubbling air through the resin slurry, the vessel is capped and gently rotated overnight.

After the oxidation reaction is complete, the resin is washed with an equal volume of 0.5M EDTA DH 8.3, equilibrated in 100 mM phosphate buffer pH 7.0 with three washes and stored at 4° C.

Example 5. Creation of Plasmids pBlueBacRB and pBlueBacRB60

The DNA sequence encoding the human retinoblastoma gene was isolated from the pAbT9300 plasmid (Applied Biotechnology, Cambridge, Mass.). A restriction site and function map of the plasmid pAbT9300 is shown in FIG. 6. The DNA and amino acid sequence of the complete RB gene is disclosed in Friend, S. H. et. al. (1987) PNASUSA USA 84, 9059–9063 the entire teaching of which is hereby incorporated by reference.

The DNA sequences encoding both the CP-RB and CP-RB[60] protein were amplified by the use the PCR (PCR) using the RB gene of pAbT9300. A description of the principles and techniques involved in the use of PCR is provided in *Molecular Cloning: A Laboratory Manual*, 2nd. Edition, Sambrook, A, Fritsch, E.F., and Maniatis, T. (1989) Cold Spring Harbor Press, the entire teaching of which is hereby incorporated by reference. DNA molecules corresponding to the CP-RB and CP-RB[60] proteins were obtained by PCR (PCR) using a Perkin Elmer Cetus DNA Thermal Cycler and GeneAmp kit essentially following the manufacturers instructions with the following modifications: 10 ng of plasmid DNA was used; 4% DMSO was included in the reactions. The Thermal Cycler was set for the following conditions:

1 cycle @94° C.(2 min), 50° C.(1 min), 72° C.(4 min).
9 cycles @94° C.(1 rain), 50° C.(1 rain), 72° C.(4 min).
5 cycles @94° C.(1 min), 50° C. (1 rain), 72° C.(5.3 rain).
5 cycles @94° C.(1 min), 50° C.(1 rain), 72° C.(7.0 rain).
5 cycles @94° C.(1 min), 50° C.(1 min), 72° C.(8.3 rain).
5 cycles @94° C.(1 rain), 50° C.(1 rain), 72° C.(10.0 rain).

All of the primers described for use in the PCR process can be synthesized by techniques well known in the art such as by employing an Applied Biosystems Model 380A or 380B DNA synthesizer (Applied Biosytems, Foster City, Calif.) in substantial accordance with the directions provided by the manufacturer.

A schematic representation of the synthesis of plasmid pBlueBacRB is provided in FIG. 7. The DNA sequence encoding the CP-RB protein was created by PCR amplification of the approximately 2790 bp fragment of the pAbT9300 plasmid corresponding to the translated region of the RB gene. The 5'-primer used for the amplification of the 2790 bp RB coding sequence incorporates a sequence encoding and SpeI restriction endonuclease cleavage site, the Met-His-Trp-His-His-His chelating peptide, and the first 20 nucleotides of the RB gene. The DNA sequence of this 48-mer 5'-primer is:

5'-GATCACTAGTATGCACTGGCATCAC-CATATGCCGCCCAAAACCCCCCG-3'  (Seq.ID#34)

Skilled artisnas realize that chelating peptides other than the Met-His-Trp-His-His-His chelating peptide are amenable to the practice of the invention. It is readily apparent to one skilled in the art the modifications which would be made to 5'-primer described above so as to express CP-RB proteins which incorporate other chelating peptides. The 3'-primer used for the amplification of the 2790 bp RB coding sequence incorporates a sequence encoding and SpeI and BamHI restriction endonuclease cleavage sites and the DNA sequence complementary to the last 7 codons of the RB gene. The DNA sequence of this 37-mer 3'-primer is:

5'-GATCGGATCCACTAGTT-
CATTTCTCTTCCTTGTTTGA-3'   (Seq. D#35)

The DNA sequence encoding the CP-RB protein created by the PCR was inserted into the unique NheI restriction site of the baculovirus expression plasmid, pBlueBac (Invitrogen Corporation, San Diego, Calif.). A restriction site and function map of plasmid pBlueBac appears in FIG. 8. Plasmid pBlueBac was cleaved with the NheI restriction endonuclease and treated with calf intestinal alkaline phosphatase. The CP-RB coding sequence produced by PCR was digested with the SpeI restriction endonuclease yielding ends that are identical to and thus able to be ligated to those resulting from cleavage with the restriction endonuclease NheI. The cleaved CP-RB PCR product is then added to the dephosphorylated pBlueBac DNA in the presence of T4 DNA ligase. The resultant plasmid is pBlueBacRB. A restriction site and function map of pBlueBacRB is provided in FIG. 9.

In a manner similar to that outlined above, the DNA sequence encoding the CP-RB$^{60}$ protein was created by PCR amplification of the approximately 1290 bp 3'-fragment of the pAbT9300 plasmid corresponding to the 60 kd C-terminal region of the RB gene. The 5'-primer used for the amplification of the truncated RB coding sequence incorporates a sequence encoding the NsiI and SpeI restriction endonuclease cleavage sites, the Met-His-Trp-His-His-His chelating peptide, and the first 22 nucleotides of the truncated RB gene beginning at the codon corresponding to Met387. The DNA sequence of this 50-mer 5'-primer is:

(Seq. ID #36)
5'-GATCACTAGTATGCATTGGCATCACCATATGA
TTTTAAATTCAGCAAGTG-3'

The DNA sequence encoding the CP-RB$^{60}$ protein created by the PCR is inserted into the unique NheI site of pBlueBac as described above, resulting in the plasmid pBlueBacRB$^{60}$ Chelating peptides other than the Met-His-Trp-His-His-His chelating peptide may be incorporated into the practice of the invention. It is readily apparent to one skilled in the art the modifications which would be made to 5'-primer described above so as to express CP-RB$^{60}$ proteins which incorporate other chelating peptides such as those illustrated in Table 1. The 3'-primer used for the amplification of the truncated RB is the same primer as the 3'-primer used in the PCR amplification of the full length RB DNA sequence.

Example 6. Creation of Plasmid pRB$^{60}$.

Plasmid pRB$^{60}$ is the bacterial expression plasmid which expresses the CP-RB$^{60}$ protein. Plasmid pRB was created by replacing the hGH coding sequence of plasmid pCZR322 with the CP-RB$^{60}$ coding sequence produced by PCR in substantial accordance with the teaching of Example 5 above. A diagram of this procedure appears in FIG. 10. Plasmid pCZR322 was cleaved with the NdeI and BamHI restriction endonucleases to excise the hGH coding sequence. This reaction mixture was then treated with calf intestinal alkaline phosphatase to remove the 5' phosphate groups from the linearized DNA molecules. The DNA sequence encoding the CP-RB$^{60}$ protein produced by PCR was digested with the NsiI and BamHI restriction endonucleases. The CP-RB$^{60}$ DNA sequence possessing 5' phosphate groups was added to the dephosphorylated DNA in the presence of a synthetic linker and T4 DNA ligase. The single stranded DNA linker having the sequence 5'-TATGCA-3' prepared as described in Example 1 is used to ligate the end of the vector cut with restriction endonuclease NdeI to the end of the CP-RB$^{60}$ coding sequence cut by the restriction endonuclease NsiI. The resultant plasmid is denoted pRB$^{60}$. A restriction site and function map of pRB$^{60}$ appears in FIG. 11. The ligation mixture was then used to transform competent E. coli DH5αF' cells (BRL, Gaithersburg, Md.). Verification of desired construction was achieved by DNA sequence analysis as described for Example 1.

CPe-RB$^{60}$ proteins were expressed and purified in substantial accordance with the teaching of Example 4.A. above.

Example 7. Baculoviral Expression of the Complete CPe-RB Protein.

The plasmid pBlueBac prepared in substantial accordance with the teaching of Example 5 above was used to transform competent E. Coli strain HB101 cells by techniques well known in the art. Transformants were selected on LB agar plates containing 100 μg/ml of ampicillin. One colony was selected for large scale plasmid preparation using the alkaline lysis method including a CsCl/ethidium bromide equilibrium centrifugation.

Seven 25 cm$^2$ flasks were seeded with approximately 2.5×10$^6$ Spodoptera frugiperda (Sf9) cells per flask. Spodoptera frugiperda (Sf9) cells are available from the American Type Culture Collection under accession number #CRL 1711. The cells were allowed to attach for at least 3 hours, after which the medium was removed and replaced with approximately 2 ml of Grace's Antheraea medium (GIBCO/BRL Gaithersburg, Md.) containing 10% heat inactivated fetal bovine serum (FBS) and 50 μg/ml gentamicin. Flasks were incubated at room temperature. Seven sterile tubes containing 0 μg, 0.5 μg, 1 μg, 2 μg, 4 μg, 6 μg, and 8 μg of wild type baculoviral DNA were prepared. To each tube 2 μg of pBlueBac RB DNA prepared above and 950 μl of transfection buffer was added. Transfection buffer was prepared by mixing 10 ml of 10x HEBS (1.37 M NaCl, 0.06M D+-glucose, 0.05M KCl, 0.007M Na$_2$HPO$_4$-7H$_2$O, 0.2M HEPES, in aqueous solution pH=7.1 filter sterilized) 1.5 ml of 1 μg/ml sonicated salmon sperm DNA, 88.5 ml sterile H$_2$O, pH=7.1. 50 μg of 2.5M CaCl$_2$ was added to the DNA/transfection buffer mixture. The solution was mixed and aerated with a 1 ml piper. The tubes were incubated for 25 minutes at room temperature. A precipitate will form. The solution containing the DNA precipitate was then added to the Sf9 cells in the 25 cm2 flasks prepared above. The flasks were incumbated for 4 hours at 27° C. The medium was removed from each flask with a Pasteur piper and rinsed carefully with Grace's Antheraea medium/10% FBS/50 μg/ml gentamicin. Complete medium containing 150 μg/ml X-gal was added. Flasks were incubated 3 to 5 days at 27° C. and observed daily for occlusion bodies as well as for a blue tint in the medium. The medium generally began to turn blue by day 3 or 4 with progression in intensity each day. After the cells were well infected (4 to 5 days), the transfection supernatant (comprised of culture medium and virus) was transferred from each of the seven flasks to sterile, conical centrifuge tubes and centrifuged 10 min at 1000 xg,4° C. Each viral supernatant was then transferred to fresh, sterile tubes. Serial dilutions of the transfection supernatants were prepared at dilutions of $10^{-4}$, $10^{-5}$, and $10^{-6}$. The virus "was plaqued" using agarose overlays containing 150 μg/ml Xgal. The plates were sealed with Parafilm ® to prevent dessication. The plates were inspected daily for plaques that contain occlusion bodies (wild-type virus) and for those that are blue (recombinant virus). The plaques were generally visible by 4 to 5 days postinfection. The number of blue plaques was counted and used to determine which concentration of wild-type baculoviral DNA resulted in the highest frequency of recombinants. This concentration was used for all future transfections with this smock of wild-type baculoviral DNA.

Example 8A Preparation of RB via Isolation of Nuclear Extracts from RB-Vaccinia Virus-Infected Cells.

An alternate way of obtaining the RB protein is to prepare a nuclear extract of cells infected with the recombinant RB-vaccinia virus, vAbT334 (Applied biotechnology, Cambridge, Mass.). The African green monkey kidney cell line BSC-40 is available from A. Bruskin (Applied biotechnology, Cambridge, Mass.). Cells were grown at 37° C. in a humidified 5% $CO_2$ atmosphere, in Dulbecco's modified Eagle medium containing 5% fetal calf serum and 50 μg/ml gentamicin. BSC40 cells were grown to confluence in 150 mm dishes, then infected with vAbT334, at a multiplicity of infection of 2. Cells were incubated at 37° C. for 24 hours. All subsequent steps were carried out at 4° C. Cells were washed once with 2 mls of low salt buffer (LSB) (10 mM HEPES, pH 7.9, 10 mM KCl, 1.5 mM$MgCl_2$, 0.5 mM DTT) per plate, then lysed by incubation for 5 minutes with 2 mls of LSB-PI (LSB containing 0.1% Triton and protease inhibitors: 1 μg/ml aprotinin, 1 μg/ml leupeptin, 1 μg/ml pepstatin A, 100 μg/ml phenylmethylsulfonyl fluoride, 50 μg/ml N-alpha-p-tosyl-L-lysine chloromethyl ketone, and 100 μg/ml N-tosyl-L-phenylalanine chloromethyl ketone) per plate. The lysate was scraped from the plates and nuclei collected by centrifugation at 1000 x g for 5 minutes. The nuclei were washed twice with 2-3 packed nuclei volumes of LSB-PI. The nuclear pellet was resuspended in 1.5 packed nuclei volumes of LSB-PI containing 250 mM NaCl, gently mixed by piperting, incubated for 5 minutes, and then centrifuged at 2000 x g for 5 minutes. The supernatant (nuclear extract) was used immediately following preparation.

Example 8B RB Binding to Kinetically Inert Immobilized IDA-Co(III)-CPe-E7

A 50% slurry of Co(III)-CPe-E7 resin (5 μl), prepared in substantial accordance with the teaching of Example 4.B. herein, containing varying amounts of free CP-E7 (0, 100, 1000, and 5000 ng) was added to 100 μl of recombinant RB nuclear extract prepared as described in Example 8A above. Another tube containing a 50% slurry of Co(III)-myoglobin (5 μl), prepared in substantial accordance with the teaching of Example 4.B. above, served as a control to measure non-specific binding of RB to the resin. The tubes were sealed and gently rotated for two hours at 4° C. The tubes were centrifuged for 3 minutes in a microcentrifuge. The supernatants were removed and the resins washed twice with 1 ml of NP-40 buffer (50 mM Tris, 150 mM NaCl, 0.5% NP-40, pH 8.0) with 10 minutes of gentle rotation after adding buffer. Each resin sample was treated with 30 μl of Novex Tris-Glycine SDS-PAGE 2X sample buffer (Novex, P.O.Box 1158, Encinitas, Calif. 92024), 10 μl of 0.5M EDTA pH 8.3, and 5 μl of β-mercaptoethanol, boiled for 5 minutes, and centrifuged for 3 minutes. The β-mercaptoethanol reduced the Co(III) to the kinetically labile Co(II) state so as to release proteins bound to the resin. The supernatants (40 μl) were applied to pre-poured 4-20% gradient gels from Novex in a Tris-gly buffer system and electrophoresed for two hours with a constant voltage of 125 V.

RB binding was detected by Western Blot using the Sartoblot procedure (Bjerrum, O.J. and Schafer-Nielsen, C., Buffer Systems and Transfer Parameters For Semidry Electroblotting With A Horizontal Apparatus, in *Electrophoresis* 86 (1986) (Dunn, M.J. ed.) Verlag-Chimie, weinheim pp.315). The paper was probed with rabbit antibodies against RB (1:2000 dilution of antiserum) and was then probed with $^{125}$I-donkey anti-rabbit IgG at a concentration of 0.7 μCi/ml. The nitrocellulose paper was then wrapped in plastic wrap and exposed to film for 18 hours. The results demonstrated that only the IDA-Co(III)-CPe-E7 resin bound RB specifically and this binding could be diminished by competition with excess free E7 or CP-E7. The IDA-Co(III)-myoglobin resin was unable to bind RB to the same degree of specificity.

Example 8C Nuclear Protein Binding to IDA Immobilized IDA-Co(III)-CPe-E7

A 50% slurry of IDA-Co(III)-myoglobin resin (100 μl) was added to 1000 μl of NP-40 buffer (50 mM Tris, 150 mM NaCl, 0.5% NP-40, pH 8.0) and 2000 μl of nuclear extract prepared as described in Example 8A from RB-vaccinia infected cells or uninfected cells. The tubes were sealed and gently rotated for two hours at 4° C., to preclear the nuclear extract. The tubes were centrifuged for 3 minutes in a microcentrifuge, the supernatants removed and saved. A 2.25 ml aliquot of the supernatant was added to 100 μl of IDA-Co(III)-CPe-E7 resin, the tubes were sealed and gently rotated for two hours at 4° C. The tubes were centrifuged for 3 minutes in a microcentrifuge, the supernatants removed and the resins washed twice with 1 ml of NP-40 buffer with 10 minutes of gentle rotanion after adding buffer. The IDA-Co(III)-myoglobin resin and IDA-Co(III)-CPe-E7 resins were treated with 175 μl of of Novex TrisGlycine SDS-PAGE 2X sample buffer, 50 μl of 0.5M EDTA pH 8.3, and 25 μl of β-mercaptoethanol, boiled for 5 minutes, and centrifuged for 3 minutes. The β-mercaptoethanol reduced the Co(III) to the kinetically labile Co(II) state so as to release proteins bound to the resin. The supernatants (50 μl/lane) were applied to a Novex TrisGlycine 4-20% gel, electrophoresed for two hours with a constant voltage of 125 V, and stained with Coomassie Blue. A comparison of proteins bound to the IDA-Co(III)-myoglobin resin and IDA-Co(III)-CPe-E7 resin showed at least eight proteins that bind E7 specifically. The molecular weights of these proteins from uninfected cells on the Novex gel are 350 kDa, 140 kDa, 54 kDa, 46 kDa, 41 kDa, 30 kDa, 21.5 kDa, and 13.5 kDa. The molecular weights of these proteins from infected cells on the Novex gel are 300 kDa, 140 kDa, 110 kDa, 46 kDa, 41 kDa, 30 kDa, 25 kDa, and 20 kDa. The proteins from a duplicate gel were transferred to ProBlot ® (Applied Biosystems, Foster City, Calif.) for further sequence analysis. Sequence analysis of the 46 kDa protein from infected and uninfected cells gave the following N-terminal sequence,

M-E-V-K-K-P-A-A-A-A-A-P-G-T-A-E-K-L-S-P-K-A-A which shares homology with rat collagen binding protein (GP46) and mouse serine protease inhibitor homolog J6. The 30 kDa protein from uninfected cells gave the following N-terminal sequence:

M-K-G-D-P-K-K-X-W which shares homology with human high mobility protein HMG1.

Competition experiments with free E7 were carried out to confirm the specific binding of these nuclear proteins to the IDA-Co(III)-CPe-E7 resin. 150 µl aliquots of the precleared nuclear extract described above were added to varying amounts of free E7 (0, 100, 500, 1000, and 5000 ng) and 5 µl of IDA-Co(III)-CPe-E7 resin and allowed to incubate for two hours at 4° C. with gentle rotation. The samples were centrifuged for 3 minutes in a microcentrifuge. The supernatants were removed and the resins washed twice with 1 ml of NP-40 buffer with 10 minutes of gentle rotation after adding buffer. The IDA-Co(III)-CPe-E7 resins were treated with 30 µl of of Novex Tris-Glycine SDS-PAGE 2X sample buffer, 10 µl of 0.5M EDTA pH 8.3, and 5 µl of β-mercaptoethanol, boiled for 5 minutes, and centrifuged for 3 minutes. The mercaptoethanol reduced the Co(III) to the kinetically labile Co(II) state so as to release proteins bound to the resin. The supernatants (50 µl/lane) were applied to a Novex Tris-Glycine 4–20% gel and electrophoresed for two hours with a constant voltage of 125 V. The gels were fixed for 30 minutes with 10% TCA, 3.5% 5-sulfosalicylic acid, and 50% methanol before staining with Coomassie overnight. The gels showed that the bands unique to the IDA-Co(III)-CPe-E7 resin described above can be diminished or eliminated with excess free E7.

Example 9. Preparation of the Precursor of the Organic Chelating Agent Iminodiacetic Acid.

Example 9.A. Preparation of Paranitrobenzyliminodiacetic Acid.

Nitrilotriacetic acid (1.2 mg, 6.3 mmoles) pyridine (8 ml) and acetic anhydride (1 ml) were combined and the resultant suspension was heated until the acid dissolved, giving a light yellow solution. The solution was then heated (without refluxing) for 30 minutes until the solution became a light brown. The solution was cooled to room temperature and evaporated in vacuo to yield a brown oily solution of nitrilotriacetic acid anhydride.

Para-nitrobenzylamine (1 g, 5.3 mmol) was dissolved in 0.1M aqueous sodium bicarbonate, pH 9 buffer (50 ml) and filtered. To the filtered solution was added the acid anhydride solution from above in a dropwise fashion with vigorous stirring. The pH of the solution was adjusted to 9 with saturated sodium carbonate solution after each addition of the acid anhydride. The reaction was complete upon addition of all of the acid anhydride. The para- nitrobenzyl-iminodiacetic was precipitated from the reaction solution by addition of a 1M hydrochloric acid solution, acidifying the solution to a pH of 1. The acidified solution was filtered to obtain 1.76 g of the title product. The purity was confirmed by HPLC (Hewlett-Packard Model 1090A, RP-18 microbore column, eluted with a gradient with 100% Buffer A (Buffer A=50 mM triethylammonium acetate, 10 mM EDTA, pH 6.0) to 100% methanol over a 10 minute period. Nuclear magnetic resonance confirmed the structure (300 mHz, CDCl3,δ3.412(2H);3.27(4H), 4.50(2H); 4.75 (solvent); 4.28–7.45 (2H), 8.125–8.153 (2H). $^{13}$Carbon confirms the structure, δ44.93 (1C), 61.11(3C); 126.57 (2C), 130.53 (2C), 126.57–130.53(6 aromatic C's), 148.65(1C), 149.41(1C), 177.67(1C); 181.88(2C).

Example 9.B Preparation of Paraaminobenzyliminodiacetic Acid.

Para-nitrobenzyliminodiacetic acid (1.g, 3.08 nmoles) and Milli-Q ® water (55 ml) were combined. The pH of the resultant solution was adjusted to 11.5 by the addition of 10 N NaOH solution. Palladium catalyst (5% palladium on carbon, 700 mg) was added under a hydrogen atmosphere. The reaction mixture was stirred for approximately 6 hours and then filtered through glass sinters and a 0.45 micron Millex filter. The pH of the filtrate was adjusted to below 2 with 1 N HCl and then taken to dryness in vacuo. The residue was dissolved in Milli-Q ® water (10 ml) and stored at −70° C. in 1 ml aliquots until further use. Nuclear magnetic resonance confirmed the structure (300 mHz, CDCl3) δ3.268(4H), 3.591(2H); 4.321(2H), 4.741(solvent); 6.822–6.850 (2H); 7.142–7.170 (2H). $^{13}$Carbon confirms the structure, δ45.09(1C); 61.05(1C); 61.153(2C); 119.389 (2C); 131.295 (2C); 131.568 (1C); 148.104 (1C), 176.7 (1C); 181.843 (2C).

Example 9. C. Preparation of para-(isothiocyanato)-benzyliminodiacetic acid.

Three of the aliquots prepared in Example 9.B. were thawed, combined and taken to dryness in vacuo. To the resultant residue was added 3M HCl (8 ml) and distilled thiophosgene (1 ml) and the reaction stirred overnight at ambient temperature. Diethyl ether (12 ml) was added and the resultant precipitate was isolated by filtration. The collected solid was washed with diethyl ether and dried under vacuum. The residue was then dissolved in Milli-Q ® water (7 ml), the pH of the solution was adjusted to 7 with 0.1M NaHCO3 (pH8.2) and then stored as 1 ml aliquots at −70° C. Nuclear magnetic resonance confirmed the structure (300 mHz, CDCl3) δ3.336 (4H); 3.506 (2H); 4.376 (2H), 4.751 (solvent); aromatic region 7.240–7.254 (4H). $^{13}$Carbon confirms the structure, δ45.018 (1C), 60.510 (1C); 60.844 (2C); 128.592–140.008 (6 aromatic carbons);

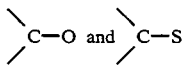

region 175.7–180.2 (2C). The infrared spectrometry shows and N-H stretch at 3400 cm$^{-1}$;S=C=N stretch at 2100 cm$^{-1}$; and C=O stretch at 1650–1750 cm$^{-1}$.

Example 10. Affinity Purification of Anti-E7 Antibodies Using Immobilized Co(III) CPe-E7

IDA-Co(III)-CPe-E7 resin was prepared using Pharmacia Chelating Sepharose ® Fast Flow as described in Example 4B above. An affinity column (1.0×10.0 cm) was poured with the resin, then equilibrated with Buffer C (100 mM NaH2PO4, pH 8.1). A 3 ml sample of rabbit sera was applied to the column with a flow rate of 0.2 ml/minute. The flow was stopped once the entire sample was applied and allowed to react with the immobilized IDA-Co(III)-CPe-E7 for 90 minutes. The column was washed with two column volumes of buffer C to elute unbound protein. The bound protein was eluted with a linear gradient from 0 to 100% over 20 minutes with buffer D (100 mM glycine, 7.5M urea, pH 2.5). Fractions were neutralized with 3M Tris Base and then analyzed by SDS-PAGE using pre-poured 4–20% gradient gels from Novex with a Tris-gly buffer system. Anti-E7 antibody was measured in each fraction using a standard ELISA procedure with o-phenylenediamine detection at 490 nm. The results of these experiments showed that the anti-E7 antibody was contained in the peak of bound protein with a major band with a molecular weight of 150 kDa and small amounts of contaminating lower molecular weight bands.

Example 11 Purification of HPV16 E7 Using Affinity Chromatography Column and Anti-E7 Antibodies E. coli cells containing the direct expression product, HPV16-E7, were lysed, solubilized, and sulfitolyzed as described for the CP-E7 proteins in Example 4. The urea and excess sulfite from the sulfitolysis solution were then removed by desairing the solution over a 2.5×40 cm Sephadex G25 column equilibrated in 100 mM sodium phosphate pH 8.0. The desalted solution was applied to an Anti-E7 affinity column prepared following the manufacturers instructions, using Carbolink ® Coupling Gel supplied in the ImmunoPure Ag/Ab Immobilization Kit #3 (Pierce Chemical Co. USA, 3747 N. Meridian Rd., Rockford, Ill. 61105). The Anti-E7 polyclonal antibody used in the conjugation reaction was first purified by passing the rabbit antisera over a column of CP-E7 immobilized on an IMAC column, as described in Example 10. The protein bound to the Anti-E7 affinity column was eluted with 7M urea, 100 mM glycine, pH 2.3 buffer. The pool of E7 was desalted over a G25 column equilibrated in 50 mM bicarbonate buffer pH 8.0 as described above and then lyophilized to dryness.

Example 12 Construction of Plasmid pJCEMFv6

This following description provides the construction of an expression vector for procaryotic cells which results in the production of an Fv binding fragment of an antibody molecule. The antibody molecule is composed of a light chain variable region associated with a heavy chain variable region both derived from the murine hybridoma cell line CEM231.6.7. This antibody molecule reacts with human carcinoembryonic antigen. The Fv protein encoded by plasmid pJCEMFv6 contains the His-Trp-His-His-His chelating peptide fused to the C-terminus of the heavy chain subunit.

The murine hybridoma CEM231.6.7 was deposited on Jan. 7, 1988 with the American Type Culture Collection, Rockville, Md., under accession #ATCC HB9620. The isolation of genomic DNA coding for the light and heavy chains of CEM231.6.7 is disclosed in the European patent application 89302312.7. European Publication Number 0 332 424 A2, Publication Date: Sep. 13, 1989 the entire teaching of which is herein incorporated by reference. These Examples describe the use of the CEM231.6.7 variable regions to construct human/mouse chimeric expression vectors for the light chain (pGCEMK) and the heavy chain (pNCEMG1). It is these two vectors which were used as a source of DNA to construct pJCEMFv6. Although the two vectors used for construction of pJCEMFv6 were obtained from genomic DNA cloning, one could also make the construct using a vector derived from a cDNA source or even a completely synthetic gene. In the practice of the instant invention, the oligonucleotide primers listed in Table II were employed and will hereinafter be referred to by number.

Example 12.A. Construction of Plasmids pGCEMK and pNCEMG1

Details of the construction of plasmids pGCEMK and pNCEMG1 is taught in European Patent Application 89302312.7, Publication Number 0 332 424, published Sep. 13, 1989.

Example 12.B. Construction of Plasmid pUCEMFv1

The light chain and heavy chain variable region DNAs were obtained by PCR using a Perkin Elmer Cetus DNA Thermal Cycler and GeneAmp kit as per the manufacturers instructions. The Thermal Cycler was set for the following conditions: 3 min. @94° C. for 1 cycle followed by 25 cycles of @94° C. (1 min.), @50° C. (1 min.), @72° C. (2 min.), with autoextension of 4 sec./cycle and a final cycle of 72° C. (10 min.).

For the amplification of the light chain coding sequence via PCR, pGCEMK was used as the template DNA together with 5' primer 725 and the 3' primer 726, resulting in a light chain variable gene DNA sequence with BglI and PvuI restriction sites. The DNA obtained through PCR was purified by extraction with one volume of phenol/chloroform, and precipitation by addition of 1/10th volume of 2.5M sodium acetate and 2 volumes of ethanol. The light chain DNA was then digested with BglI and PvuI restriction enzymes according to the manufacturers instructions (GIBCO-BRL. P.O. Box 6009, Gaithersburg, Md.). After digestion, the light chain DNA was isolated by agarose gel electrophoresis on a TBE agarose gel containing ethidium bromide. The DNA was visualized under UV light and the band corresponding to the BglI-PvuI digested light chain DNA was isolated by electrophoresis onto DE81 DEAE paper (Schleicher and Schuell, Keene, N.H.). The DNA was removed from the membrane by elution in 1M NaCl and then precipitated with ethanol.

The heavy chain variable region DNA was obtained in a manner similar to that described above for the light chain with the following exceptions. The plasmid pNCEMG1 was used as the source of the heavy chain variable region DNA. This plasmid provided the template heavy chain variable region DNA for the PCR reaction. The 5' and 3' primers employed were 772 and 729 respectively. Following PCR, the amplified DNA corresponding to the heavy chain variable region DNA was digested with the PvuI and BamHI restriction endonucleases. The DNA corresponding to the heavy chain variable region was isolated and purified in substantial accordance with the teaching above.

Vector Vec16CHAK was constructed in the following manner. The plasmid pUC18 was digested with the EcoRI and HindIII restriction endonucleases. Plasmid pUC18 is commercially available from GIBCO-BRL, Gaithersburg, Md. A restriction site and function map of plasmid pUC18 appears in FIG. 13. The approximately 2.6 kb fragment of vector DNA was isolated and purified on a TBE (0.089M Tris, 0.089M boric acid, 0.002M EDTA) agarose gel containing ethidium bromide in substantial accordance with the teaching of Maniatis, T., Fritsch, E.F., and Sambrook, J., *Molecular Cloning: A Laboratory Manual*, Cold Spring Harbor Press (1982), p.150–172. The DNA was visualized under long wave (300–360 nm) UV light and the band corresponding to the EcoRI-HindIII digested vector DNA was isolated by electrophoresis onto DE81 DEAE paper (Schleicher and Schuell, Keene, N.H.). The DNA was removed from the membrane by elution in 1M NaCl then precipitated with ethanol. Two synthetic oligonucleotides of the formula:

```
            XbaI
5'-   AAT TCT CTA GAT AAC GAG GCG CAA AAA ATG AAA

AAG ACA GCT ATC GCG ATC GCA GTG GCA CTG GCT GGT

TTC GCC ACC GTG GCG CAG -3'
          BglI              BamHI
``` and

```
5'-   GAT CCT GCG CCA CGG TGG CGA AAC CAG CCA GTG

CCA CTG CGA TCG CGA TAG CTG TCT TTT TCA TTT TTT

GCG CCT CGT TAT CTA GAG -3'
``` were synthesized using an Applied Biosystems Model 380A or 80B DNA synthesizer (Applied Biosystems, Foster City, Calif.) and annealed. The double stranded polylinker prepared by annealing these two oligonucleotides was ligated with the approximately 2.6 kb vector DNA of pUC18. The resultant vector is denoted Vec16CHAK. A restriction site and function map of Vec16CHAK appears in FIG. 14.

Vec16CHAK was digested with the AflIII and BglI restriction endonucleases. The 410 bp AflIII-BglI fragment was isolated and purified in substantial accordance with the above procedure. In a separate procedure, Vec16CHAK was digested with the BamHI and AflIII restriction endonucleases. The approximately 2250 bp BamHi-AflIII fragment was isolated and purified as above.

The DNA sequences of the light and heavy chain variable regions prepared by PCR was mixed with the 410 bp AflIII-BglI and 2250 bp BamHI-AflIII fragments of vector Vec16CHAK in a four fragment ligation. The DNA was ligated in the presence of T4 DNA ligase (GIBCO/BRL, Gaithersburg, Md.). The resultant plasmid was denoted pUCEMFv1. A restriction site and function map of plasmid pUCEMFv1 appears in FIG. 15 of the accompanying drawings. pUCEMFv1 was used to transform competent E. coli DH5α cells (BRL, Gaithersburg, Md.) by the CaCl2 transformation procedure in substantial accordance with the protocol recommended by the manufacturer. The transformed cells were plated on LB agar plates containing 100 μg/ml methicillin and incubated overnight at 37° C. Colonies were grown, plasmid DNA purified and analyzed by restriction enzyme digestion in substantial accord with the teaching of Sambrook, Fritsch and Maniatis, *Molecular Cloning: A Laboratory Manual*, Cold Spring Harbor Press, (1990).

Example 12.C. Construction of Plasmid pUCEMFv4

Plasmid pUCEMFv4 was created by the insertion of two PCR fragments corresponding to the light and heavy chain variable regions into the XbaI-BamHI digested pUC18 plasmid. The conditions for PCR amplification were as described above. In one reaction, pUCEMFv1 was used as a template DNA together with primers 830 and 824. Primers 830 and 824 provide restriction sites for XbaI and AspI respectively. After PCR, this fragment was digested with xbaI and AspI (=Asp718) prior to purification. Isolation and purification was performed in substantial accordance with the teaching of Example 12.B. above. For the other PCR step, pUCEMFv1 template DNA was used with primers 823 and 828. Primers 823 and 828 provide restriction sites for AspI and BamHI respectively. This fragment was then digested with AspI and BamHI and purified. Isolation and purification were performed in substantial accordance with the teaching of Example 12.B. above. In the final construction step, the two PCR derived fragments were ligated to a purified approximately 2.6 kb DNA fragment of pUC18 derived by digesting pUC18 with the XbaI and BamHI restriction enzymes. The resulting plasmid, pUCEMFv4, was used to transform competent E. Coli DH5α cells. The generation and selection of bacterial colonies containing the pUCEMFv4 plasmid was done using the general principles described above in Example 12.C.

Example 12.D. Construction of Plasmid D6CEMV10 p6CEMv10 was produced by ligation of three fragments. One fragment was a XbaI-AspI restriction fragment derived from pUCEMFv4. A second fragment was obtained by PCR where pUCEMFv4 was used as template DNA together with primers 872 and 871. After the PCR reaction, the DNA was processed according to the teaching of Example 12. above except that the enzymes used for restriction were ASDI (=ASD718) and BamHI. The above described fragments were ligated to a purified 2.6 kb XbaI-BamHI fragment obtained from pUC18. The generation and selection of bacterial colonies was done using the general principles described above in Example 12.C.

Example 12.E. Construction of Plasmid p6CEMFv6 p6CEMFv6 was constructed by ligation of 3 fragments from 3 separate sources. pUCEMFv1 was digested with xbaI and Eco109 to yield a 0.4 kb fragment. p6CEMv10 was digested with Eco109 and BamHI to yield a 0.3 kb fragment. These two fragments were then ligated to a purified 2.6 kb fragment obtained by XbaI and BamHI digestion of pUC18. The generation and selection of bacterial colonies was done using the general principles described above in Example 12.B.

Example 12.F. Construction of Plasmid DJCEMFv6 pJCEMFv6 was obtained by ligation of 2 fragments. An XbaI and BamHI digested fragment of about 0.7 kb from p6CEMFv6 was ligated to an approximately 11 kb fragment obtained from pJG105 by digestion with XbaI, EcoRI and BamHI. pJG105 is a chloramphenicol resistant expression plasmid derived previously by Ghrayeb et, al. (EMBO J. 3: 2437–2442, 1984). Bacteria were transformed, grown and selected according to the general principles described above in Example 12.C. except that 30 mg/ml chloramphenicol was used in place of ampicillin to select drug resistant colonies.

Example 12.G. DNA Sequencing of Cloned Genes

Sequencing of cloned CEM231.6.7 heavy and light chain variable regions along with the His-Trp-His-His-His fusion peptide was done by standard procedures for double stranded templates using the protocols provided by the sequencing kit Sequenase, commercially available from U.S. Biochemicals (Cleveland, Ohio). The DNA sequence of the light chain variable region containing the ompA leader peptide is:

| 5'- | ATG | AAA | AAG | ACA | GCT | ATC | GCG | ATC | GCA | GTG | GCA | CTG |
|---|---|---|---|---|---|---|---|---|---|---|---|---|
| GCT | GGT | TTC | GCC | ACC | GTG | GCG | CAG | GCC | GAC | ATT | GTG | ATG |
| ACC | CAG | TCT | CAA | AAA | TTC | ATG | TCC | ACA | TCA | GTA | GGA | GAC |
| AGG | GTC | AGC | ATC | ACC | TGC | AAG | GCC | AGT | CAG | AAT | GTT | CGT |
| ACT | GCT | GTT | GCC | TGG | TAT | CAA | CAG | AAA | CCA | GGG | CAG | TCT |
| CCT | AAA | GCA | CTG | ATT | TAC | TTG | GCA | TCC | AAC | CGG | TAC | ACT |
| GGA | GTC | CCT | GAT | CGC | TTC | ACA | GGC | AGT | GGA | TCT | GGG | ACA |
| GAT | TTC | ACT | CTC | ACC | ATT | ACC | AAT | GTG | CAA | TCT | GAA | GAC |
| CTG | GCA | GAT | TAT | TTC | TGT | CTG | CAA | CAT | TGG | AAT | TAT | CCG |
| CTC | ACG | TTC | GGT | GCT | GGG | ACC | AAG | CTG | GAG | CTG | AAA | TAG- |
| 3' (Seq. ID #37) | | | | | | | | | | | | |

The DNA sequence of the heavy chain variable region containing the ompA leader peptide and incorporating the His-Trp-His-His-His chelating peptide coding sequence at the 3' end is:

| 5'- | ATG | AAA | AAG | ACA | GCT | ATC | GCG | ATC | GCA | GTG | GCA | CTG |
|---|---|---|---|---|---|---|---|---|---|---|---|---|
| GCT | GGT | TTC | GCC | ACC | GTG | GCG | CAG | GCC | GAT | GTG | CAG | CTG |
| GTG | GAG | TCT | GGG | GGA | GGC | TTA | GTG | CAG | CCT | GGA | GGG | TCC |
| CGG | AAA | CTC | TCC | TGT | GCA | GCC | TCT | GGA | TTC | ACT | TTC | AGT |
| AAC | TTT | GGA | ATG | CAC | TGG | ATT | CGT | CAG | GCT | CCA | GAG | AAG |
| GGA | CTG | GAG | TGG | GTC | GCA | TAC | ATT | AGT | GGT | GGC | AGT | AGT |
| ACC | ATC | TAC | TAT | GCA | GAC | ACA | GTG | AAG | GGC | CGA | TTC | ACC |
| ATC | TGG | AGA | GAC | AAT | CCC | AGG | AAC | ACC | CTC | TTC | CTG | CAA |
| ATG | ACC | AGT | CTA | AGG | TCT | GAG | GAC | ACG | GCC | ATG | TTT | TAC |
| TGT | GCA | AGA | GAT | TAC | TAC | GCT | AAC | AAC | TAC | TGG | TAC | TTC |
| GAT | GTT | TGG | GGT | GCA | GGT | ACT | ACG | GTT | ACC | GTT | TCC | TCC |
| CAC | TGG | CAC | CAT | CAC | TAA | -3' (Seq. ID #38) | | | | | | |

From the DNA sequences obtained, the amino acid sequences were deduced by computer software program MAPSEQ, commercially available from DNAstar (Madison, Wis.).

Example 12.H. Expression and Antibody Activity of pJCEMFv6

Plasmid pJCEMFv6 DNA was used to transform competent *E. coli* strain DH10B (BRL, Gaithersburg, Md.). Cells were grown overnight at 30° C. in expression media (Tryprone 24 g/L, yeast extract 48 g/L, disodium phosphate 6.1 g/L, monosodium phosphate 6.1 g/L) containing either 0.0, 0.01 or 0.1 mM isopropylthiogalactoside. After culture, the media was separated from the bacteria by centrifugation and tested for antibody activity to human carcinoembryonic antigen (CEA) by an ELISA inhibition assay. The inhibition assay was performed in a 96 well micromiter plate first coated with a monoclonal murine antibody CEV124 that reacts with CEA. After binding, the plate was incubated with a CEA containing soluble extract of T84 colon carcinoma cells, to enable binding to the antibody on the plate. The material to be tested or a Fab' fragment of CEM231.6.7 (the latter provides a standard curve for inhibition) were added to the plate, followed later by a dilution of antibody XCEM449 antibody conjugated to biotin. After washing to remove unbound molecules, the presence or absence of the biotin conjugate was determined by reaction with Avidin-HRP followed by OPD substrate (Sigma Chem. Co., St. Louis, Mo.). The results indicate that DH10B cells transformed with pJCEMFv6 produces active CP-Fv antibody protein.

Example 13 Vector Construction

Murine hybridoma cells, designated as CEM 231.6.7, were used in the examples to derive and clone genomic DNA for variable light and heavy chain variable regions. Murine hybridoma CEM 231.6.7 was deposited on Jan. 7, 1988 with the American Type Culture Collection, Rockville, Md., under the accession number ATCC HB 9620. The cloned genomic DNA from murine hybridoma CEM 231.6.7, and human peripheral blood lymphocytes, were used for the construction of the chimeric genes. Transfection of chimeric genes was accomplished by electroporation techniques, essentially as described by Toneguzzo, F., et al., *Molecular and Cell, Biol.,* 6:703–706 (1986); and Chu, G. et al.., *Nucleic Acid Res.,* 15:1311–1325 (1987), herein incorporated by reference. The host cells SP2/0-Ag14 hybridoma cells were the recipients of the chimeric genes. The SP2/0Ag14 hybridoma cells are available from the American Type Culture Collection, Rockville, Md.

Example 13A. Isolation of pNCEMγ1

The construction of pNCEMγ1, the anti-CEA IgG1 heavy chain expression vector is described in U.S patent application Ser. No. 07/272,577, filed Nov. 17, 1988, which is hereby incorporated by reference in its entirety. Isolation and CsCl purification of this plasmid was by standard DNA preparation methods as described in several laboratory manuals (e.g. Molecular Cloning, a laboratory manual. 2nd Ed. by J. Sambrook, E.F. Fritch, and T. Maniatis, Cold Spring Harbor Laboratory, Cold Spring Harbor, 1989)

Example 13.B. Construction of Plasmid pNCEMγ1-CHEL 13 Containing Anti-CEA IgG1 Heavy Chain with a C-Terminal Peptide Encoding HIS-TRP-HIS-HIS-HIS-PRO The cloning strategy involved the generation of 4 DNA fragments from the expression vector pNCEMγ1. The first fragment (approximately 9.0 kb) was obtained by restriction digest of 10 μg of pNCEMy1 DNA in TE buffer, with 20 units of each of the restriction enzymes SalI, NruI, and ClaI from GIBCO-BRL (Gaithersburg, Md.) in Universal Restriction Buffer from Stratagene (San Diego, Calif.). The digest was carried out for 2 hrs. at 37° C. After ethanol precipitation and resuspension in H₂O, the digested DNA was electrophoresed in a 0.5% TBE agarose gel containing 0.5 μg/ml of ethidium bromide at 90 V for 45 min. Following visualization on a UV transparent light box the 9.0 kb fragment was electrophoresed onto DEAE 81 paper from Schleicher and Schuell (Keene, N.H.). The fragment was eluted in 1.2M NaCl and recovered by ethanol precipitation. The eluted fragment, called Fragment 1, was then resuspended in 20 μl of H₂O. The second fragment was generated by PCR (as described in PCR Technology, edited by H.A. Erlich, Stockton Press, New York, 1989). Two oligonucleotide primers were synthesized on a DNA synthesizer (Model 8700) from Milligen Biosearch [a division of Millipore (Bedford, Mass.)] using the manufacturer's protocols. Primer 1, (#984) was designed to match a 30 base pair sequence 5' of the single SalI restriction site in pNCEMγ1. Primer 2 (#855) was designed to match 30 bp of the complementary strand sequence within the CH3 region of the pNCEMγ1 gene and to contain an 18 base pair sequence coding for His-Trp-His-His-His-Pro as well as a stop codon, and an XmaIII restriction sequence tail. The template, the 2 primers, the dNTP mix, and TAQ polymerase were mixed together and brought to final volume of 100 μl in reaction buffer. 50 μl of mineral oil were floated on top of the reaction and the tube was put into a DNA thermocycler from Perkin Elmer Cetus (Emeryville, Calif.), set to cycle at 94° C. for 1 minute, 60° C. for 1 minute and 72° C. for 2 min for 25 cycles. Following this PCR reaction, 5 μl of the reaction mixture was analyzed on a 0.75% agarose gel in TBE buffer. The desired approximately 1.8 kb fragment was observed Via a UV transilluminator. This fragment herein called Fragment 2 was isolated and purified as described above for Fragment 1 and was cloned into a holding vector, pBR322, available from the American Type Culture Collection (ATCC Designation 31344) for sequence confirmation of the added chelating peptide sequence as follows. 10 μg of pBR322 vector and Fragment 2 were digested separately with SalI and XmaIII. The SalI digest was carried out as above. The XmaIII digest including 20 units of enzyme and Restriction Buffer #5 (GIBCO-BRL, Gaithersburg, Md.) was carried out for 2 hours at 37° C. 300 ng of the pBR322 SalI/XmaIII 4.1 kb fragment (isolated using DEAE 81 paper as above) and 200 ng of PCR generated SalI-XmaIII digested 1.8 kb fragment were resuspended together in a total volume of 20 μl containing 4 units of T4 ligase and 0.5 mM ATP in Ligase Buffer. Ligase and buffer are available from Stratagene (San Diego, Calif.). Ligation was done at 14° C. overnight. 10 μl of the ligated mixture was incubated with 100 μl of MC1061 competent bacterial cells available from the American Type Culture Collection (ATCC Designation #53338) on ice for 30 min. The mixture was heat shocked at 42° C. for 45 seconds, followed by the addition of 1 ml of SOC, described in Molecular Cloning, supra., and cultured for 1 hr with shaking at 37° C. Transformed MC1061 cells were then plated on LB - AMP plates (50 μg/ml ampicillin) overnight at 37° C. DNA from colonies which grew up was analyzed via restriction digestion for the correct insert size, indicating successful transformation. The third fragment was generated by PCR as follows. Primer 1 (#977) matched a 30 base pair region of pNCEMγ1 and also provided the chelating peptide sequence, stop codon, and XmaIII site as a 5' tail. Primer 2 (#978) included the complementary strand 42 bp 3' of the polyadenylation signal and an NruI restriction site. The PCR reagents and conditions were identical to those described above for Fragment 2. A 324 bp fragment resulted from this PCR step and was called Fragment 3. The fourth fragment was obtained by using Fragment 2 and Fragment 3 as templates for a PCR step. In this step, Primer 1 (#854) matched the 5' sequence of Fragment 2 and Primer 2 (#978) the 3' sequence of Fragment 3. The overlapping PCR reaction was carried out generating a fragment of size equal to the sum of Fragment 2 and Fragment 3 (i.e. 2134 bp). The PCR conditions were as described above. The 2134 bp Fragment 4 was digested with SalI and NruI, as described above, and ligated to Fragment 1. The ligation product was used to transform DH10B Electromax cells obtained from BRL (Gaithersburg, Md.). Transformed cells were plated and grown overnight at 37° C. on L-Broth, ampicillin plates (50 μg/ml ampicillin). DNA from the resulting colonies was analyzed via restriction digestion for the correct insert size, indicating successful transformation.

Example 13.C. Construction of Plasmid PGCEMK(SRE) Containing Chimeric Light Chain Immunoglobulin Genes The eukaryotic expression vector containing the murine VL region fused to the human kappa gene was constructed using the vector pSV2gpt, available from the American Type Culture Collection, (ATCC Designation #37145). One μg of pSV2gpt DNA was digested with the restriction enzyme EcoRI using 1 unit/μg of DNA in Reaction Buffer #3 (GIBCO-BRL, Gaithersburg, Md.). The EcoRI ends were then made blunt by adding 10 μg of 5 mM each of the 4 deoxyribonucleotides dTTP, dGTP, dCTP and dATP, 2 units of Klenow enzyme and a 10 x buffer (0.5M Tris HCl pH 7.5; 0.1M MgCl₂; 10 mM dithiothreitol) in a total volume of 50 μl as described in *Molecular Cloning*, supra. The reaction went 30 minutes at room temperature and was followed by a ligation reaction in which phosphorylated ClaI linkers (2 μg) (New England BioLabs, Beverly, Mass.) were ligated to the 500 ng of EcoRI blunt-ended pSV2gpt in order to create a new ClaI site for the new vector. The ClaI linkers sequence was d(pCATCCGATG). Ligation reactions were carried out as described under Example 13 B. Following ligation, excess linkers were removed by electrophoresis of the DNA and isolation of the linear pSV2gpt-ClaI fragment onto DEAE 81 paper as in Example 13 B. The isolated DNA was circularized using reagents described in Example 13 B. Competent HB101 cells were transformed as in Example 13 B and the ampicillin resistant colonies resulting therefrom were analyzed by restriction enzyme digestion.

The resulting vector, pSV2gpt-ClaI, was then digested with ClaI and BamHI restriction enzymes (1 unit/μg of DNA). The chimeric vector pHKCE-10 was also digested with these two enzymes. The 4.5 kb pSV2gpt ClaI -BamHI fragment and the 9 kb ClaI -BamHI pHKCE-10 fragment were isolated on DEAE 81 paper as described in Example 13 B. A standard ligation reaction as described above was done using 375 ng of the 9 kb fragment insert DNA and 200 ng of the 4.5 kb vector DNA. Following transformation of HB101, a recombinant plasmid, designated pGCEMK, was identified by restriction mapping of the plasmid DNA. One further modification to this plasmid was the addition of a putative non-tissue specific enhancer comprising an approximate 80 base pair region of the human c-los gene (Treisman, R., Cell 42, 889–902, 1985; Chen, W. S. et al. Nature 238, 820–823, 1987. This 80 bp region was first synthesized and cloned into pUC19 by including AatII and HindIII restriction ends. The enhancer element was removed from pUC19 and the 3' overhang ends of these restriction sites were filled in as follows: 20 μg of AatII/HindIII digested pUC19-SRE vector were mixed with 3 μl of 10 x T4 polymerase buffer (700 mM Tris, pH 7.4, 100 mM MgCl$_2$; 50 mM DTT), 3 μl of dNTP mix (0.5 mM each of dATP, dTTP, dCTP, and dGTP pH 7.0), 3 μl of water and 1 μg (5 units) of T4 DNA polymerase from GIBCO-BRL (Gaithersburg, Md.). The mixture was incubated at 37° C. for 15 minutes then heated to 70° C. for 10 minutes. After a phenol/chloroform extraction and ethanol precipitation ClaI linkers were added to the ends of the 102 bp element as described above. Two copies of the enhancer element were ligated into the single ClaI site of pGCEMK as described above. This plasmid is the kappa light chain expression vector used to prepare the CEM chimeric light chain producing cell line called SRE 3.9.

Example 14 DNA Sequencing of Vectors and Cloned Genes

Sequencing of the cloned heavy chain gene pNCEMγ1-CHEL13 was accomplished by standard procedures for double stranded templates using the protocols provided by the sequencing kit Sequenase, commercially available from U.S. Biochemicals (Cleveland, Ohio), and the Bluescript/DNA Sequencing System, commercially available from Stratagene, Inc. (La Jolla, Calif.) as adapted to the Genesis 2000 automated sequencer from DuPont (Wilmington, Del.). From the DNA sequences obtained for the cloned heavy region gene, the amino acid sequence of the polypeptide encoded was deduced by a computer software program, MAPSEQ, commercially available from DNAStar, (Madison, Wis.).

Example 15 transfection of Antibody Genes

Example 15.A. Transfection of Chimeric Light Chain Gene with the Chimeric Construct pGCEMK(SRE)

The light chain immunoglobulin encoding plasmid used for transfection was pGCEMK(SRE) which is described in the Example 13C. above. The pGCEMK(SRE) plasmid, containing the murine variable light (Vk) gene fused to the human kappa gene, was first transfected into SP2/0 hybridoma cells by the electroporation technique described by Chu, et al. (Nucleic Acids Research 15:1311–1325 (1987)). The SP2/0 cells were grown in media containing 10% FBS and were maintained in log phase growth for the three days preceding electroporation. Twenty μg of the plasmid vector pGCEMK(SRE) was linearized using the restriction enzyme PvuI(1 u/μl) and the Reaction Buffer #7 from GIBCO-BRL, (Gaithersburg, Md.). At the time of transfection the SP2/0 cells were collected by centrifugation in an IEC clinical centrifuge (800 rpm, 10 min, room temperature). Cells were then washed in Hanks Buffered Saline Solution from Gibco Laboratories (Grand Island, N.Y.) containing 6 mM dextrose and resuspended at a final concentration of $1.0 \times 10^7$ cells/ml. 0.5 ml of cells were aliquotted into cuvettes at a density of $1 \times 10^7$ cells/ml and the linearized DNA was added. Electroporation was done using the Cell - Porator from GIBCO-BRL (Gaithersburg, Md.) with settings of 300 μF and 350 volts. The electroporated cells were then resuspended in HH3 medium plus 10% fetal calf serum at a density of $2 \times 10^5$/ml (in T75 flasks) for 72 hours. (37° C. 5% CO$_2$). Cells were then plated in the appropriate antibiotic at a density of $1 \times 10^5$ cells/ml in 24 well plates; SP2/0 cells containing pGCEMK(SRE) were plated in HMAX Media (50 ng/ml Hypoxanthine, 250 ng/ml Mycophenolic Acid and 50 μg/ml Xanthine), available from Sigma (St. Louis, Mo.). 200 μl of supernatant was collected from each well which contained HMAX resistant colonies. This supernatant was then assayed for the presence of a human kappa constant region gene which would indicate expression of the chimeric immunoglobulin genes of pGCEMK(SRE).

Example 15.B. Identification of SP2/0 Cells Secreting Chimeric Cem Light Chain

Transfected SP2/0 cells expressing the chimeric CEM kappa genes were identified by a standard enzyme-linked immunosorbent assay (ELISA), as described by Engvall, E. and Perimann, P.,(*Immunochemistry*, 8:871–874 (1971)) for human kappa. The purpose of this assay was to identify those cells secreting the chimeric kappa chain polypeptide coded for by pGCEMK(SRE) plasmid vector. A 5 μg/ml solution of goat anti-human kappa chain (Tago #4106 Tago Inc., 887 Mitten Road, Burlingame, Calif.) in 10 mM sodium phosphate pH 7.4 was prepared. Each well of a 96 well plate was coated with 50 μl of this solution. The plates were then incubated overnight at 37° C. Plates were then rinsed thoroughly in H$_2$O, and then PBS+0.1% Tween (w/v). Fifty μl of the supernatant fractions were added to each well, and incubated for 2 hours at room temperature. Plates were again rinsed as detailed above. A goat anti-human kappa chain alkaline phosphatase conjugate (Tago #2496 Tago Inc., 887 Mitten Road, Burlingame, Calif.) was diluted 1:1000 in the same medium as the supernatant material. 100 μl were added per well and allowed to incubate for 1 hour at room temperature. Plates were rinsed as above. The alkaline phosphatase substrate was prepared as per package instruction, one tablet per 3 ml of distilled H$_2$O and 150 μl of this substrate was added to each well and allowed to incubate 30 minutes at 37° C. The reaction was quenched with 50 μl of 300 mM EDTA and then the absorbance was read at 405 nM. Those supernatants showing the highest levels of kappa expression were subcloned and expanded for introduction of the chimeric construct pNCEMG1-CHEL 13.

Example 15.C. Transfection of Chimeric Kappa Producing Cells with the Heavy Chain Chimeric Construct PNCEMG1 - CHEL 13

The heavy chain immunoglobulin encoding plasmid used for transfection of SP2/0 cells was pNCEMG1-CHEL 13, derived from constructs detailed in Example 13. A subcloned population of cells expressing the chimeric CEM kappa genes was electroporated with the plasmid construct containing the chimeric CEM heavy chain genes. As for the kappa gene electroporation the SP2/0 chimeric kappa producing cells (SRE 3.9) were maintained at log phase of growth for the three days preceding the electroporation. Twenty micrograms of the plasmid DNA pNCEMG1-CHEL 13 was linearized with the enzyme PvuI in Reaction Buffer #6 from GIBCO-BRL (Gaithersburg, Md.). Cells were collected, washed and resuspended at a density of $1 \times 10^7$ cells/mi. The DNA was added and the mixture was electroporated as described in Example 15.A above. Cells were plated at $2.5 \times 10^5$ cells/ml in HH3 media plus 10% fetal calf serum plus HMAX and grown for 72 hours at 37° C., 5% $CO_2$. Cells were then plated at $5 \times 10^4$/ml in 24 well plates in medium containing HMAX and G418 antibiotic (Geneticin) from GIBCO-BRL (Gaithersburg, Md.) at an active concentration of 500 µg/ml. Selection was maintained for 14 days at which time those wells with HMAX/G418 resistant colonies were identified for further analysis.

Example 16 Identification and Analysis of Cells Secreting CHEL-13 ANTIBODY

Example 16.A. Elisa of Assembled IgG1 Antibody Expression.

Detection of assembled antibodies was carried out by coating the microtiter plate wells with goat anti-human IgG antibody reagent (Tago #3100, Tago Inc., 887 Mitten Road, Burlingame, Calif.) at 5 µg/ml in 10 mM phosphate pH 7 to 8. Plates were dried overnight at 37° C., then washed with PBS and 0.1% Tween-20, then $H_2O$. Fifty µl of the cell supernatant were added to each well and incubated for 2 hours at room temperature. Plates were again rinsed as detailed above. A goat anti-human kappa chain alkaline phosphatase conjugate (Tago #2496 Tago Inc., 887 Mitten Road, Burlingame, Calif.) was diluted 1:1000 in the same medium as the supernatant material. 100 µl were added per well and allowed to incubate for 1 hour at room temperature. Plates were rinsed as above. The alkaline phosphatase substrate was prepared as per package instruction, one tablet per 3 ml of distilled $H_2O$ and 150 µl of this substrate was added to each well and allowed to incubate 30 minutes at 37° C. Purified protein from a transfectoma XCEM 449.08 was used as a positive control.

Example 16.B. Quantitation of Assembled Chimeric Antibodies.

The quantitation of intact antibody was accomplished essentially as described in the assembled Ig ELISA. Standard curves were generated by plating serial dilutions of a known concentration of the chimeric CEM antibody in a range of 5 to 180 ng/ml. The optical densities were read at 405 nm and each sample was quantitated against the appropriate standard curve.

Example 17 Purification of CHEL-13 Antibody 300 ml of culture supernatant from terminal cultures of CHEL-13 secreting cells grown in serum free or 1% fetal calf serum containing media was dialyzed against 10 µl of Buffer A (100 mM $NaH_2PO_4$ (pH 7.4); 100 mM NaCl) at 4° C. for 18 h. Following dialysis the media was centrifuged at 3000 x g for 10 min. The clarified media was decanted. A 4.6×50 nun iminodiacetate column from Perspective Biosystems (Cambridge, Mass.) was loaded with $Ni^{2+}$ according to the manufacturer's instructions. The $Ni^{2+}$ loaded column was equilibrated with Buffer A. The clarified media was loaded onto the column using an HPLC pump (model 510) from Waters (South San Francisco, Calif.) at a flow rate of 10 ml/min. After the media was loaded, the column was washed with 50 ml of Buffer A. The column was transferred to a Model 1090 HPLC from Hewlett Packard (Palo Alto, Calif.). The column was then washed with $\geq$ 15 ml of Buffer A at a flow rate of 3 ml/min. The column was washed successively with 15 ml 50% Buffer A; 50% Buffer B (100 mM $NaH_2PO_4$ (pH 4.25): 100 mM NaCl) then with 230 ml Buffer B. Following these washes the column was re-equilibrated with 6 ml Buffer A. Bound CHEL-13 was eluted with a linear gradient from Buffer A to Buffer C (1M glycine (pH 8.7); 100 mM NaCl) developed over 10 min. Fractions were collected and analyzed for antibody content by SDS-PAGE. The antibody containing fractions were dialyzed against a 800 fold excess of PBS (10 mM $Na_2HPO_4$ (pH7.0); 150 mM NaCl) at 40° C. for 18 hours. The pooled antibody was concentrated using an Amicon concentrating cell with a YM 10 membrane from W.R. Grace and Co. (Danvers, Mass.). Contaminating $Ni^{2+}$ was removed as follows: (1) the antibody solution was diluted 10-fold with 10 mM EDTA in PBS; (2) the antibody was reconcentrated to its original volume; (3) the antibody was then diluted 10-fold with EDTA-free PBS then concentrated to its original volume; (4) the antibody was diluted 20-fold with EDTA-free PBS and reconcentrated; (5) step (4) was repeated until the EDTA had been diluted by at least a factor of 80,000. The final concentration of antibody was estimated by absorbance at 280 nm (assuming $A^{0.1\%}$ (1 cm) = 1.4) and found to be 450 µg/ml.

Example 18 Atomic Force Microscopy Images on C-Terminal Metal-Binding Peptides

Example 18.A. Preparation of a Suitable Surface to Contain Metal Ions

5 µl of 1 mM nickel chloride was spotted on a freshly cleaved mica surface, allowed to sit for 1 minute, and rinsed with Milli-Q ® water. This was air-dried at room temperature for 20 minutes, and imaged using an Atomic Force microscope from Digital Instruments, Inc. (Santa Barbara, Calif.) under PBS (DH 7.0) using a 12 micrometer scanner head and a 100 micrometer cantilever. FIG. 23 shows the image of mica alone, and FIG. 24 the nickel-mica image. The force applied to the cantilever tip is approximately $10^{-9}$ Newtons.

Example 18.B. Antibody Bound to Nickel-Mica

100 µl of 0.5 µg/ml CHEL13 was injected into the fluid cell on a freshly cleaved mica surface, and was allowed to be in contact with the mica surface for 10 minutes. The fluid cell was then flushed with PBS, and imaged under PBS (pH 7). The force was approximately $10^{-9}$ Newtons. Smearing of the protein by the cantilever movement suggests that the protein is not binding to the mica surface alone. See FIG. 25. XCEM 449, an antibody not containing the metal binding peptide, was then tested on a nickel-mica surface. 5 μl of 1 mM nickel chloride was spotted on a freshly cleaved mica surface, allowed to sit for 1 minute, and rinsed with Milli-Q ® water. This was air-dried at room temperature for 20 minutes, and attached to a fluid cell. 100 μl of 0.5 μg/ml XCEM 449 was injected into the fluid cell for 10 minutes, then flushed with PBS. Smearing of the protein by the cantilever, which suggests that the protein is nonspecifically bound to the mica, is illustrated in FIG. 26.

Mica-Nickel with CHEL13 was then run in the following manner. Five μl of 1 mM nickel chloride was spotted on a freshly cleaved mica surface, allowed to sit for 1 minute, and rinsed with Milli-Q ® water. This was air-dried at room temperature for 20 minutes, and attached to the fluid cell. 100 μl of 0.5 μg/ml CHEL 13 was injected into the fluid cell and allowed to be in contact with the nickel-mica surface for 10 minutes. The fluid cell was then flushed with PBS and imaged. FIG. 27 shows this image. Globular structures that did not move with the cantilever suggest that the material is bound to the nickel-mica surface. Size determinations of the structures showed them to be approximately 142 angstroms by 34 angstroms. This is comparable to measurements done by electron microscopy which yielded 150 angstroms by 38 angstroms. Cantilever measurement of distance is dependent upon the rigidity of the structure measured.

To demonstrate that the metal binding (chelating) peptide is actually binding to nickel, the following experiment was performed. 5 μl of 1 mM nickel chloride was spotted on a freshly cleaved mica surface, allowed to sit for 1 minute, and rinsed with Milli-Q ® water. This was air dried at room temperature for 20 minutes, and attached to the fluid cell. 180 μl of CHEL13 (0.5 μg/ml) was preincubated for 30 minutes with 20 μl of nickel chloride (10 mM). 100 μl of this material was injected into the fluid cell and incubated for 10 minutes with the nickel-mica surface. The fluid cell was then flushed with PBS and imaged. As shown in FIG. 28, the protein was moved by cantilever, yielding smeared images. This demonstrates that the binding to the surface is indeed occurring through the metal binding (chelating) peptide.

We claim:

1. A method of immobilizing a biologically active molecule on a support, said method consisting of the steps of:
   (a) covalently bonding a chelating agent to a biologically active molecule, said chelating agent being capable of chelating transition metal ion selected from the group consisting of Co(II), Cr(II) and Ru(III);
   b) contacting the product of step (a) with a solid support containing said transition metal ion bound thereto whereby said chelating agent chelates said transition metal ion and the product of step (a) is attached to the support; and
   (c) treating the product of step (b) with an oxidizing agent or a reducing agent to change the oxidation state of said transition metal ion to Co(III), Cr(III) or Ru(II), respectively, to provide a kinetically inert oxidation state whereby the biologically active molecule is immobilized on the support.

2. The method of claim 1 wherein said metal ion is Co(II).

3. The method of claim 1 wherein said chelating agent is selected from the group consisting of bidentate ligands, tridentate ligands, quadridentate ligands, tripod ligands, and macrocyclic ligands.

4. The method of claim 3 wherein said chelating agent is selected from the group consisting of iminodiacetic acid (NTA), nitrilotriacetic acid terpyridine, bipyridine, triethylenetetraamine, biethylenetriamine and 1,4,7-triazacyclonane.

5. The method of claim 4 wherein said chelating agent is selected from the group consisting of iminodiacetic acid (NTA), nitrilotriacetic acid, terpyridine, bipyridine, triethylenetetraamine, and biethylenetriamine.

6. The method of claim 5 wherein said chelating agent is iminodiacetic acid.

7. The method of claim 1 wherein said chelating agent is a chelating peptide.

8. The method of claim 7 wherein said chelating peptide is selected from the group consisting of His-Trp-His-Met-Tyr, His-His-His-Met-Tyr, His-Trp-His-Trp-His, His-Trp-His-His-His, His-His-His-His-Tyr-Met-His-His-His-His-Tyr, His-His-His-His-His, His-Gly-His-Gly-Gly-Gly-His-Gly-His, and His-Gly-His-Gly-Giy-Gly-Gly-Giy-Gly-His-Gly-His.

9. The method of claim 3 wherein said biologically active molecule is selected from the group consisting of fluorescent dyes, radioactive ligands, nucleotides, proteins, carbohydrates, and lipids.

10. The method of claim 9 wherein said biologically active molecule is a protein.

11. The method of claim 10 wherein said protein is an immunoreactive protein.

12. The method of claim 7 wherein said biologically active molecule is selected from the group consisting of fluorescent dyes, radioactive ligands, nucleotides, proteins, carbohydrates and lipids.

13. The method of claim 12 wherein said biologically active molecule is a protein.

14. The method of claim 13 wherein said protein is an immunoreactive protein.

15. The method of claim 3 or 7 wherein said biologically active molecule is a drug.

* * * * *

SEQUENCE LISTING ( 1 ) GENERAL INFORMATION:

( i i i ) NUMBER OF SEQUENCES: 38

( 2 ) INFORMATION FOR SEQ ID NO:1:

( i ) SEQUENCE CHARACTERISTICS:
( A ) LENGTH: 5 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:1:

His  Trp  His  Met  Tyr
1                    5

( 2 ) INFORMATION FOR SEQ ID NO:2:

( i ) SEQUENCE CHARACTERISTICS:
( A ) LENGTH: 5 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:2:

His  His  His  Met  Tyr
1                    5

( 2 ) INFORMATION FOR SEQ ID NO:3:

( i ) SEQUENCE CHARACTERISTICS:
( A ) LENGTH: 5 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:3:

His  His  His  His  Tyr
1                    5

( 2 ) INFORMATION FOR SEQ ID NO:4:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:4:

His  Trp  His  Trp  His
    1                      5

( 2 ) INFORMATION FOR SEQ ID NO:5:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:5:

His  Trp  His  His  His
    1                      5

( 2 ) INFORMATION FOR SEQ ID NO:6:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:6:

His  His  His  His  Tyr  Met  His  His  His  His  Tyr
    1                      5                                10

( 2 ) INFORMATION FOR SEQ ID NO:7:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:7:

His  His  His  His  His
    1                      5

( 2 ) INFORMATION FOR SEQ ID NO:8:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:8:

His  Trp  His  His  His  Pro
    1                      5

( 2 ) INFORMATION FOR SEQ ID NO:9:

( i ) SEQUENCE CHARACTERISTICS:
    ( A ) LENGTH: 9 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:9:

His Gly His Gly Gly Gly His Gly His
1               5

( 2 ) INFORMATION FOR SEQ ID NO:10:

( i ) SEQUENCE CHARACTERISTICS:
    ( A ) LENGTH: 12 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:10:

His Gly His Gly Gly Gly Gly Gly Gly His Gly His
1               5                           10

( 2 ) INFORMATION FOR SEQ ID NO:11:

( i ) SEQUENCE CHARACTERISTICS:
    ( A ) LENGTH: 23 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:11:

Met Glu Val Lys Lys Pro Ala Ala Ala Ala Ala Pro Gly Thr Ala Glu
1               5                   10                  15

Lys Leu Ser Pro Lys Ala Ala
            20

( 2 ) INFORMATION FOR SEQ ID NO:12:

( i ) SEQUENCE CHARACTERISTICS:
    ( A ) LENGTH: 10 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:12:

Met Lys Gly Asp Pro Lys Lys Lys Xaa Trp
1               5                   10

( 2 ) INFORMATION FOR SEQ ID NO:13:

( i ) SEQUENCE CHARACTERISTICS:
    ( A ) LENGTH: 48 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:13:

GATCACTAGT ATGCACTGGC ATCACCATAT GCCGCCCAAA ACCCCCCG           48

( 2 ) INFORMATION FOR SEQ ID NO:14:

( i ) SEQUENCE CHARACTERISTICS:
    ( A ) LENGTH: 37 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:14:

GATCGGATCC ACTAGTTCAT TTCTCTTCCT TGTTTGA          37

( 2 ) INFORMATION FOR SEQ ID NO:15:

( i ) SEQUENCE CHARACTERISTICS:
        ( A ) LENGTH: 52 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:15:

GATCGCTAGC ATATGCACTG GCATCACCAT ATGATTTTAA ATTCAGCAAG TG      52

( 2 ) INFORMATION FOR SEQ ID NO:16:

( i ) SEQUENCE CHARACTERISTICS:
        ( A ) LENGTH: 55 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:16:

ATCGCGATCG CAGTGGCACT GGCTGGTTTC GCCACCGTGG CGCAGGCCGA CATTG     55

( 2 ) INFORMATION FOR SEQ ID NO:17:

( i ) SEQUENCE CHARACTERISTICS:
        ( A ) LENGTH: 67 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:17:

TGCCACTGCG ATCGCGATAG CTGTCTTTTT CATGATATAT CTCCTTCTAT TTCAGCTCCA     60

GCTTGGT                                                                                                     67

( 2 ) INFORMATION FOR SEQ ID NO:18:

( i ) SEQUENCE CHARACTERISTICS:
        ( A ) LENGTH: 48 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:18:

TAGCCGGATC CAAGCTTGGA ATTCCTATGA GGAGACGGTG ACCGTGGT        48

( 2 ) INFORMATION FOR SEQ ID NO:19:

( i ) SEQUENCE CHARACTERISTICS:
        ( A ) LENGTH: 72 base pairs
        ( B ) TYPE: nucleic acid
        ( C ) STRANDEDNESS: single ( D ) TOPOLOGY: linear ( i i ) MOLECULE TYPE: DNA (genomic)

( x i ) SEQUENCE DESCRIPTION: SEQ ID NO:19:

GCTATCGCGA TCGCAGTGGC ACTGGCTGGT TTCGCTACCG TGGCGCAGGC CGATGTGCAG    60

CTGGTGGAGT CT    72

( 2 ) INFORMATION FOR SEQ ID NO:20:

( i ) SEQUENCE CHARACTERISTICS:
        ( A ) LENGTH: 41 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:20:

AAACATTGGC ATCATCATTG AAAGGAGATA TATCATGAAA A    41

( 2 ) INFORMATION FOR SEQ ID NO:21:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:21:

TTCAATGATG ATGCCAATGT TCAGTTCCA GTTTGGTACC AGCACCGAAC GTGA    54

( 2 ) INFORMATION FOR SEQ ID NO:22:

( i ) SEQUENCE CHARACTERISTICS:
        ( A ) LENGTH: 63 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:22:

ATTGGATCCT AAGCTTCAGG AGGAAACGGT AACAGTGGTA CCTGCACCCC AAACATCGAA    60

GTA    63

( 2 ) INFORMATION FOR SEQ ID NO:23:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:23:

ATTCATTAAT GCAGCTGGCA CGACAGGTTT    30

( 2 ) INFORMATION FOR SEQ ID NO:24:

( i ) SEQUENCE CHARACTERISTICS:
        ( A ) LENGTH: 70 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:24:

| | | | | | |
|---|---|---|---|---|---|
| ATATTGGATC | CTTAGTGATG | GTGCCAGTGG | GAGGAAACGG | TAACCGTAGT | ACCTGCACCC | 60
| CAAACATCGA | | | | | | 70

( 2 ) INFORMATION FOR SEQ ID NO:25:

( i ) SEQUENCE CHARACTERISTICS:
        ( A ) LENGTH: 88 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:25:

| | | | | | |
|---|---|---|---|---|---|
| TGCTGGTACC | AAACTGGAAC | TGAAAGGTGG | TAGCGGTGGT | AGCGGTGGTT | CTGGTGGCTC | 60
| CGGAGGTGAT | GTGCAGCTGG | TGGAGTCT | | | | 88

( 2 ) INFORMATION FOR SEQ ID NO:26:

( i ) SEQUENCE CHARACTERISTICS:
        ( A ) LENGTH: 87 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:26:

| | | | | | |
|---|---|---|---|---|---|
| AATTCTCTAG | ATAACGAGGC | GCAAAAAATG | AAAAAGACAG | CTATCGCGAT | CGCAGTGGCA | 60
| CTGGCTGGTT | TCGCCACCGT | GGCGCAG | | | | 87

( 2 ) INFORMATION FOR SEQ ID NO:27:

( i ) SEQUENCE CHARACTERISTICS:
        ( A ) LENGTH: 87 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:27:

| | | | | | |
|---|---|---|---|---|---|
| GATCCTGCGC | CACGGTGGCG | AAACCAGCCA | GTGCCACTGC | GATCGCGATA | GCTGTCTTTT | 60
| TCATTTTTTG | CGCCTCGTTA | TCTAGAG | | | | 87

( 2 ) INFORMATION FOR SEQ ID NO:28:

( i ) SEQUENCE CHARACTERISTICS:
        ( A ) LENGTH: 298 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:28:

| | | | | | |
|---|---|---|---|---|---|
| CATATGGAAT | TCATGTTCGT | CAATCAGCAC | CTTTGTGGTT | CTCACCTCGT | TGAAGCTCTC | 60
| TACCTAGTGT | GCGGGGAACG | AGGCTTCTTC | TACACACCCA | AGACCCGCCG | GGAGGCAGAG | 120
| GACCTGCAGG | TGGGGCAGGT | GGAGCTGGGC | GGGGGCCCTG | GTGCAGGCAG | CCTGCAGCCC | 180
| TTGGCCCTGG | AGGGGTCCCT | GCAGAAGCGT | GGCATTGTGG | AACAATGCTG | TACCAGCATC | 240
| TGCTCCCTCT | ACCAGCTGGA | GAACTACTGC | AACTAGACGC | AGCCCGCAGG | CCGGATCC | 298

( 2 ) INFORMATION FOR SEQ ID NO:29:

( i ) SEQUENCE CHARACTERISTICS:
        ( A ) LENGTH: 596 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:29:

```
CATATGTTCC  CAACCATTCC  CTTATCCAGG  CTTTTTGACA  ACGCTATGCT  CCGCGCCAT      60
CGTCTGCACC  AGCTGGCCTT  TGACACCTAC  CAGGAGTTTG  AAGAAGCCTA  TATCCCAAAG    120
GAACAGAAGT  ATTCATTCCT  GCAGAACCCC  CAGACCTCCC  TCTGTTTCTC  AGAGTCTATT   180
CCGACACCCT  CCAACAGGGA  GGAAACACAA  CAGAAATCCA  ACCTAGAGCT  GCTCCGCATC   240
TCCCTGCTGC  TCATCCAGTC  GTGGCTGGAG  CCCGTGCAGT  TCCTCAGGAG  TGTCTTCGCC   300
AACAGCCTGG  TGTACGGCGC  CTCTGACAGC  AACGTCTATG  ACCTCCTAAA  GGACCTAGAG   360
GAAGGCATCC  AAACGCTGAT  GGGGAGGCTG  GAAGATGGCA  GCCCCCGGAC  TGGGCAGATC   420
TTCAAGCAGA  CCTACAGCAA  GTTCGACACA  AACTCACACA  ACGATGACGC  ACTACTCAAG   480
AACTACGGGC  TGCTCTACTG  CTTCAGGAAG  GACATGGACA  AGGTCGAGAC  ATTCCTGCGC   540
ATCGTGCAGT  GCCGCTCTGT  GGAGGGCAGC  TGTGCCTTCT  AGCTGCCCCC  GGATCC        596
```

( 2 ) INFORMATION FOR SEQ ID NO:30:

( i ) SEQUENCE CHARACTERISTICS:
        ( A ) LENGTH: 46 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:30:

```
CTAGAGGGTA  TTAATAATGT  ATCGCTATTA  TAAAGGAGGA  TAAACA                    46
```

( 2 ) INFORMATION FOR SEQ ID NO:31:

( i ) SEQUENCE CHARACTERISTICS:
        ( A ) LENGTH: 44 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:31:

```
TATGTTTATC  CTCCTTTATA  ATAGCGATAC  ATTATTCCTA  CCCT                      44
```

( 2 ) INFORMATION FOR SEQ ID NO:32:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:32:

```
TATGCACTGG  CATCACCA                                                      18
```

( 2 ) INFORMATION FOR SEQ ID NO:33:

( i ) SEQUENCE CHARACTERISTICS:
        ( A ) LENGTH: 18 base pairs (B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:33:

TATGGTGATG CCAGTGCA                                                                          18

(2) INFORMATION FOR SEQ ID NO:34:

(i) SEQUENCE CHARACTERISTICS:
        (A) LENGTH: 47 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:34:

GATCGCTAGC ATGCACTGGC ATCACCATAT GCCGCCCAAA CCCCCCG                                           47

(2) INFORMATION FOR SEQ ID NO:35:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:35:

GATCGGATCC GCTAGCTCAT TTCTCTTCCT TGTTTGA                                                      37

(2) INFORMATION FOR SEQ ID NO:36:

(i) SEQUENCE CHARACTERISTICS:
        (A) LENGTH: 52 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:36:

GATCGCTAGC ATATGCACTG GCATCACCAT ATGATTTTAA ATTCAGCAAG TG                                     52

(2) INFORMATION FOR SEQ ID NO:37:

(i) SEQUENCE CHARACTERISTICS:
        (A) LENGTH: 387 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:37:

ATGAAAAGA CAGCTATCGC GATCGCAGTG GCACTGGCTG GTTTCGCCAC CGTGGCGCAG                               60

GCCGACATTG TGATGACCCA GTCTCAAAAA TTCATGTCCA CATCAGTAGG AGACAGGGTC                             120

AGCATCACCT GCAAGGCCAG TCAGAATGTT CGTACTGCTG TTGCCTGGTA TCAACAGAAA                             180

CCAGGGCAGT CTCCTAAAGC ACTGATTTAC TTGGCATCCA ACCGGTACAC TGGAGTCCCT                             240

GATCGCTTCA CAGGCAGTGG ATCTGGGACA GATTTCACTC TCACCATTAC CAATGTGCAA                             300

TCTGAAGACC TGGCAGATTA TTTCTGTCTG CAACATTGGA ATTATCCGCT CACGTTCGGT                             360

GCTGGGACCA AGCTGGAGCT GAAATAG                                                                387

( 2 ) INFORMATION FOR SEQ ID NO:38:

( i ) SEQUENCE CHARACTERISTICS:
    ( A ) LENGTH: 444 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:38:

```
ATGAAAAGA  CAGCTATCGC  GATCGCAGTG  GCACTGGCTG  GTTTCGCCAC  CGTGGCGCAG     60
GCCGATGTGC  AGCTGGTGGA  GTCTGGGGGA  GGCTTAGTGC  AGCCTGGAGG  GTCCCGGAAA   120
CTCTCCTGTG  CAGCCTCTGG  ATTCACTTTC  AGTAACTTTG  GAATGCACTG  GATTCGTCAG   180
GCTCCAGAGA  AGGGACTGGA  GTGGGTCGCA  TACATTAGTG  GTGGCAGTAG  TACCATCTAC   240
TATGCAGACA  CAGTGAAGGG  CCGATTCACC  ATCTGGAGAG  ACAATCCCAG  GAACACCCTC   300
TTCCTGCAAA  TGACCAGTCT  AAGGTCTGAG  GACACGGCCA  TGTTTTACTG  TGCAAGAGAT   360
TACTACGCTA  ACAACTACTG  GTACTTCGAT  GTTGGGGTG   CAGGTACTAC  GGTTACCGTT   420
TCCTCCCACT  GGCACCATGA  CTAA                                             444
```